US011065326B2

(12) United States Patent
Martinez-Sobrido et al.

(10) Patent No.: US 11,065,326 B2
(45) **Date of Patent: *Jul. 20, 2021**

(54) LIVE-ATTENUATED VACCINE HAVING MUTATIONS IN VIRAL POLYMERASE FOR THE TREATMENT AND PREVENTION OF CANINE INFLUENZA VIRUS

(71) Applicants: University of Rochester, Rochester, NY (US); Cornell University, Ithaca, NY (US)

(72) Inventors: Luis Martinez-Sobrido, Rochester, NY (US); Aitor Nogales-Gonzalez, Rochester, NY (US); Colin Parrish, Ithaca, NY (US)

(73) Assignees: University of Rochester, Rochester, NY (US); Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/589,247

(22) Filed: Oct. 1, 2019

(65) Prior Publication Data

US 2020/0023055 A1 Jan. 23, 2020

Related U.S. Application Data

(63) Continuation of application No. 15/753,671, filed as application No. PCT/US2016/047715 on Aug. 19, 2016, now Pat. No. 10,478,489.

(Continued)

(51) Int. Cl.

*A61K 39/145* (2006.01)
*A61P 31/16* (2006.01)

(Continued)

(52) U.S. Cl.

CPC ............ *A61K 39/145* (2013.01); *A61K 39/12* (2013.01); *A61P 31/16* (2018.01);

(Continued)

(58) Field of Classification Search

None

See application file for complete search history.

(56) References Cited

U.S. PATENT DOCUMENTS 7,722,884 B2 5/2010 Shields
7,959,929 B2 6/2011 Crawford (Continued)

FOREIGN PATENT DOCUMENTS

WO 2007024947 A2 3/2007
WO 2011044561 A1 4/2011

(Continued)

OTHER PUBLICATIONS

Solorzano et al. (Journal of Virology. May 2010; 84 (9): 4587-4596).*

(Continued)

*Primary Examiner* — Shanon A. Foley
(74) *Attorney, Agent, or Firm* — Riverside Law LLP

(57) ABSTRACT

The present invention relates to compositions and methods for the treatment and prevention of canine influenza virus (CIV) and CIV-related pathology. The present invention is based in part upon the discovery that various mutations in segment 1 and segment 2 of the CIV genome, thereby encoding mutant PB2 and PB1 protein, render the virus to be temperature-sensitive.

19 Claims, 18 Drawing Sheets

Specification includes a Sequence Listing.

Related U.S. Application Data

(60) Provisional application No. 62/207,571, filed on Aug. 20, 2015.

(51) Int. Cl.
*A61K 39/12* (2006.01)
*A61K 39/00* (2006.01)

(52) U.S. Cl.
CPC ................ *A61K 2039/5254* (2013.01); *A61K 2039/543* (2013.01); *A61K 2039/552* (2013.01); *A61K 2039/58* (2013.01); *C12N 2760/16134* (2013.01)

(56) References Cited

U.S. PATENT DOCUMENTS

| | | | | |
|---|---|---|---|---|
| 8,246,962 | B2 | 8/2012 | Cho | |
| 10,478,489 | B2 * | 11/2019 | Martinez-Sobrido | A61K 39/12 |
| 2011/0150912 | A1 * | 6/2011 | Perez | A61K 39/145 424/186.1 |
| 2018/0243401 | A1 | 8/2018 | Martinez-Sobrido | |
| 2018/0256703 | A1 | 9/2018 | Martinez-Sobrido | |
| 2019/0125860 | A1 | 5/2019 | Martinez-Sobrido | |
| 2020/0023055 | A1 * | 1/2020 | Martinez-Sobrido | A61K 39/12 |

FOREIGN PATENT DOCUMENTS

| | | | |
|---|---|---|---|
| WO | 2013030176 | A2 | 3/2013 |
| WO | 2015010073 | A1 | 1/2015 |

OTHER PUBLICATIONS

Zhou et al. (Vaccine. 2012; 30: 3691-3702).*
Sequence alignment of SEQ ID 3 with SEQ ID 3 of U.S. Pat. No. 10,478,489 Nov. 2019.*
Sequence alignment of SEQ ID 4 with SEQ ID 4 of U.S. Pat. No. 10,478,489 Nov. 2019.*
Alignment of SEQ ID 1 with SEQ ID 1 of U.S. Pat. No. 10,478,489 Nov. 2019.*
Alignment of SEQ ID 2 with SEQ ID 2 of U.S. Pat. No. 10,478,489 Nov. 2019.*
Sequence alignment of SEQ ID 1 with Geneseq db acc No. AFB78958 by Minke et al in USPgPub2007048819 Mar. 2007.*
Sequence alignment of SEQ ID 2 with Geneseq db acc No. AFB78958 by Minke et al in USPgPub2007048819 Mar. 2007.*
Alignment of SEQ ID 1 with Geneseq db acc No. AFU64076 by Yoon et al in WO2007048086 Apr. 2007.*
Sequence alignment of SEQ ID 2 with Geneseq db acc No. AFU64076 by Yoon et al in WO2007048086 Apr. 2007.*
Sequence alignment of SEQ ID 3 with Geneseq db acc No. AFU64076 by Yoon et al in WO2007048086 Apr. 2007.*
Alignment of SEQ ID 4 with Geneseq db acc No. AFU64075 by Yoon et al in WO2007048086 Apr. 2007.*
Su et al. (Journal of Clinical Microbiology. May 2014; 52 (5): 1762-1765).*
Zhang et al. (Virus Research. 2013; 175: 52-57).*
Li et al. (Infection, Genetics and Evolution. 2010; 10: 1286-1288).*
Anonymous, "4 Things Pet Owners Should Know About the Dog Flu—C2CND", (Aug. 3, 2015), pp. 1-5, URL: http://c2cnd.org/connect/4-things-pet-owners-know-dog-flu/, (Oct. 27, 2016), XP055314404.
Baker et al., 2013, "Protection against lethal influenza with a viral mimic." J Virol, 87: 8591-8605.
Baker et al., 2015, "Downregulating viral gene expression: codon usage bias manipulation for the generation of novel Influenza A virus vaccines." Future Virology, 10: 715-730.
Baskin et al., 2007, "Functional Genomic and Serological Analysis of the Protective Immune Response Resulting from Vaccination of Macaques with an NS1-Truncated Influenza Virus" J Viral, 81:11817-11827.
Bean et al., 1992, "Evolution of the H3 influenza virus hemagglutinin from human and nonhuman hosts." J Virol, 66:1129-1138.
Belongia et al., 2009, "Effectiveness of inactivated influenza vaccines varied substantially with antigenic match from the 2004-2005 season to the 2006-2007 season." Journal of Infectious Diseases, 199: 159-167.
Belshe et al., 2000, "Correlates of Immune Protection Induced by Live, Attenuated, Cold-Adapted, Trivalent, Intranasal Influenza Virus Vaccine" The Journal of infectious diseases, 181:1133-1137.
Belshe et al., 2007, "Live attenuated versus inactivated influenza vaccine in infants and young children." The New England Journal of Medicine, 356: 685-696.
Both et al., 1983, "Antigenic drift in influenza virus H3 hemagglutinin from 1968 to 1980: multiple evolutionary pathways and sequential amino acid changes at key antigenic sites." J Virol, 48:52.
Bush et al., 1999, "Positive selection on the H3 hemagglutinin gene of human influenza virus A." Molecular biology and evolution, 16: 1457-1465.
Centers for Disease Control and Prevention, 2010, "Licensure of a High-Dose Inactivated Influenza Vaccine for Persons Aged 65 Years (Fluzone High-Dose) and Guidance for Use—United States, 2010" MMWR, 59(16):485-486.
Chan et al., 2008, "The cold adapted and temperature sensitive influenza A/Ann Arbor/6/60 virus, the master donor virus for live attenuated influenza vaccines, has multiple defects in replication at the restrictive temperature." Virology, 380:304-311.
Chao, "A Single Amino Acid Deletion at the Amino Terminus of Influenza Virus Hemagglutinin Causes Malfolding and Blocks Exocytosis of the Molecule in Mammalian Cells," The Journal of Biological Chemistry, 267(4):2142-2148, 1992.
Cheng et al., 2013, The Journal of infectious diseases, 208: 594-602.
Choi et al., 2015, "Development of a dual-protective live attenuated vaccine against H5N1 and H9N2 avian influenza viruses by modifying the NS1 gene" Archives of virology, 160:1729-1740.
Communication pursuant to Article 94(3) EPC received in corresponding European Patent Application No. 16757480.5, dated Sep. 10, 2019. 11 pages.
Cox et al., 1988, "Identification of sequence changes in the cold-adapted, live attenuated influenza vaccine strain, A/Ann Arbor/6/60 (H2N2)." Virology, 167:554-567.
Cox et al., 2008, "FluBlok, a recombinant hemagglutinin influenza vaccine." Influenza and other Respiratory Viruses: 2: 211-219.
Cox et al., 2015, "Development of a mouse-adapted live attenuated influenza virus that permits in vivo analysis of enhancements to the safety of live attenuated influenza virus vaccine." J Viral, 89(6): 3421-3426.
Crawford et al., 2005, "Transmission of equine influenza virus to dogs." Science, 310: 482-485.
De Jong et al., 2007, "Antigenic and genetic evolution of swine influenza A (H3N2) viruses in Europe." J Virol, 81: 4315-4322.
De Villiers et al., 2009, "Efficacy and safety of a live attenuated influenza vaccine in adults 60 years of age and older." Vaccine, 28: 228-234.
Deshpande et al., 2009, "Evaluation of the Efficacy of a Canine Influenza Virus (H3N8) Vaccine in Dogs Following Experimental Challenge" Veterinary therapeutics: research in applied veterinary medicine, 10:103-112.
Dundon et al., 2010, "Serologic Evidence of Pandemic (H1N1) 2009 Infection in Dogs, Italy" Emerging infectious diseases, 16:2019-2021.
Epperson et al., 2013, Human infections with influenza A(H3N2) variant virus in the United States, 2011-2012. Clinical infectious diseases, 57 Suppl 1:S4-S11.
Falcon et al., 2005, "Attenuation and immunogenicity in mice of temperature-sensitive influenza viruses expressing truncated NS1 proteins" The Journal of general virology, 86:2817-2821.
Feng et al., 2015, "Equine and Canine Influenza H3N8 Viruses Show Minimal Biological Differences Despite Phylogenetic Divergence." J Viral, 89: 6860-6873.

(56) References Cited

OTHER PUBLICATIONS

Ferko et al., 2004, "Immunogenicity and Protection Efficacy of Replication-Deficient Influenza A Viruses with Altered NS1 Genes" J Virol, 78:13037-13045.
Garcia-Sastre et al., 1998, "Influenza A Virus Lacking the NS1 Gene Replicates in Interferon-Deficient Systems" Virology, 252:324-330.
Geiss et al., 2002, "Cellular transcriptional profiling in influenza A virus-infected lung epithelial cells: the role of the nonstructural NS1 protein in the evasion of the host innate defense and its potential contribution to pandemic influenza" Proceedings of the National Academy of Sciences, 99:10736-10741.
Gonzalez et al., 2014, "Infection and pathogenesis of canine, equine, and human influenza viruses in canine tracheas." J Viral, 88: 9208-9219.
Gorse et al., 1991, "Superiority of live attenuated compared with inactivated influenza A virus vaccines in older, Chronically ill adults." Chest, 100: 977-984.
Guo et al., 2014, "Induction of CD8 T cell heterologous protection by a single dose of single-cycle infectious influenza virus." J Viral, 88: 12006-12016.
Hai et al., 2008, "Influenza B Virus NS1-Truncated Mutants: Live-Attenuated Vaccine Approach" J Virol, 82:10580-10590.
Hale et al., 2008, "The multifunctional NS1 protein of influenza A viruses" The Journal of general virology, 89:2359-2376.
Hanson et al., "Canine Influenza," Clinicians Brief, University of Georgia, 97-103, 2016.
Hayward et al., 2010, "Microevolution of canine influenza virus in shelters and its molecular epidemiology in the United States." J Virol, 84:12636-12645.
Hickman et al., 2008, "An avian live attenuated master backbone for potential use in epidemic and pandemic influenza vaccines." Journal of General Virology, 89(11): 2682-2690.
Holt et al., 2010, "Serologic prevalence of antibodies against canine influenza virus (H3N8) in dogs in a metropolitan animal shelter." Journal of the American Veterinary Medical Association, 237: 71-73.
Hussain et al., 2010, "Comparison of egg and high yielding MDCK cell-derived live attenuated influenza virus for commmercial production of trivalent influenza vaccine: in vitro cell susceptibility and influenza virus replication kinetics in 3emissive and semi-permissive cells." Vaccine, 28: 3848-3855.
JAVMA News. 2015. Outbreak of canine influenza caused by new strain of virus. J Am Vet Med Assoc. 246:1049, 2 pages.
Jeoung et al., 2013, "A novel canine influenza H3N2 virus isolated from cats in an animal shelter." Veterinary Microbiology, 165: 281-286.
Jin et al., 2003, "Multiple amino acid residues confer temperature sensitivity to human influenza virus vaccine strains (FluMist) derived from cold-adapted A/Ann Arbor/6/60." Virology, 306: 18-24.
Jin et al., 2004, "Imparting temperature sensitivity and attenuation in ferrets to A/Puerto Rico/8/34 influenza virus by transferring the genetic signature for temperature sensitivity from cold-adapted A/Ann Arbor/6/60." J Virol, 78:995-998.
Kappes et al., 2011, "Vaccination with NS-1 truncated H3N2 swine influenza virus rimes T cells and confers cross-protection against an H1N1 heterosubtypic challenge in pigs." Vaccine, 30(2): 280-288.
Katsura et al., 2012, "A replication-incompetent virus possessing an uncleavable hemagglutinin as an influenza vaccine." Vaccine, 30: 6027-6033.
Kohlmeier et al., 2009, "Immunity to respiratory viruses." Annual review of immunology, 27: 61-82.
Lamb et al., 1980, "Mapping of the two overlapping genes for polypeptides NS1 and NS2 on RNA segment 8 of Influenza virus genome" Proceedings of the National Academy of Sciences, 77:1857-1861.
Maassab, 1999, Reviews in medical virology, 9: 237-244.
Maassab., 1968, "Plaque formation of influenza virus at 25 degrees C." Nature, 219:645-646.
Mariana Baz et al., 2014, "A live attenuated H3N8 influenza vaccine is highly immunogenic and efficacious in mice and ferrets." Journal of Virology, 89(3): 1652-1659.
Martinez-Sobrido et al., 2006, "Inhibition of the type I interferon response by the nucleoprotein of the prototypic arenavirus lymphocytic choriomeningitis virus" J Virol, 80:9192-9199.
Martinez-Sobrido et al., 2009, "Identification of Amino Acid Residues Critical for the Anti-Interferon Activity of the Nucleoprotein of the Prototypic Arenavirus Lymphocytic Choriomeningitis Virus" J Virol, 83:11330-11340.
Martinez-Sobrido et al., Journal of Visualized Experiments, (2010), p. 42.
Murphy et al., "An influenza A live attenuated reassortant virus possessing three temperature-sensitive mutations in the PB2 polymerase gene rapidly loses temperature sensitivity following replication in hamsters," Vaccine, 15 (12/13):1372-1378, 1997.
Murphy et al., 2002, "Principles underlying the development and use of live attenuated cold-adapted influenza A and B virus vaccines." Viral immunology, 15: 295-323.
Newbury et al., 2016, "Prolonged intermittent virus shedding during an outbreak of canine influenza A H3N2 virus infection in dogs in three Chicago area shelters: 16 cases (Mar. to May 2015)" Journal of the American Veterinary Medical Association, 248:1022-1026.
Nogales et al., 2014, "Influenza A virus attenuation by codon deoptimization of the NS gene for vaccine development." J Viral, 88: 10525-10540.
Nogales et al., 2015, "Replication-competent influenza A viruses expressing a red fluorescent protein." Virology, 476: 206-216.
Nogales et al., 2016, "Rearrangement of Influenza Virus Spliced Segments for the Development of Live-Attenuated Vaccines." J Virol, 90: 6291-6302.
Notice of Allowance dated Sep. 25, 2019 for U.S. Appl. No. 15/753,671 (pp. 1-7).
Notification of Transmittal of the International Search Report and the Written Opinion of the International Searching Authority, or the Declaration, dated Dec. 22, 2016, received in corresponding International Application No. PCT/ US2016/047715. 20 pages.
Osterholm et al., 2012, "Efficacy and effectiveness of influenza vaccines: a systematic review and meta-analysis" The Lancet Infectious Diseases, 12: 36-44.
Park et al., 2003, "Newcastle Disease Virus (NDV)-Based Assay Demonstrates Interferon-Antagonist Activity for the NDV V Protein and the Nipah Virus V, W, and C Proteins" J Virol, 77:1501-1511.
Parrish et al., 2005, "The Origins of New Pandemic Viruses: The Acquisition of New Host Ranges by Canine Parvovirus and Influenza A Viruses" Annual review of microbiology, 59:553-586.
Parrish et al., 2015, "Influenza Virus Reservoirs and intermediate Hosts: Dogs, Horses, and New Possibilities for Influenza Virus Expoure of Humans" J. Virol, 89:2990-2994.
Pecoraro et al., 2013, "Evaluation of virus isolation, one-step real-time reverse transcription polymerase chain reaction assay, and two rapid influenza diagnostic tests for detecting canine Influenza A virus H3N8 shedding in dogs." Journal of Veterinary Diagnostic Investigation, 25: 402-406.
Pica et al., 2012, "NS1-Truncated Live Attenuated Virus Vaccine Provides Robust Protection to Aged Mice from Viral Challenge" J Virol, 86:10293-10301.
Pica et al., 2013, "Toward a universal influenza virus vaccine: prospects and challenges." Annual Review of Medicine, 64: 189-202.
Powell et al., 2012, "Pseudotyped influenza A virus as a vaccine for the induction of heterotypic immunity." J Virol, 86: 13397-13406.
Pronker et al., 2012, "Development of new generation influenza vaccines: recipes for success?" Vaccine, 30: 7344-7347.
Quinlivan et al., 2005, "Attenuation of Equine Influenza Viruses through Truncations of the NS1 Protein" J Viral, 79:8431-8439.
Ramirez-Martinez et al., 2013, "Evidence of transmission and risk factors for influenza A virus in household dogs and their owners" Influenza and other respiratory viruses, 7:1292-1296.
Randall et al., 2008, "Interterons and viruses: an interplay between induction, signalling, antiviral responses and virus countermeasures" The Journal of general virology, 89:1-47.

(56) References Cited

OTHER PUBLICATIONS

Richt et al., 2006, "Vaccination of Pigs against Swine Influenza Viruses by Using an NS1-Truncated Modified Live-Virus Vaccine" J Viral 80:11009-11018.
Richt et al., 2009, "Attenuated Influenza Virus Vaccines with Modified NS1 Proteins" Current topics in microbiology and immunology, 333:177-195.
Rimmelzwaan et al., 2007, "Influenza virus-specific cytotoxic T lymphocytes: a correlate of protection and a basis for vaccine development" Current opinion in biotechnology, 18:529-536.
Rivailler et al., 2010, "Evolution of canine and equine influenza (H3N8) viruses co-circulating between 2005 and 2008." Virology, 408: 71-79.
Smith et al., 2009, "Origins and evolutionary genomics of the 2009 swine-origin H1N1 influenza A epidemic" Nature, 459:1122-1125.
Snyder et al., 1988, "Four viral genes independently contribute to attenuation of live influenza A/Ann Arbor/6/60 (H2N2) cold-adapted reassortant virus vaccines." J Viral, 62:488-495.
Solorzano et al., 2005, "Mutations in the NS1 Protein of Swine Influenza Virus Impair Anti-Interferon Activity and Confer Attenuation in Pigs" J Virol, 79:7535-7543.
Song et al., 2007, "A New Generation of Modified Live-Attenuated Avian Influenza Viruses Using a Two-Strategy Combination as Potential Vaccine Candidates." Journal of Virology, 81(17): 9238-9248.
Song et al., 2008, "Transmission of avian influenza virus (H3N2) to dogs." Emerging Infectious Diseases, 14: 741-746.
Song et al., 2011, "Interspecies transmission of the canine influenza H3N2 virus to domestic cats in South Korea, 2010." The Journal of General Virology, 92: 2350-2355.
Song et al., 2015, "Canine susceptibility to human influenza viruses (A/pdm 09H1N1, A/H3N2 and B)." The Journal of General Virology, 96: 254-258.
Steel et al., 2009, "Live Attenuated Influenza Viruses Containing NS1 Truncations as Vaccine Candidates against H5N1 Highly Pathogenic Avian Influenza" J Virol 83:1742-1753.
Steidle et al., 2010, "Glycine 184 in Nonstructural Protein NS1 Determines the Virulence of Influenza A Virus Strain PR8 without Affecting the Host Interferon Response" J Viral, 84:12761-12770.
Subbarao et al., 1995, "Sequential addition of temperature-sensitive missense mutations into the PB2 gene of Influenza A transfectant viruses can effect an increase in temperature sensitivity and attenuation and permits the rational design of a genetically engineered live influenza a virus vaccine." Journal of Virology, 69(10): 5969-5977.
Suzuki et al., "Amino Acid Substitutions of PB1 of Avian Influenza Viruses Influence Pathogenicity and Transmissibility in Chickens," Journal of Virology, 88(19):11130-11139, 2014.
Talon et al., 2000, "Influenza A and B viruses expressing altered NS1 proteins: A vaccine approach" Proceedings of the National Academy of Sciences, 97:4309-4314.
Uraki et al., 2013, "A novel bivalent vaccine based on a PB2-knockout influenza virus protects mice from pandemic H1N1 and highly pathogenic H5N1 virus challenges." J Viral, 87: 7874-7881.
Varghese et al., 1992, "The structure of the complex between influenza virus neuraminidase and sialic acid, the viral receptor." Proteins, 14: -327-332.
Victor et al., 2012, "A replication-incompetent PB2-knockout influenza A virus vaccine vector." J Viral, 86(8): 4123-4128.
Vincent et al., 2007, "Efficacy of intranasal administration of a truncated NS1 modified live influenza virus vaccine in swine" Vaccine 25:7999-8009.
Voorhees et al., "Spread of Canine Influenza A9H3N2) Virus, United States," Emerging Infectious Diseases, 23 (12):1950-1957, 2017.
Wang et al., 2008, "Characterization of influenza virus variants with different sizes of the non-structural (NS) genes and their potential as a live influenza vaccine in poultry" Vaccine, 26:3580-3586.
Wong et al., 2013, "Traditional and new influenza vaccines." Clinical Microbiology Reviews, 26: 476-492.
Xiangxiang Sun et al, "Evidence of avian-like H9N2 influenza A virus among dogs in Guangxi, China", Infection, Genetics and Evolution, NL, (Dec. 1, 2013), vol. 20, doi:10.1016/j.meegid.2013.10.012, ISSN 1567-1348, pp. 471-475, XP055314508.
Yen et al., 2009, "Pandemic influenza as a current threat." Current topics in microbiology and immunology, 333: 3-24.
Yoon et al., 2005, "Influenza virus infection in racing greyhounds." Emerging Infectious Diseases, 11: 1974-1976.
Shinya et al. (Journal of General Virology. 2007; 88: 847-553).
Abdel-Moneim et al. (Archives of Virology. 2011; 156: 1257-1262).
International Search Report and Written Opinion, dated Sep. 27, 2017; recieved in PCT Application No. PCT/US2017/035630, 16 pages.

* cited by examiner

Nucleotide sequence of segment 1 (PB2) (in bold and underlined are indicted the nucleotide changes resulting in N265S amino acid change in PB2 protein) (SEQ ID NO: 1):

agcgaaagcaggtcaaatatattcaatatggagagaataaaagaactgagagatctgatgttacaatcccgcacccgcgagatactaacaaaaactac
tgtagaccacatggccataatcaagaaatacacatcaggaagacaagagaagaaccctgcacttaggatgaaatggatgatggcaatgaaataccca
atcacagcagataagaggataatggagatgattcctgagagaaatgaacagggacaaacccttggagcaaaacgaacgatgctggctcagaccgcg
taatggtatcacctctggcagtaacatggtggaataggaatggaccaacaacgaacacaattcattatccaaaagtctacaaaacttattttgaaaaggt
tgaaagattgaaacacggaacctttggccccgttcattttaggaatcaagtcaaaataagacgaagagttgatgtaaaccctggtcacgcggacctcag
tgctaaagaagcacaagatgtgatcatggaagttgttttcccaaatgaggtgggagcccgaattctaacatcggaatcacaactaacaataaccaagga
gaaaaaggaagaacttcaggactgcaaaattgctcccttgatggtagcatacatgctagaaagagagttggtccgaaaaacaaggttcctcccagtagt
aggcggaacaagcagtatatacattgaagtgttgcatctgactcagggaacatgctgggagcaaatgtacaccccaggaggagaagttagaaacgatg
atattgatcaaagtttaattattgcagcccgg<u>tca</u>atagtgagaagagcgacagtatcagcagatccactagcatccctactggaaatgtgccacagtac
acaaattggtggaacaaggatgatagacatccttaagcagaacccaacagaggaacaagctgtggatatatgcaaagcagcaatgggattgagaatt
agctcatcattcagctttggtggattcaccttcaaaaggacaagtggatcatcagtcaagagagaagaagaaatgcttacgggcaaccttcaaacattg
aaaataagagtgcatgagggctatgaagaattcacaatggtcggaagaagagcaacagccattatcagaaaggcaaccagaagattgattcaactga
tagtaagtggaaaagatgaacaatcaattgctgaagcaataattgtagccatggtgttttcgcaagaagattgcatgataaaagcagttcgaggcgattt
gaactttgttaatagagcaaatcagcgtttaaaccccatgcatcaactcttgaggcatttccaaaaagatgcaaaagtgcttttccaaaattggggaattg
aacccatcgacaatgtaatgggaatgattggaatactgcctgacatgaccccaagcactgaaatgtcattgagaggagtgagagtcagcaaaatggga
gtggatgagtactccagcactgagagagtggtggtgagcattgaccgtttttaagagttcgggatcaaaggggaaacatactactgtcccctgaagaag
tcagtgaaacacaaggaacggaaaagctgacaataatttattcgtcatcaatgatgtgggagattaatggtcccgaatcagtgttggtcaatacttatca
atggatcatcagaaactgggaaaatgtaaaaattcagtggtcacaggaccccacaatgttatacaataagatagaatttgagccattccaatccctggtc
cctagggccaccagaagccaatacagcggttttgtaagaaccctgtttcagcaaatgcgagatgtacttggaacatttgatactgctcaaataataaaac
tcctcccttttgccgctgctcctccggaacagagtaggatgcagttctcttctttgactgttaatgtaagaggttcgggaatgaggatacttgtaagaggca
attccccagtgttcaactacaataaagccactaaaggctcacagtcctcggaaaagatgcgggtgcgcttactgaggacccagatgaaggtacggctg
gagtagaatccgctgttctaagagggtttctcatcttaggtaaagaaaacaagagatatggcccagcactaagcatcaatgaacttagcaaacttgcaa
aaggggagaaagccaatgtactaattgggcaaggggacatagtgttggtaatgaaacggaaacgtgactctagcatacttactgacagccagacagcg
accaaaaggattcggatggccatcaattagtgttaaattgtttaaaaacgaccttgtttctact

Figure 13A

Amino acid sequence of PB2 LACIV protein (in bold and underlined is indicated the amino acid change N265S) (SEQ ID NO: 3):

MERIKELRDLMLQSRTREILTKTTVDHMAIIKKYTSGRQEKNPALRMKWMMAMKYPITADKRIME
MIPERNEQGQTLWSKTNDAGSDRVMVSPLAVTWWNRNGPTTNTIHYPKVYKTYFEKVERLKHGTF
GPVHFRNQVKIRRRVDVNPGHADLSAKEAQDVIMEVVFPNEVGARILTSESQLTITKEKKEELQD
CKIAPLMVAYMLERELVRKTRFLPVVGGTSSIYIEVLHLTQGTCWEQMYTPGGEVRNDDIDQSLI
IAAR<u>S</u>IVRRATVSADPLASLLEMCHSTQIGGTRMIDILKQNPTEEQAVDICKAAMGLRISSSFSF
GGFTFKRTSGSSVKREEEMLTGNLQTLKIRVHEGYEEFTMVGRRATAIIRKATRRLIQLIVSGKD
EQSIAEAIIVAMVFSQEDCMIKAVRGDLNFVNRANQRLNPMHQLLRHFQKDAKVLFQNWGIEPID
NVMGMIGILPDMTPSTEMSLRGVRVSKMGVDEYSSTERVVVSIDRFLRVRDQRGNILLSPEEVSE
TQGTEKLTIIYSSSMMWEINGPESVLVNTYQWIIRNWENVKIQWSQDPTMLYNKIEFEPFQSLVP
RATRSQYSGFVRTLFQQMRDVLGTFDTAQIIKLLPFAAAPPEQSRMQFSSLTVNVRGSGMRILVR
GNSPVFNYNKATKRLTVLGKDAGALTEDPDEGTAGVESAVLRGFLILGKENKRYGPALSINELSK
LAKGEKANVLIGQGDIVLVMKRKRDSSILTDSQTATKRIRMAIN

Figure 13B

Nucleotide sequence of segment 2 (PB1) (in bold and underlined are indicted the nucleotide changes resulting in K391E, E581G, and A661T amino acid changes in PB1 protein) (SEQ ID NO: 2):

agcgaaagcaggcaaaccatttgaatggatgtcaacccgactctacttttcttaaaggtgccagcgcaaaatgctataagcacaacattcccttata
ctggagatcctccctacagtcatggaacagggacaggatacaccatggatactgtcaacagaacgcaccaatattcagaaaagggaaatggat
aacaaacactgagattggagcaccacaacttaatccaatcgatggaccacttcctgaagacaatgaaccaagtgggtacgcccaaacagattgtg
tattggaagcaatggctttccttgaagaatcccatcccggaatctttgaaaattcgtgtcttgaaacaatggaggtgattcagcagacaagagtgga
caaactaacacaaggccgacaaacttatgattggaccttgaataggaatcaacctgccgcaacagcacttgctaatacgattgaagtattcagatc
aaatggtctgacttccaatgaatcggggagattgatagacttcctcaaagatgtcatggagtccatgaacaaggaagaaatggaaataacaacac
acttccaacggaagagaagagtaagagacaacatgacaaagagaatgataacacagagaaccatagggaagaaaaaacaacgattaaacag
aaagagctatctgatcagaacattaaccctaaacacaatgaccaaggacgctgagagagggaaattgaaacgacgagcaatcgctaccccaggg
atgcagataagaggatttgtatattttgttgaaacactagctcgaagaatatgtgaaaagcttgaacaatcaggattgccagttggcggtaatgaga
aaaaagccaaactggctaatgtcgtcagaaaaatgatgactaattcccaagacactgaactctccttcaccatcactggggacaataccaaatgga
atgaaaatcagaacccacgcatattcctggcaatgatcacatacataactagaaatcagccagaatggttcagaaatgttctaaacattgcaccga
ttatgttctcaaataaaatggcaagactggggaaaggatatatgtttgaaagcaaaagtatgaaattgagaactcaaataccagcagaaatgcta
gcgagcattgacctaaaatatttcaatgattcaacaaaaaagaaaattgaagagatacgaccactcttggttaacgggactgcttcactgagtcctg
gcatgatgatgggaatgttcaacatgttgagcactgtgctgggtgtatccatattaaacctgggccagaggaaatatacaaaaaccacatactggt
gggatggtctgcaatcatcagatgactttgctttgatagtgaatgcgcctaatcatgaaggaatacaagctggagtagacagattctatagaacttg
caaactggtcggatcaacatgagcaaaaagaagtcctacataaatagaactggaacattcgaattcacaagctttttctaccggtatggttttgta
gccaatttcagcatggaactacccagttttggggtttccggaataaatgaatctgcagacatgagcattggagtgacaatcatcaaaaacaacatg
ataaataatgatctcggtcctgccacggcacaaatggcactccaactcttcattaaggattatcggtacacataccggtgccatagaggtgataccc
agatacaaaccagaagatcttttgagttgaagaaactttgggggcagactcaatcaaagactggtctactgatatcagatgggggtccaaacctat
ataacatcagaaacctacacatcccggaagtctgtttaaagtgggagctaatggatgaagattataaggggaggctatgcaatccattgaatccttt
cgttagtcacaaagaaattgaatcagtcaacagtgcagtagtaatgcctgcgcatggccctgccaaaagcatggagtatgatgctgttactacaac
acattcttggatccccaagaggaaccggtccatattgaacacaagccaaaggggaatactcgaagatgagcatatgtatcagaaatgctgcaacc
tgtttgaaaaattcttcccaagcagctcatacagaagaccagtcggaatttctagtatggttgaggccatggtatccagggcccgcattgatgcacg
aattgacttcgaatctggacggataaagaaggatgagttcgctgagatcatgaagatctgttccaccattgaagagctcaaacggcaaaaatagtg
aatttagcttgatcttcatgaaaaaatgccttgtttctact

Figure 14A

Amino acid sequence of PB1 LACIV protein (in red is indicated the amino acid changes K391E, E581G, A661T) (SEQ ID NO: 4):

MDVNPTLLFLKVPAQNAISTTFPYTGDPPYSHGTGTGYTMDTVNRTHQYSEKGKWITNTEIG
APQLNPIDGPLPEDNEPSGYAQTDCVLEAMAFLEESHPGIFENSCLETMEVIQQTRVDKLTQ
GRQTYDWTLNRNQPAATALANTIEVFRSNGLTSNESGRLIDFLKDVMESMNKEEMEITTHFQ
RKRRVRDNMTKRMITQRTIGKKKQRLNRKSYLIRTLTLNTMTKDAERGKLKRRAIATPGMQI
RGFVYFVETLARRICEKLEQSGLPVGGNEKKAKLANVVRKMMTNSQDTELSFTITGDNTKWN
ENQNPRIFLAMITYITRNQPEWFRNVLNIAPIMFSNKMARLGKGYMFESKSMKLRTQIPAEM
LASIDLKYFNDSTKKKIEEIRPLLVNGTASLSPGMMMGMFNMLSTVLGVSILNLGQRKYTKT
TYWWDGLQSSDDFALIVNAPNHEGIQAGVDRFYRTCKLVGINMSKKKSYINRTGTFEFTSFF
YRYGFVANFSMELPSFGVSGINESADMSIGVTIIKNNMINNDLGPATAQMALQLFIKDYRYT
YRCHRGDTQIQTRRSFELKKLWGQTQSKTGLLISDGGPNLYNIRNLHIPEVCLKWELMDEDY
KGRLCNPLNPFVSHKEIESVNSAVVMPAHGPAKSMEYDAVTTTHSWIPKRNRSILNTSQRGI
LEDEHMYQKCCNLFEKFFPSSSYRRPVGISSMVEAMVSRARIDARIDFESGRIKKDEFAEIM
KICSTIEELKRQK

Figure 14B

SEQUENCE LISTING

```
<160> NUMBER OF SEQ ID NOS: 26

<210> SEQ ID NO 1
<211> LENGTH: 2341
<212> TYPE: DNA
<213> ORGANISM: Artificial Sequence
<220> FEATURE:
<223> OTHER INFORMATION: Chemically Synthesized

<400> SEQUENCE: 1

agcgaaagca ggtcaaatat attcaatatg gagagaataa aagaactgag agatctgatg     60

ttacaatccc gcacccgcga gatactaaca aaaactactg tagaccacat ggccataatc    120

aagaaataca catcaggaag acaagagaag aaccctgcac ttaggatgaa atggatgatg    180

gcaatgaaat acccaatcac agcagataag aggataatgg agatgattcc tgagagaaat    240

gaacagggac aaaccctttg gagcaaaacg aacgatgctg gctcagaccg cgtaatggta    300

tcacctctgg cagtaacatg gtggaatagg aatggaccaa caacgaacac aattcattat    360

ccaaaagtct acaaaactta ttttgaaaag gttgaaagat tgaaacacgg aacctttggc    420

cccgttcatt ttaggaatca agtcaaaata agacgaagag ttgatgtaaa ccctggtcac    480

gcggacctca gtgctaaaga agcacaagat gtgatcatgg aagttgtttt cccaaatgag    540

gtgggagccc gaattctaac atcggaatca caactaacaa taaccaagga gaaaaaggaa    600

gaacttcagg actgcaaaat tgctcccttg atggtagcat acatgctaga aagagagttg    660

gtccgaaaaa caaggttcct cccagtagta ggcggaacaa gcagtatata cattgaagtg    720

ttgcatctga ctcagggaac atgctgggag caaatgtaca ccccaggagg agaagttaga    780

aacgatgata ttgatcaaag tttaattatt gcagcccggt caatagtgag aagagcgaca    840

gtatcagcag atccactagc atccctactg gaaatgtgcc acagtacaca aattggtgga    900

acaaggatga tagacatcct taagcagaac ccaacagagg aacaagctgt ggatatatgc    960

aaagcagcaa tgggattgag aattagctca tcattcagct ttggtggatt caccttcaaa   1020

aggacaagtg gatcatcagt caagagagaa gaagaaatgc ttacgggcaa ccttcaaaca   1080

ttgaaaataa gagtgcatga gggctatgaa gaattcacaa tggtcggaag aagagcaaca   1140

gccattatca gaaaggcaac cagaagattg attcaactga tagtaagtgg aaaagatgaa   1200

caatcaattg ctgaagcaat aattgtagcc atggtgtttt cgcaagaaga ttgcatgata   1260

aaagcagttc gaggcgattt gaactttgtt aatagagcaa atcagcgttt aaaccccatg   1320

catcaactct tgaggcattt ccaaaaagat gcaaaagtgc ttttccaaaa ttggggaatt   1380

gaacccatcg acaatgtaat gggaatgatt ggaatactgc ctgacatgac cccaagcact   1440

gaaatgtcat tgagaggagt gagagtcagc aaaatgggag tggatgagta ctccagcact   1500

gagagagtgg tggtgagcat tgaccgtttt ttaagagttc gggatcaaag gggaaacata   1560

ctactgtccc ctgaagaagt cagtgaaaca caaggaacgg aaaagctgac aataattttat  1620

tcgtcatcaa tgatgtggga gattaatggt cccgaatcag tgttggtcaa tacttatcaa   1680
```

```
tggatcatca gaaactggga aaatgtaaaa attcagtggt cacaggaccc cacaatgtta   1740

tacaataaga tagaatttga gccattccaa tccctggtcc ctagggccac cagaagccaa   1800

tacagcggtt ttgtaagaac cctgtttcag caaatgcgag atgtacttgg aacatttgat   1860

actgctcaaa taataaaact cctccctttt gccgctgctc ctccggaaca gagtaggatg   1920

cagttctctt ctttgactgt taatgtaaga ggttcgggaa tgaggatact tgtaagaggc   1980

aattccccag tgttcaacta caataaagcc actaaaaggc tcacagtcct cggaaaagat   2040

gcgggtgcgc ttactgagga cccagatgaa ggtacggctg gagtagaatc cgctgttcta   2100

agagggtttc tcatcttagg taaagaaaac aagagatatg gcccagcact aagcatcaat   2160

gaacttagca aacttgcaaa aggggagaaa gccaatgtac taattgggca aggggacata   2220

gtgttggtaa tgaaacggaa acgtgactct agcatactta ctgacagcca gacagcgacc   2280

aaaaggattc ggatggccat caattagtgt taaattgttt aaaaacgacc ttgtttctac   2340

t                                                                     2341
```

```
<210> SEQ ID NO 2
<211> LENGTH: 2341
<212> TYPE: DNA
<213> ORGANISM: Artificial Sequence
<220> FEATURE:
<223> OTHER INFORMATION: Chemically Synthesized

<400> SEQUENCE: 2

agcgaaagca ggcaaaccat ttgaatggat gtcaacccga ctctactttt cttaaaggtg     60

ccagcgcaaa atgctataag cacaacattc ccttatactg gagatcctcc ctacagtcat    120

ggaacaggga caggatacac catggatact gtcaacagaa cgcaccaata ttcagaaaaa    180

gggaaatgga taacaaacac tgagattgga gcaccacaac ttaatccaat cgatggacca    240

cttcctgaag acaatgaacc aagtgggtac gcccaaacag attgtgtatt ggaagcaatg    300

gctttccttg aagaatccca tcccggaatc tttgaaaatt cgtgtcttga aacaatggag    360

gtgattcagc agacaagagt ggacaaacta acacaaggcc gacaaactta tgattggacc    420

ttgaatagga atcaacctgc cgcaacagca cttgctaata cgattgaagt attcagatca    480

aatggtctga cttccaatga atcggggaga ttgatagact tcctcaaaga tgtcatggag    540

tccatgaaca aggaagaaat ggaaataaca acacacttcc aacggaagag aagagtaaga    600

gacaacatga caaagagaat gataacacag agaaccatag ggaagaaaaa acaacgatta    660

aacagaaaga gctatctgat cagaacatta accctaaaca caatgaccaa ggacgctgag    720

agagggaaat tgaaacgacg agcaatcgct accccaggga tgcagataag aggatttgta    780

tattttgttg aaacactagc tcgaagaata tgtgaaaagc ttgaacaatc aggattgcca    840

gttggcggta atgagaaaaa agccaaactg gctaatgtcg tcagaaaaat gatgactaat    900

tcccaagaca ctgaactctc cttcaccatc actggggaca ataccaaatg gaatgaaaat    960

cagaacccac gcatattcct ggcaatgatc acatacataa ctagaaatca gccagaatgg   1020

ttcagaaatg ttctaaacat tgcaccgatt atgttctcaa ataaaatggc aagactgggg   1080

aaaggatata tgtttgaaag caaaagtatg aaattgagaa ctcaaatacc agcagaaatg   1140

ctagcgagca ttgacctaaa atatttcaat gattcaacaa aaaagaaaat tgaagagata   1200

cgaccactct tggttaacgg gactgcttca ctgagtcctg gcatgatgat gggaatgttc   1260

aacatgttga gcactgtgct gggtgtatcc atattaaacc tgggccagag gaaatataca   1320
```

```
aaaaccacat actggtggga tggtctgcaa tcatcagatg actttgcttt gatagtgaat   1380

gcgcctaatc atgaaggaat acaagctgga gtagacagat tctatagaac ttgcaaactg   1440

gtcgggatca acatgagcaa aaagaagtcc tacataaata gaactggaac attcgaattc   1500

acaagctttt tctaccggta tggttttgta gccaatttca gcatggaact acccagtttt   1560

ggggtttccg gaataaatga atctgcagac atgagcattg gagtgacaat catcaaaaac   1620

aacatgataa ataatgatct cggtcctgcc acggcacaaa tggcactcca actcttcatt   1680

aaggattatc ggtacacata ccggtgccat agaggtgata cccagataca aaccagaaga   1740

tcttttgagt tgaagaaact ttgggggcag actcaatcaa agactggtct actgatatca   1800

gatgggggtc caaacctata taacatcaga aacctacaca tcccggaagt ctgtttaaag   1860

tgggagctaa tggatgaaga ttataagggg aggctatgca atccattgaa tcctttcgtt   1920

agtcacaaag aaattgaatc agtcaacagt gcagtagtaa tgcctgcgca tggccctgcc   1980

aaaagcatgg agtatgatgc tgttactaca acacattctt ggatccccaa gaggaaccgg   2040

tccatattga acacaagcca aaggggaata ctcgaagatg agcatatgta tcagaaatgc   2100

tgcaacctgt ttgaaaaatt cttcccaagc agctcataca gaagaccagt cggaatttct   2160

agtatggttg aggccatggt atccagggcc cgcattgatg cacgaattga cttcgaatct   2220

ggacggataa agaaggatga gttcgctgag atcatgaaga tctgttccac cattgaagag   2280

ctcaaacggc aaaaatagtg aatttagctt gatcttcatg aaaaaatgcc ttgtttctac   2340

t                                                                   2341
```

<210> SEQ ID NO 3
<211> LENGTH: 759
<212> TYPE: PRT
<213> ORGANISM: Artificial Sequence
<220> FEATURE:
<223> OTHER INFORMATION: Chemically Synthesized

<400> SEQUENCE: 3

```
Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175
```

-continued

```
Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Val Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Ser Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Thr Arg Met Ile Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Ile Arg Lys Ala Thr Arg Arg Leu Ile Gln Leu
    370                 375                 380

Ile Val Ser Gly Lys Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Asn Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
```

```
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Ile Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 4
<211> LENGTH: 757
<212> TYPE: PRT
<213> ORGANISM: Artificial Sequence
<220> FEATURE:
<223> OTHER INFORMATION: Chemically Synthesized

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Ile Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Ile Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Ile Thr Gln Arg Thr Ile Gly Lys Lys
```

-continued

```
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Asn Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Glu Ile Arg Pro Leu Leu Val Asn Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Ile Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Gly Gln Thr Gln Ser Lys Thr Gly Leu Leu Ile Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620
```

Cys Asn Pro Leu Asn Pro Phe Val Ser His Lys Glu Ile Glu Ser Val
625 630 635 640

Asn Ser Ala Val Val Met Pro Ala His Gly Pro Ala Lys Ser Met Glu
645 650 655

Tyr Asp Ala Val Thr Thr Thr His Ser Trp Ile Pro Lys Arg Asn Arg
660 665 670

Ser Ile Leu Asn Thr Ser Gln Arg Gly Ile Leu Glu Asp Glu His Met
675 680 685

Tyr Gln Lys Cys Cys Asn Leu Phe Glu Lys Phe Phe Pro Ser Ser Ser
690 695 700

Tyr Arg Arg Pro Val Gly Ile Ser Ser Met Val Glu Ala Met Val Ser
705 710 715 720

Arg Ala Arg Ile Asp Ala Arg Ile Asp Phe Glu Ser Gly Arg Ile Lys
725 730 735

Lys Asp Glu Phe Ala Glu Ile Met Lys Ile Cys Ser Thr Ile Glu Glu
740 745 750

Leu Lys Arg Gln Lys
755

<210> SEQ ID NO 5
<211> LENGTH: 2341
<212> TYPE: DNA
<213> ORGANISM: Influenza A virus (H3N8)

<400> SEQUENCE: 5
agcgaaagca ggtcaaatat attcaatatg gagagaataa aagaactgag agatctgatg 60
ttacaatccc gcacccgcga gatactaaca aaaactactg tagaccacat ggccataatc 120
aagaaataca catcaggaag acaagagaag aaccctgcac ttaggatgaa atggatgatg 180
gcaatgaaat acccaatcac agcagataag aggataatgg agatgattcc tgagagaaat 240
gaacagggac aaaccctttg gagcaaaacg aacgatgctg gctcagaccg cgtaatggta 300
tcacctctgg cagtaacatg gtggaatagg aatggaccaa caacgaacac aattcattat 360
ccaaaagtct acaaaactta ttttgaaaag gttgaaagat tgaaacacgg aacctttggc 420
cccgttcatt ttaggaatca agtcaaaata agacgaagag ttgatgtaaa ccctggtcac 480
gcggacctca gtgctaaaga agcacaagat gtgatcatgg aagttgtttt cccaaatgag 540
gtgggagccc gaattctaac atcggaatca caactaacaa taaccaagga gaaaaaggaa 600
gaacttcagg actgcaaaat tgctcccttg atggtagcat acatgctaga aagagagttg 660
gtccgaaaaa caaggttcct cccagtagta ggcggaacaa gcagtatata cattgaagtg 720
ttgcatctga ctcagggaac atgctgggag caaatgtaca ccccaggagg agaagttaga 780
aacgatgata ttgatcaaag tttaattatt gcagcccgga acatagtgag aagagcgaca 840
gtatcagcag atccactagc atccctactg gaaatgtgcc acagtacaca aattggtgga 900
acaaggatga tagacatcct taagcagaac ccaacagagg aacaagctgt ggatatatgc 960
aaagcagcaa tgggattgag aattagctca tcattcagct ttggtggatt caccttcaaa 1020
aggacaagtg gatcatcagt caagagagaa gaagaaatgc ttacgggcaa ccttcaaaca 1080
ttgaaaataa gagtgcatga gggctatgaa gaattcacaa tggtcggaag aagagcaaca 1140
gccattatca gaaaggcaac cagaagattg attcaactga tagtaagtgg aaaagatgaa 1200
caatcaattg ctgaagcaat aattgtagcc atggtgtttt cgcaagaaga ttgcatgata 1260
aaagcagttc gaggcgattt gaactttgtt aatagagcaa atcagcgttt aaaccccatg 1320

-continued

```
catcaactct tgaggcattt ccaaaaagat gcaaaagtgc ttttccaaaa ttggggaatt   1380

gaacccatcg acaatgtaat gggaatgatt ggaatactgc ctgacatgac cccaagcact   1440

gaaatgtcat tgagaggagt gagagtcagc aaaatgggag tggatgagta ctccagcact   1500

gagagagtgg tggtgagcat tgaccgtttt ttaagagttc gggatcaaag gggaaacata   1560

ctactgtccc ctgaagaagt cagtgaaaca caaggaacgg aaaagctgac aataatttat   1620

tcgtcatcaa tgatgtggga gattaatggt cccgaatcag tgttggtcaa tacttatcaa   1680

tggatcatca gaaactggga aaatgtaaaa attcagtggt cacaggaccc cacaatgtta   1740

tacaataaga tagaatttga gccattccaa tccctggtcc ctagggccac cagaagccaa   1800

tacagcggtt ttgtaagaac cctgtttcag caaatgcgag atgtacttgg aacatttgat   1860

actgctcaaa taataaaact cctccctttt gccgctgctc ctccggaaca gagtaggatg   1920

cagttctctt ctttgactgt taatgtaaga ggttcgggaa tgaggatact tgtaagaggc   1980

aattccccag tgttcaacta caataaagcc actaaaaggc tcacagtcct cggaaaagat   2040

gcgggtgcgc ttactgagga cccagatgaa ggtacggctg gagtagaatc cgctgttcta   2100

agagggtttc tcatcttagg taaagaaaac aagagatatg gcccagcact aagcatcaat   2160

gaacttagca aacttgcaaa aggggagaaa gccaatgtac taattgggca aggggacata   2220

gtgttggtaa tgaaacggaa acgtgactct agcatactta ctgacagcca gacagcgacc   2280

aaaaggattc ggatggccat caattagtgt taaattgttt aaaaacgacc ttgtttctac   2340

t                                                                   2341
```

```
<210> SEQ ID NO 6
<211> LENGTH: 759
<212> TYPE: PRT
<213> ORGANISM: Influenza A virus (H3N8)

<400> SEQUENCE: 6

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
```

-continued

```
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Val Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Thr Arg Met Ile Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Ile Arg Lys Ala Thr Arg Arg Leu Ile Gln Leu
    370                 375                 380

Ile Val Ser Gly Lys Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Asn Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605
```

```
Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Ile Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 7
<211> LENGTH: 2341
<212> TYPE: DNA
<213> ORGANISM: Influenza A virus (H3N8)

<400> SEQUENCE: 7

agcgaaagca ggcaaaccat ttgaatggat gtcaacccga ctctactttt cttaaaggtg     60

ccagcgcaaa atgctataag cacaacattc ccttatactg gagatcctcc ctacagtcat    120

ggaacaggga caggatacac catggatact gtcaacagaa cgcaccaata ttcagaaaaa    180

gggaaatgga taacaaacac tgagattgga gcaccacaac ttaatccaat cgatggacca    240

cttcctgaag acaatgaacc aagtgggtac gcccaaacag attgtgtatt ggaagcaatg    300

gctttccttg aagaatccca tcccggaatc tttgaaaatt cgtgtcttga aacaatggag    360

gtgattcagc agacaagagt ggacaaacta acacaaggcc gacaaactta tgattggacc    420

ttgaatagga atcaacctgc cgcaacagca cttgctaata cgattgaagt attcagatca    480

aatggtctga cttccaatga atcggggaga ttgatagact tcctcaaaga tgtcatggag    540

tccatgaaca aggaagaaat ggaaataaca acacacttcc aacggaagag aagagtaaga    600

gacaacatga caaagagaat gataacacag agaaccatag ggaagaaaaa acaacgatta    660

aacagaaaga gctatctgat cagaacatta accctaaaca caatgaccaa ggacgctgag    720

agagggaaat tgaaacgacg agcaatcgct accccaggga tgcagataag aggatttgta    780

tattttgttg aaacactagc tcgaagaata tgtgaaaagc ttgaacaatc aggattgcca    840

gttggcggta atgagaaaaa agccaaactg gctaatgtcg tcagaaaaat gatgactaat    900

tcccaagaca ctgaactctc cttcaccatc actggggaca ataccaaatg gaatgaaaat    960

cagaacccac gcatattcct ggcaatgatc acatacataa ctagaaatca gccagaatgg   1020

ttcagaaatg ttctaaacat tgcaccgatt atgttctcaa ataaaatggc aagactgggg   1080

aaaggatata tgtttgaaag caaaagtatg aaattgagaa ctcaaatacc agcagaaatg   1140

ctagcgagca ttgacctaaa atatttcaat gattcaacaa aaaagaaaat tgaaaagata   1200
```

-continued

```
cgaccactct tggttaacgg gactgcttca ctgagtcctg gcatgatgat gggaatgttc   1260

aacatgttga gcactgtgct gggtgtatcc atattaaacc tgggccagag gaaatataca   1320

aaaaccacat actggtggga tggtctgcaa tcatcagatg actttgcttt gatagtgaat   1380

gcgcctaatc atgaaggaat acaagctgga gtagacagat tctatagaac ttgcaaactg   1440

gtcgggatca acatgagcaa aaagaagtcc tacataaata gaactggaac attcgaattc   1500

acaagctttt tctaccggta tggttttgta gccaatttca gcatggaact acccagtttt   1560

ggggtttccg gaataaatga atctgcagac atgagcattg gagtgacaat catcaaaaac   1620

aacatgataa ataatgatct cggtcctgcc acggcacaaa tggcactcca actcttcatt   1680

aaggattatc ggtacacata ccggtgccat agaggtgata cccagataca aaccagaaga   1740

tcttttgagt tgaagaaact ttgggaacag actcaatcaa agactggtct actgatatca   1800

gatgggggtc caaacctata taacatcaga aacctacaca tcccggaagt ctgtttaaag   1860

tgggagctaa tggatgaaga ttataagggg aggctatgca atccattgaa tcctttcgtt   1920

agtcacaaag aaattgaatc agtcaacagt gcagtagtaa tgcctgcgca tggccctgcc   1980

aaaagcatgg agtatgatgc tgttgcaaca acacattctt ggatccccaa gaggaaccgg   2040

tccatattga acacaagcca aaggggaata ctcgaagatg agcatatgta tcagaaatgc   2100

tgcaacctgt ttgaaaaatt cttcccaagc agctcataca gaagaccagt cggaatttct   2160

agtatggttg aggccatggt atccagggcc cgcattgatg cacgaattga cttcgaatct   2220

ggacggataa agaaggatga gttcgctgag atcatgaaga tctgttccac cattgaagag   2280

ctcaaacggc aaaaatagtg aatttagctt gatcttcatg aaaaaatgcc ttgtttctac   2340

t                                                                   2341
```

<210> SEQ ID NO 8
<211> LENGTH: 757
<212> TYPE: PRT
<213> ORGANISM: Influenza A virus (H3N8)

<400> SEQUENCE: 8

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Ile Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Ile Asp Phe Leu Lys Asp Val Met Glu Ser Met Asn Lys
```

-continued

```
                165                 170                 175

Glu Glu Met Glu Ile Thr Thr His Phe Gln Arg Lys Arg Arg Val Arg
            180                 185                 190

Asp Asn Met Thr Lys Arg Met Ile Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Asn Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asn Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Ile Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Gln Ser Lys Thr Gly Leu Leu Ile Ser
            580                 585                 590
```

-continued

```
Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu His Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Lys Arg Gln Lys
        755


<210> SEQ ID NO 9
<211> LENGTH: 2233
<212> TYPE: DNA
<213> ORGANISM: Influenza A virus (H3N8)

<400> SEQUENCE: 9

agcgaaagca ggtactgatc caaaatggaa gactttgtgc gacagtgctt caatccaatg      60

atcgtcgagc ttgcggaaaa ggcaatgaaa gaatatggag agaacccgaa aatcgaaaca     120

aacaaatttg cagcaatatg cactcacttg gaagtctgct tcatgtactc ggatttccac     180

tttataaatg aactgggtga gtcagtggtc atagagtctg gtgacccaaa tgctcttttg     240

aaacacagat ttgaaatcat tgaggggaga gatcgaacaa tggcatggac agtagtaaac     300

agcatctgca acaccacaag agctgaaaaa cctaaatttc ttccagattt atacgactat     360

aaggagaaca gatttgttga aattggtgtg acaaggagag aagttcacat atactacctg     420

gagaaggcca acaaaataaa gtctgagaaa acacatatcc acatcttctc atttacagga     480

gaggaaatgg ctacaaaagc ggactatact cttgatgaag agagtagagc caggatcaag     540

accagactat tcactataag acaagaaatg gccagtagag gcctctggga ttcctttcgt     600

cagtccgaga gaggcgaaga gacaattgaa gaaagatttg aaatcacagg gacgatgcgc     660

aagcttgcca attacagtct cccaccgaac ttctccagcc ttgaaaattt tagagtttat     720

gtagatggat tcgaaccgaa cggctgcatt gagagtaagc tttctcaaat gtccaaagaa     780

gtaaatgcca aaatcgaacc attttcaaag acaacacccc gaccactcaa aatgcctggt     840

ggtccaccct gccatcagcg atccaaattc ttgctaatgg atgctctgaa attgagcatt     900

gaagacccaa gtcacgaggg agaagggata ccactatatg atgcaatcaa atgcatgaaa     960

actttctttg gatggaaaga acccagtatt gttaaaccac ataaaaaggg tataaacccg    1020

aactatctcc aaacttggaa gcaagtatta gaagaaatac aagacattga gaacgaagaa    1080

aagacccccca aaaccaagaa tatgaaaaaa acaagccaat taaaatgggc actaggtgaa    1140
```

aatatggcac cagagaaagt ggattttgag gattgtaaag acatcaatga tttaaaacaa 1200
tatgacagtg atgagccaga agcaaggtct cttgcaagtt ggattcaaag tgagttcaac 1260
aaggcttgtg agctgacaga ttcaagctgg atagagctcg atgaaattgg ggaggatgtc 1320
gccccaatag aatacattgc gagcatgagg agagactatt ttactgctga gatttcccat 1380
tgtagagcaa cagaatatat aatgaaagga gtatacatca acactgctct actcaatgca 1440
tcctgtgctg cgatggatga atttcaattg attccgatga taagtaaatg caggaccaaa 1500
gaagggagaa ggaaaacaaa tttatatgga ttcataataa agggaaggtc ccatttaaga 1560
aatgatactg acgtggtgaa ctttgtaagt atggaatttt ctctcactga tccaagattt 1620
gagccacaca aatgggaaaa atactgcgtt ctagaaattg gagacatgct tctaagaact 1680
gctgtaggtc aagtgtcaag acccatgttt ttatatgtaa ggacaaatgg aacctctaaa 1740
attaaaatga aatggggaat ggaaatgagg cgctgcctcc ttcagtctct acaacagatt 1800
gaaagcatga tcgaagctga gtcctcagtc aaagaaaagg acatgaccaa agaatttttt 1860
gagaacaaat cagagacatg gcctatagga gagtccccca aaggagtgga agaaggctca 1920
atcgggaagg tttgcaggac cttattagca aaatctgtgt ttaacagttt atatgcatct 1980
ccacaactgg aaggattttc agctgaatct aggaaattac ttctcattgt tcaggctctt 2040
agagatgacc tggaacctgg aacctttgat attgggggt tatatgaatc aattgaggag 2100
tgcctgatta atgatccctg ggttttgctt aatgcatctt ggttcaactc cttcctcaca 2160
catgcactga agtagttgtg gcaatgctac tatttgctat ccatactgtc caaaaaagta 2220
ccttgtttct act 2233

<210> SEQ ID NO 10
<211> LENGTH: 716
<212> TYPE: PRT
<213> ORGANISM: Influenza A virus (H3N8)

<400> SEQUENCE: 10

Met Glu Asp Phe Val Arg Gln Cys Phe Asn Pro Met Ile Val Glu Leu
1 5 10 15

Ala Glu Lys Ala Met Lys Glu Tyr Gly Glu Asn Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Leu Gly Glu Ser Val Val Ile Glu
50 55 60

Ser Gly Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

Thr Thr Arg Ala Glu Lys Pro Lys Phe Leu Pro Asp Leu Tyr Asp Tyr
100 105 110

Lys Glu Asn Arg Phe Val Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

```
Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Lys
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Ile Val Lys Pro His Lys Lys Gly Ile Asn Pro Asn Tyr Leu Gln
                325                 330                 335

Thr Trp Lys Gln Val Leu Glu Glu Ile Gln Asp Ile Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu Pro Glu Ala
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asp Tyr Phe Thr Ala
        435                 440                 445

Glu Ile Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
    530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590
```

-continued

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Lys Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asp Leu Glu Pro Gly Thr Phe Asp Ile Gly Gly Leu Tyr Glu
675 680 685

Ser Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 11
<211> LENGTH: 1762
<212> TYPE: DNA
<213> ORGANISM: Influenza A virus (H3N8)

<400> SEQUENCE: 11
agcaaaagca ggggatattt ctttcaatca tgaaaacaac cattatttta atactactga 60
cccattgggc ctacagtcaa aacccaatca gtggcaataa cacagccaca ctgtgtctgg 120
gacaccatgc agtagcaaat ggaacattgg taaaaacaat gagtgatgat caaattgagg 180
tgacaaatgc tacagaatta gttcagagca tttcaatggg gaaaatatgc aacaaatcat 240
atagagttct agatggaaga aattgcacat taatagatgc aatgctagga gacccccagt 300
gtgacgcctt tcagtatgag agttgggacc tctttataga aagaagcaac gctttcagca 360
attgctaccc atatgacatc cctgactatg catcgctccg atccattgta gcatcctcag 420
gaacagtgga attcacagca gagggattca catggacagg tgtcactcaa aacggaagaa 480
gtggagcctg caaaagggga tcagccgata gtttctttag ccgactgaat tggctaacaa 540
aatctggaag ctcttacccc acattgaatg tgacaatgcc taacaataaa aatttcgaca 600
agctatacat ctgggggatt catcacccga gctcgaatca agagcagaca aaattgtaca 660
tccaagaatc aggacgagta acagtctcaa caaaaagaag tcaacaaaca ataatccctc 720
acatcggatc tagaccgttg atcagaggtc aatcaggcag gataagcata tactggacca 780
ttgtaaaacc tggagatatc ctaatgataa acagtaatgg caacttagtt gcaccgcggg 840
gatatttcaa attgaaccca ggaaaaagct ctgtaatgag atccgatgta cccatagaca 900
tttgtgtgtc tgaatgtatt acaccaaatg gaagcatctc caacgacaag ccattccaaa 960
atgtgaacaa agttacatat ggaaaatgcc ccaagtatat caggcaaaac actttaaagt 1020
tggccactgg gatgaggaat gtgccagaaa agcaaaccag aggaatcttt ggggcgatag 1080
cgggattcat cgaaaacggc tgggaaggaa tggttgatgg gtggtatggg ttccgatatc 1140
aaaactctga aggaacaggg caagctgcag atctaaagag cactcaagca gccatcgacc 1200
agattaatgg aaagttaaac agggtgattg aaagaaccaa tgagaaattc catcaaatag 1260
agaaggaatt ctcagaagta gaaggaagaa ttcaggactt ggagaaatat gtagaagaca 1320
ccaaaataga cctatggtcc tacaatgcag aactgctggt ggctctagaa aatcaacata 1380
caattgactt aacagatgca gaaatgaata aattatttga gaagactaga cgccagttaa 1440

```
gagaaaatgc agaagacatg ggagatggat gtttcaagat ttaccacaag tgtgataatg   1500

catgcattga gtcaataaga actggaacat atgaccatta catatacaaa gatgaagcat   1560

taaacaaccg atttcagatc aaaggtgtag aattgaaatc aggctacaaa gattggatac   1620

tgtggatttc attcgccata tcatgcttct taatttgcgt tgttctattg ggtttcatta   1680

tgtgggcttg ccaaaaaggc aacatcagat gcaacatttg catttgagta aactgatagt   1740

taaaaacacc cttgtttcta ct                                            1762


<210> SEQ ID NO 12
<211> LENGTH: 565
<212> TYPE: PRT
<213> ORGANISM: Influenza A virus (H3N8)

<400> SEQUENCE: 12

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Val Leu Asp Gly Arg Asn Cys Thr
65                  70                  75                  80

Leu Ile Asp Ala Met Leu Gly Asp Pro Gln Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro His Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Pro Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
```

-continued

```
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Asp Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Lys Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 13
<211> LENGTH: 1565
<212> TYPE: DNA
<213> ORGANISM: Influenza A virus (H3N8)

<400> SEQUENCE: 13

agcaaaagca gggtagataa tcactcactg agtgacatca aagtcatggc gtctcaaggc      60

accaaacgat cctatgaaca gatggaaact gatggggaac gccagaatgc aactgaaatc     120

agaacatctg tcggaaggat ggtgggagga atcggacggt tttatgtcca gatgtgtact     180

gagcttaaac taaacgacta tgaagggcgg ctgattcaga acagcataac aatagaaagg     240

atggtacttt cggcattcga cgaaagaaga aacaagtatc tcgaggagca tcccagtgct     300

gggaaagacc ctaagaaaac ggggggcccg atatacagaa gaaaagatgg gaaatggatg     360

agggaactca tcctccatga taaagaagaa atcatgagaa tctggcgtca ggccaacaat     420

ggtgaagacg ctactgctgg tcttactcac atgatgatct ggcactccaa tctcaacgac     480

accacatacc aaagaacaag ggctcttgtt cggactggga tggatcccag aatgtgctct     540

ttgatgcaag gctcaaccct cccacggaga tctggagccg ctggtgctgc agtaaaaggt     600

gttggaacaa tggtaatgga actcatcaga atgatcaagc gcggaataaa tgatcggaat     660
```

```
ttctggagag gtgaaaatgg tcgaagaacc agaattgctt atgaaagaat gtgcaatatc    720

ctcaaaggga aatttcagac agcagcacaa cgggctatga tggaccaggt gagggaaggc    780

cgcaaccctg gaaacgctga aattgaggat ctcattttct tggcacgatc agcacttatt    840

ttgagaggat cagtagccca taaatcatgc ctacctgcct gtgtttatgg ccttgcagta    900

accagtgggt atgactttga gaaggaagga tactctctgg ttggaattga tcctttcaaa    960

ctactccaga acagtcaaat tttcagtcta atcagaccaa aagaaaaccc agcacacaaa   1020

agccaattgg tgtggatggc atgccattct gcagcatttg aggatctgag agttttaaat   1080

ttcattagag gaaccaaagt aatcccaaga ggacagttaa caaccagagg agttcaaatt   1140

gcttcaaatg aaaacatgga gacaataaat tctagcacac ttgaactgag aagcaaatat   1200

tgggcaataa gaaccagaag cggaggaaac accagtcaac agagagcatc tgcaggacag   1260

ataagtgtgc aacctacttt ctcagtacag agaaatcttc cctttgagag agcaaccatt   1320

atggctgcat tcactggtaa cactgaaggg aggacttccg acatgagaac ggaaatcata   1380

aggatgatgg aaaatgccaa atcagaagat gtgtctttcc aggggcgggg agtcttcgag   1440

ctctcggacg aaaaggcaac gaacccgatc gtgccttcct ttgacatgag caatgaaggg   1500

tcttatttct tcggagacaa tgctgaggag tttgacaatt aaagaaaaat acccttgttt   1560

ctact                                                               1565
```

```
<210> SEQ ID NO 14
<211> LENGTH: 498
<212> TYPE: PRT
<213> ORGANISM: Influenza A virus (H3N8)

<400> SEQUENCE: 14

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Thr Ser Val Gly Arg Met
            20                  25                  30

Val Gly Gly Ile Gly Arg Phe Tyr Val Gln Met Cys Thr Glu Leu Lys
        35                  40                  45

Leu Asn Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205
```

```
Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Thr Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
        355                 360                 365

Glu Asn Met Glu Thr Ile Asn Ser Ser Thr Leu Glu Leu Arg Ser Lys
    370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Lys Ser Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Asn
```

<210> SEQ ID NO 15
<211> LENGTH: 1461
<212> TYPE: DNA
<213> ORGANISM: Influenza A virus (H3N8)

<400> SEQUENCE: 15

```
agcaaaagca ggagtttaaa atgaatccaa atcaaaagat aatagcaatt ggatctgcat      60

cattggggat attaatcatt aatgtcattc tccatgtagt cagcattata gtaacagtac     120

tggtcctcaa taacaataga acagatctaa actgcaaagg gacgatcata agagagtaca     180

atgaaacagt aagagtagaa aaacttactc aatggtataa tatcagtaca attaagtaca     240

tagagagacc ttcaaatgaa tattacatga acaacactga accactttgt gaggcccaag     300

gctttgcacc attttccaaa gataatggaa tacgaattgg gtcgagaggc catgtttttg     360

tgataagaga accttttgta tcatgttcac cctcagaatg tagaaccttt ttcctcacac     420
```

-continued

```
agggctcatt actcaatgac aaacattcta acggcacaat aaaggatcga agtccgtata    480

ggactctgat gagtgtcaaa atagggcaat cacctaatgt atatcaagct aaatttgaat    540

cggtggcatg gtcagcaaca gcatgccatg atggaaaaaa atggatgaca gttggagtca    600

cagggcccga caatcaagca attgcagtag tgaactatgg aggtgttccg gttgatatta    660

ttaattcatg ggcaggggat attttaagaa cccaagaatc atcatgcacc tgcattaaag    720

gagactgtta ttgggtaatg actgatggac cggcaaatag gcaagctaat tataggatat    780

tcaaagcaaa agatggaaga gtaattggac gaactgatat aagtttcaat gggggacaca    840

tagaggagtg ttcttgttac cccaatgaag ggaaggtgga atgcatatgc agagacaatt    900

ggactggaac aaatagacca attctggtaa tatcttctga tctatcgtac acagttggat    960

atttgtgtgc tggcattccc actgacaccc ctaggggaga ggatagtcaa ttcacaggct   1020

catgtacaag tcctttggga aataaaggat acggagtcaa aggtttcggg tttcgacaag   1080

gaactgacgt atgggccgga aggacaatta gtaggacttc aagatcagga ttcgaaataa   1140

taaaaatcag gaatggttgg acacagaata gtaaggacca aatcaggagg caagtgatta   1200

tcgatgaccc aaattggtca ggatatagcg gttctttcac attgccggtt gaattaacaa   1260

aaaaaggatg tttggtcccc tgtttctggg ttgaaatgat tagaggtaaa cctgaagaaa   1320

caacaatatg gacctctagc agctccattg tgatgtgtgg agtagatcat aaaattgcca   1380

gttggtcatg gcacgatgga gcaattcttc cctttgacat cgataagatg taatttatga   1440

aaaaaactcc ttgtttctac t                                             1461
```

<210> SEQ ID NO 16
<211> LENGTH: 470
<212> TYPE: PRT
<213> ORGANISM: Influenza A virus (H3N8)

<400> SEQUENCE: 16

```
Met Asn Pro Asn Gln Lys Ile Ile Ala Ile Gly Ser Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Leu Thr Gln
    50                  55                  60

Trp Tyr Asn Ile Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Lys Phe Glu Ser Val Ala
                165                 170                 175

Trp Ser Ala Thr Ala Cys His Asp Gly Lys Lys Trp Met Thr Val Gly
            180                 185                 190
```

```
Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Asn Tyr Arg Ile Phe Lys Ala
                245                 250                 255

Lys Asp Gly Arg Val Ile Gly Arg Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470


<210> SEQ ID NO 17
<211> LENGTH: 1027
<212> TYPE: DNA
<213> ORGANISM: Influenza A virus (H3N8)

<400> SEQUENCE: 17

agcaaaagca ggtagatatt taaagatgag tcttctaacc gaagtcgaaa cgtacgttct     60

ctctatcata ccatcaggcc ccctcaaagc cgagatcgcg cagagacttg aagatgtctt    120

tgcgggaaag aacaccgatc ttgaggcact tatggaatgg ctaaagacaa gaccaatcct    180

gtcacctctg actaaaggga ttttaggatt tgtattcacg ctcaccgtgc ccagtgagcg    240

aggactgcag cgtagacgct ttgtccaaaa tgcccttagt ggaaacggag atccaaacaa    300

catggacaga gcagtaaaac tatacaggaa gcttaaaaga gaaataacat tccatggggc    360

aaaagaagtg gcactcagct attccactgg tgcactagcc agttgcatgg gactcatata    420

caacagaatg ggaactatta caaccgaagt ggcatttggc ctggtatgcg ccacatgtga    480
```

-continued

```
acagattgct gattcccagc atcggtctca caggcagatg gtgacaacaa ccaacccatt    540

aatcagacat gaaaacagaa tggtattagc cagcaccacg gctaaagcca tggaacagat    600

ggcaggatcg agtgagcaag cagcagaggc catggaggtt gctagtaggg ctaggcagat    660

ggtacaggca atgagaacca ttgggaccca ccctagctcc agtgccggtt tgaaagatga    720

tctccttgaa aatttacagg cctaccagaa acggatggga gtgcaaatgc agcgattcaa    780

gtgatcctct cgttactgca gcaagtatca ttgggatctt gcacttgata ttgtggattc    840

ttgatcgtct ttcttcaaa ttcatttatc gtcgccttaa atacgggtta aaaagagggc    900

cttctacgga aggagtacct gagtctatga gggaagaata tcggcaggaa cagcagaatg    960

ctgtggatgt tgacgatggt cattttgtca acatagagct ggagtaaaaa actaccttgt   1020

ttctact                                                             1027


<210> SEQ ID NO 18
<211> LENGTH: 252
<212> TYPE: PRT
<213> ORGANISM: Influenza A virus (H3N8)

<400> SEQUENCE: 18

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Ile Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 19
<211> LENGTH: 91
```

<212> TYPE: PRT
<213> ORGANISM: Influenza A virus (H3N8)

<400> SEQUENCE: 19

```
Met Ser Leu Leu Thr Glu Val Glu Thr Glu Cys Lys Cys Ser Asp Ser
1               5                   10                  15

Ser Asp Pro Leu Val Thr Ala Ala Ser Ile Ile Gly Ile Leu His Leu
            20                  25                  30

Ile Leu Trp Ile Leu Asp Arg Leu Phe Phe Lys Phe Ile Tyr Arg Arg
        35                  40                  45

Leu Lys Tyr Gly Leu Lys Arg Gly Pro Ser Thr Glu Gly Val Pro Glu
    50                  55                  60

Ser Met Arg Glu Glu Tyr Arg Gln Glu Gln Gln Asn Ala Val Asp Val
65                  70                  75                  80

Asp Asp Gly His Phe Val Asn Ile Glu Leu Glu
                85                  90
```

<210> SEQ ID NO 20
<211> LENGTH: 890
<212> TYPE: DNA
<213> ORGANISM: Influenza A virus (H3N8)

<400> SEQUENCE: 20

```
agcaaaagca gggtgacaaa aacataatgg attccaacac tgtgtcaagc tttcaggtag      60

actgttttct ttggcatgtc cgcaaacaat tcgcagacca agaactgggt gatgccccat     120

tccttgaccg gcttcgccga gaccagaagt ccctaagggg aagaggtagc actcttggtc     180

tggacatcga aacagccact catgcaggaa agcagatagt ggagcagatt ctggaaaagg     240

aatcagatga ggcacctaaa atgaccattg cctctgttcc tgcttcacgc tacttaactg     300

acatgactct tgatgagatg tcaagagact ggttcatgct catgcccaag caaaaagtaa     360

caggctccct atgtataaga atggaccagg caatcatgga taagaacatc atacttaaag     420

caaactttag tgtgattttc gaaaggctgg aaacactaat actacttaga gccttcaccg     480

aagaaggagc aatcgttggc gaaatttcac cattaccttc tcttccagga catactaatg     540

aggatgtcaa aaatgcaatt ggggtcctca tcggaggatt taaatggaat gataatacgg     600

ttaaaatctc tgaaactcta cagagattcg cttggagaag cagtcatgag aatgggagac     660

cttcactccc ttcaaagcag aaacgaaaaa tggagagaac aattaagcca gaaatttgaa     720

gaaataagat ggttgattga agaagtgcga catagactga aaaatacaga aaatagtttt     780

gaacaaataa catttatgca agccttacaa ctattgcttg aagtagaaca agagataaga     840

actttctcgt ttcagcttat ttaatgataa aaaacaccct tgtttctact                890
```

<210> SEQ ID NO 21
<211> LENGTH: 230
<212> TYPE: PRT
<213> ORGANISM: Influenza A virus (H3N8)

<400> SEQUENCE: 21

```
Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
```

```
    50                  55                  60

Val Glu Gln Ile Leu Glu Lys Glu Ser Asp Glu Ala Pro Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Phe Lys Trp Asn Asp Asn Thr Val
            180                 185                 190

Lys Ile Ser Glu Thr Leu Gln Arg Phe Ala Trp Arg Ser Ser His Glu
        195                 200                 205

Asn Gly Arg Pro Ser Leu Pro Ser Lys Gln Lys Arg Lys Met Glu Arg
    210                 215                 220

Thr Ile Lys Pro Glu Ile
225                 230


<210> SEQ ID NO 22
<211> LENGTH: 121
<212> TYPE: PRT
<213> ORGANISM: Influenza A virus (H3N8)

<400> SEQUENCE: 22

Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
            20                  25                  30

Ile Arg Leu Lys Ser Leu Lys Leu Tyr Arg Asp Ser Leu Gly Glu Ala
        35                  40                  45

Val Met Arg Met Gly Asp Leu His Ser Leu Gln Ser Arg Asn Glu Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Asn Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
        115                 120


<210> SEQ ID NO 23
<211> LENGTH: 1765
<212> TYPE: DNA
<213> ORGANISM: Influenza A virus (H3N2)

<400> SEQUENCE: 23

agcaaaagca ggggatactt tcattaatca tgaaaactgt tattgcttta agctatattt      60

tctgcctggc ttttggtcag aatcttctag gaaatgaaaa taatgctgca acactatgcc     120
```

-continued

```
tgggacatca tgcagtgccg aacgggacaa tggtgaaaac tatcacagac gatcaaattg    180
aggtgaccaa cgccaccgag ctagtccaaa actcctcaac agggaaaata tgcaacaatc    240
cccacaagat tcttgatggg agggactgca cactaataga tgccctacta ggggacccac    300
actgtgacgt cttccaaaat gagacatggg acctttttgt ggaacgaagc aatgctttta    360
gcaattgtta cccttatgat gtaccagact atgcatccct ccgatccata gttgcatcat    420
caggcacatt ggagttcatc actgaaggtt tcacttgggc aggagtaact caaaatggag    480
gaagcggtgc ttgtaaaagg ggacctgcta atagtttctt cagtagatta aattggttaa    540
ctaaatcagg aaatacatat ccagtgttga atgtgactat gccaaacaac aacaatttcg    600
acaaattata catttgggga gttcatcacc caagcactaa tcaagaacaa accagcctgt    660
atattcaggc ctcaggaaga gtcacagtct ctaccaggag aagccaacag accataatcc    720
caaacattgg atctagaccc ttggtaaggg gccaatctgg cagaataagc gtatattgga    780
caatagtcaa acctggagac atactggtaa taaacagtaa tggaaaccta atcgctcctc    840
gaggatactt caaaatgcac attgggaaaa gctcaataat gagatcagat gcacctattg    900
acacctgcat ttccgaatgt atcaccccga acgggagcat ccccaatgaa aagcccttcc    960
aaaatgtaaa caagatcaca tacggagcat gtcccaaata tgttaagcaa aacaccttga   1020
aactggcaac aggaatgcgg aatgtccctg agaggcaaac cagaggcctg ttcggcgcaa   1080
tagcaggctt catagaaaat ggatgggaag ggatggtaga cggttggtat ggcttcaggc   1140
accaaaattc cgaaggtaca ggacaagcag cagaccttaa aagcactcag gcagccattg   1200
accagattaa tgggaaattg aacagagtga ttgaaaaaac gaatgagaag ttccatcaaa   1260
ttgaaaagga gttttccgaa gtagaaggga ggattcaaga ccttgagaga tacgttgaag   1320
acacaaaagt agatctttgg tcttacaatg ccgagcttct tgttgcctta gaaaaccaga   1380
acacaattga tttaactgat tcagaaatga acaaattgtt tgaaaagact aggaggcaat   1440
tgagggaaaa tgctgaagac atgggcaatg gctgcttcaa gatataccac aagtgtgaca   1500
atgcttgcat agaatcgatt agaaacggaa cttatgacca taacatatat agagatgagg   1560
cagtgaacaa tcggttccag atcaaaggtg ttgagctaaa gtctggatac aaagactgga   1620
tcttgtggat ttcctttgcc atatcatgct tttgctttg tgttgtcttg ctgggtttca    1680
ttatgtgggc ctgccagaga ggcaacatta ggtgcaacat ttgcatttga gtgtactaat   1740
aattaaaaac acccttgttt ctact                                          1765
```

```
<210> SEQ ID NO 24
<211> LENGTH: 566
<212> TYPE: PRT
<213> ORGANISM: Influenza A virus (H3N2)

<400> SEQUENCE: 24

Met Lys Thr Val Ile Ala Leu Ser Tyr Ile Phe Cys Leu Ala Phe Gly
1               5                   10                  15

Gln Asn Leu Leu Gly Asn Glu Asn Asn Ala Ala Thr Leu Cys Leu Gly
            20                  25                  30

His His Ala Val Pro Asn Gly Thr Met Val Lys Thr Ile Thr Asp Asp
        35                  40                  45

Gln Ile Glu Val Thr Asn Ala Thr Glu Leu Val Gln Asn Ser Ser Thr
    50                  55                  60

Gly Lys Ile Cys Asn Asn Pro His Lys Ile Leu Asp Gly Arg Asp Cys
65                  70                  75                  80
```

```
Thr Leu Ile Asp Ala Leu Leu Gly Asp Pro His Cys Asp Val Phe Gln
            85                  90                  95

Asn Glu Thr Trp Asp Leu Phe Val Glu Arg Ser Asn Ala Phe Ser Asn
            100                 105                 110

Cys Tyr Pro Tyr Asp Val Pro Asp Tyr Ala Ser Leu Arg Ser Ile Val
        115                 120                 125

Ala Ser Ser Gly Thr Leu Glu Phe Ile Thr Glu Gly Phe Thr Trp Ala
    130                 135                 140

Gly Val Thr Gln Asn Gly Gly Ser Gly Ala Cys Lys Arg Gly Pro Ala
145                 150                 155                 160

Asn Ser Phe Phe Ser Arg Leu Asn Trp Leu Thr Lys Ser Gly Asn Thr
            165                 170                 175

Tyr Pro Val Leu Asn Val Thr Met Pro Asn Asn Asn Asn Phe Asp Lys
            180                 185                 190

Leu Tyr Ile Trp Gly Val His His Pro Ser Thr Asn Gln Glu Gln Thr
        195                 200                 205

Ser Leu Tyr Ile Gln Ala Ser Gly Arg Val Thr Val Ser Thr Arg Arg
    210                 215                 220

Ser Gln Gln Thr Ile Ile Pro Asn Ile Gly Ser Arg Pro Leu Val Arg
225                 230                 235                 240

Gly Gln Ser Gly Arg Ile Ser Val Tyr Trp Thr Ile Val Lys Pro Gly
            245                 250                 255

Asp Ile Leu Val Ile Asn Ser Asn Gly Asn Leu Ile Ala Pro Arg Gly
            260                 265                 270

Tyr Phe Lys Met His Ile Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Glu Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Arg Gln Thr Arg Gly Leu Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
            405                 410                 415

Glu Val Glu Gly Arg Ile Gln Asp Leu Glu Arg Tyr Val Glu Asp Thr
            420                 425                 430

Lys Val Asp Leu Trp Ser Tyr Asn Ala Glu Leu Leu Val Ala Leu Glu
        435                 440                 445

Asn Gln Asn Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
            485                 490                 495

Ile Arg Asn Gly Thr Tyr Asp His Asn Ile Tyr Arg Asp Glu Ala Val
```

```
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 25
<211> LENGTH: 1467
<212> TYPE: DNA
<213> ORGANISM: Influenza A virus (H3N2)

<400> SEQUENCE: 25

agcaaaagca ggagtgaaaa tgaacccaaa tcaaaagata atagcaatag ggtctgtctc     60

tctaaccatt gcaacagtat gtttcctctt acagattgcc atcctagcaa caactgtgac    120

actgtacttc aagcaaaatg aatgcaacat cccctcgaac agtcaagtag tgccatgtaa    180

accaatcata atagaaagga acataacaga ggtagtatat ttgaataata ctaccataga    240

aaaagaaatt tgctccgtag tgctagaata caggaactgg tcgaaaccgc agtgtcaaat    300

tacaggattt gctcctttct ccaaggacaa ctcaatccga ctctccgctg gtggggacat    360

ttgggtaaca agggaacctt atgtgtcatg cgaccacagc aaatgttatc agtttgcact    420

tgggcagggg accacgctga acaataaaca ctcaaacagc acaatacatg ataggacctc    480

tcatcgaact cttttaatga atgagttggg tgttccgttt catttgggaa ccaaacaagt    540

gtgcatagca tggtccagtt caagttgtca cgatgggaaa gcatggttac atgtttgtgt    600

cactggagat gatagaaatg cgactgctag tttcgtttat aatggaatgc ttgttgacag    660

tattggttca tggtctcgaa atatcctcag aactcaagag tcagaatgtg tttgcatcaa    720

tgggacttgt acagtagtaa tgactgatgg aagtgcatca ggaagggctg atactagaat    780

actattcatc agagagggga aaattatcca tattagccca ttgtcaggga gtgctcaaca    840

catagaggaa tgttcctgtt atccccgata tccaaatgtt agatgtgttt gcagagacaa    900

ttggaagggc tccaataggc ccgttataga tataaatatg gcagattata acatcaattc    960

cagttatgtc tgttcaggac ttgttggcga tacaccaagg aatgatgata gctctagcag   1020

cagtaactgc aaggatccta ataatgagag agggaatcca ggagtgaagg ggtgggcctt   1080

tgataatgat aatgacgttt ggatggggag gacaatcagc aaagatttac gttcaggtta   1140

tgagactttc aaggtcattg gtggctggac cactgctaat tccaagtcac aggtcaatag   1200

acaagtcata gttgacaata ataactggtc tggttattct ggtattttct ccgttgaagg   1260

caaaagctgt gttaataggt gtttttatgt ggagttgata agaggagggc cacaagagac   1320

tagagtatgg tggacttcaa atagcattgt cgtattttgt ggtacttctg gtacctatgg   1380

aacaggctca tggcctgatg gggcgaatat taacttcatg cctatataag ctttcgcaat   1440

tttagaaaaa aactccttgt ttctact                                       1467


<210> SEQ ID NO 26
<211> LENGTH: 469
<212> TYPE: PRT
<213> ORGANISM: Influenza A virus (H3N2)

<400> SEQUENCE: 26
```

-continued

```
Met Asn Pro Asn Gln Lys Ile Ile Ala Ile Gly Ser Val Ser Leu Thr
1               5                   10                  15

Ile Ala Thr Val Cys Phe Leu Leu Gln Ile Ala Ile Leu Ala Thr Thr
            20                  25                  30

Val Thr Leu Tyr Phe Lys Gln Asn Glu Cys Asn Ile Pro Ser Asn Ser
        35                  40                  45

Gln Val Val Pro Cys Lys Pro Ile Ile Ile Glu Arg Asn Ile Thr Glu
    50                  55                  60

Val Val Tyr Leu Asn Asn Thr Thr Ile Glu Lys Glu Ile Cys Ser Val
65                  70                  75                  80

Val Leu Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Ser Lys
        115                 120                 125

Cys Tyr Gln Phe Ala Leu Gly Gln Gly Thr Thr Leu Asn Asn Lys His
    130                 135                 140

Ser Asn Ser Thr Ile His Asp Arg Thr Ser His Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Arg Asn Ala Thr Ala Ser Phe Val Tyr Asn
        195                 200                 205

Gly Met Leu Val Asp Ser Ile Gly Ser Trp Ser Arg Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Arg Glu Gly Lys Ile Ile His Ile Ser Pro Leu Ser Gly Ser Ala
            260                 265                 270

Gln His Ile Glu Glu Cys Ser Cys Tyr Pro Arg Tyr Pro Asn Val Arg
        275                 280                 285

Cys Val Cys Arg Asp Asn Trp Lys Gly Ser Asn Arg Pro Val Ile Asp
    290                 295                 300

Ile Asn Met Ala Asp Tyr Asn Ile Asn Ser Ser Tyr Val Cys Ser Gly
305                 310                 315                 320

Leu Val Gly Asp Thr Pro Arg Asn Asp Asp Ser Ser Ser Ser Ser Asn
                325                 330                 335

Cys Lys Asp Pro Asn Asn Glu Arg Gly Asn Pro Gly Val Lys Gly Trp
            340                 345                 350

Ala Phe Asp Asn Asp Asn Asp Val Trp Met Gly Arg Thr Ile Ser Lys
        355                 360                 365

Asp Leu Arg Ser Gly Tyr Glu Thr Phe Lys Val Ile Gly Gly Trp Thr
    370                 375                 380

Thr Ala Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415
```

-continued

```
Cys Val Asn Arg Cys Phe Tyr Val Glu Leu Ile Arg Gly Gly Pro Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465
```

LIVE-ATTENUATED VACCINE HAVING MUTATIONS IN VIRAL POLYMERASE FOR THE TREATMENT AND PREVENTION OF CANINE INFLUENZA VIRUS

CROSS-REFERENCES TO RELATED APPLICATIONS

This application is a continuation of U.S. patent application Ser. No. 15/753,671, filed Feb. 20, 2018, which is a U.S. national phase application filed under 35 U.S.C. § 371 claiming benefit to International Patent Application No. PCT/US16/47715, filed Aug. 19, 2016, which is entitled to priority under 35 U.S.C. § 119(e) to U.S. Provisional Patent Application No. 62/207,571, filed Aug. 20, 2015, each of which application is hereby incorporated herein by reference in its entirety.

BACKGROUND OF THE INVENTION

Influenza A viruses (IAVs) are enveloped viruses that belong to the Orthomyxoviridae family, and contain a genome comprised of eight single-stranded negative-sense RNA viral segments that encode for 10-14 proteins (Baker et al., 2015, Future Virology, 10: 715-730). The hemagglutinin (HA) and the neuraminidase (NA) glycoproteins are the major antigenic determinants of IAV and are essential for receptor binding and fusion, and virion release, respectively (Varghese et al., 1992, Proteins, 14: 327-332). IAV HA and NA glycoproteins within infected organisms and populations are driven to evolve antigenic variants via immunologic pressure, and positive selection of fit viruses occurs gradually in a process known as antigenic drift (Carrat et al., 2007, Vaccine, 24: 6852-6862). The antigenic diversity of glycoproteins is used to further classify IAVs, of which there are 18 HA and 11 NA subtypes (Palese, 2007, The Viruses and Their Replication, Fields Virology, 5th ed. Lippincott Williams and Wilkins; Tong et al., 2013, PLoS, pathogens, e1003657). In addition, antigenically distinct isolates can also exist within the same subtype, referred to as drifted variants. IAVs exist mainly in the wild aquatic fowl reservoir (de Jong et al., 2007, J Virol, 81: 4315-4322; Taubenberger and Kash, 2010, Cell Host & Microbe, 7: 440-451; Webster et al., 1992, Microbiological Reviews, 56: 152-179; Yoon et al., 2014, Current Topics in Microbiology and Immunology, 385: 359-375) and only a small number of mammalian hosts are currently recognized to sustain transmission and sustention of IAVs.

Canine influenza or dog flu is a common and contagious respiratory disease of dogs caused by two IAVs: the H3N8 equine-origin influenza virus that transferred to dogs in the U.S. around 1999 (Crawford et al., 2005, Science, 310: 482-485); and the avian virus-like H3N2 that transferred to dogs in Asia around 2005 (Song et al., 2008, Emerging Infectious Diseases, 14: 741-746). Recently, in 2015, an outbreak of H3N2 canine influenza virus (CIV) similar to the ones detected in dogs in Asia, was reported in the United States (2015, Javrna-J Am Vet med A, 246: 1049). Notably, H3N2 CIV seems to have a broad host range, as it has been isolated from cats during an outbreak of respiratory disease in a shelter in South Korea (Jeoung et al., 2013, Veterinary Microbiology, 165: 281-286; Song et al., 2011, The Journal of General Virology, 92: 2350-2355). CIV represents a new threat to canine health in the United States and worldwide, as the virus rapidly spreads to dogs throughout the racing track circuit (Crawford et al., 2005, Science, 310: 482-485; Yoon et al., 2005, Emerging Infectious Diseases, 11: 1974-1976) or animal shelters Crawford et al., 2005, Science, 310: 482-485; Holt et al., 2010, Journal of the American Veterinary Medical Association, 237: 71-73; Pecoraro et al., 2013, Journal of Veterinary Diagnostic Investigation, 25: 402-406). CIV is a relatively new virus and almost all dogs are susceptible to infection when they are newly exposed because they have not natural immunity. Most dogs that develop CIV infection have a mild illness, but some dogs get very sick and require treatment (Gonzalez et al., 2014, J Virol, 88: 9208-9219). The recent emergence of CIV has important implications, because the ecological niche of IAVs has increased significantly and both of these CIVs (H3N8 and H3N2) have continuously circulated in the dog population since they emerged, creating many opportunities for exposure in humans and other species. Importantly, as dogs are susceptible to mammalian (equine-origin H3N8 CIV) and avian (avian-origin H3N2 CIV) IAVs, they possess all the attributes to become, like pigs, "mixing vessel" species for the emergency of new IAVs with pandemic potential for humans. The fact that dogs are the closest human companion animals makes reassortment between canine and human viruses more likely to occur. In fact, it has been shown that reassortments between H3N8 or H3N2 CIVs and human IAVs are feasible (Song et al., 2015, The Journal of General Virology, 96: 254-258; Song et al., The Journal of General Virology, 93: 551-554). Hence, society should be alert to the possible transmission and potential emergence of CIVs in humans. This is particularly alarming, because the introduction of novel, antigenically distinct glycoproteins (HA and NA) within the backbone of human IAVs has previously been associated with human pandemics (Yen et al., 2009, Current topics in microbiology and immunology, 333: 3-24).

Vaccination is universally accepted as the most effective strategy for the prevention of influenza viral infections (Pica et al., 2013, Annual Review of Medicine, 64: 189-202; Wong et al., 2013, Clinical Microbiology Reviews, 26: 476-492). To date, three types of influenza virus vaccines have been approved by the United States FDA for human use: recombinant viral HA, inactivated influenza vaccines (IIVs), and live attenuated influenza vaccines (LAIVs) (Pica et al., 2013, Annual Review of Medicine, 64: 189-202; Belshe et al., 2007, The New England Journal of Medicine, 356: 685-696; Cox et al., 2008, Influenza and other Respiratory Viruses: 2: 211-219; Osterholm et al., 2012, The Lancet Infectious Diseases, 12: 36-44; Pronker et al., 2012, Vaccine, 30: 7344-7347). In dogs, IIV against H3N8 (and recently H3N2) CIVs are commercially available. IIVs are administered intramuscularly and elicit protective humoral immunity by inducing the production of neutralizing antibodies that target epitopes on HA, typically proximal to the receptor binding site (Osterholm et al., 2012, The Lancet Infectious Diseases, 12: 36-44; Belongia et al., 2009, Journal of Infectious Diseases, 199: 159-167) that prevent (neutralize) viral infection. On the other hand, LAIV mimics the natural route of viral infection and are able to elicit more efficient cellular and humoral immune responses (Belshe et al., 2007, The New England Journal of Medicine, 356: 685-696), providing better immunogenicity and protection against both homologous and heterologous influenza virus strains (Pica et al., 2013, Annual Review of Medicine, 64: 189-202; Gorse et al., 1991, Chest, 100: 977-984).

In 2006, the American Veterinary Medical Association (AVMA) called for the urgent development of an effective vaccine against CIV. A vaccine made from inactivated virus have been developed that is administered subcutaneously as two doses to reduce the severity of the CIV disease and to reduce the incidence of CIV infection in naive dogs (Nobivac, Merck). However, to date, no LAIV for CIV infections has been developed. Thus there is a need in the art for improved vaccines for CIV. The present invention satisfies this unmet need.

SUMMARY OF THE INVENTION

In one aspect, the present invention provides an immunological composition comprising a live-attenuated canine influenza virus (LACIV), wherein the LACIV comprises one or more mutations in one or more of: segment 1 and segment 2 of the viral genome.

In one embodiment, the one or more mutations renders the LACIV temperature sensitive such that the LACIV exhibits reduced viral replication as compared to wildtype canine influenza virus at a temperature selected from the group consisting of normal body temperature and elevated body temperature.

In one embodiment, segment 1 comprises the nucleic acid sequence set forth in SEQ ID NO: 1. In one embodiment, segment 2 comprises the nucleic acid sequence set forth in SEQ ID NO: 2.

In one embodiment, the LACIV comprises one or more mutations in segment 1, which encodes mutant PB2. In one embodiment, mutant PB2 comprises a N265S point mutation. In one embodiment, mutant PB2 comprises the amino acid sequence set forth in SEQ ID NO: 3.

In one embodiment, the LACIV comprises one or more mutations in segment 2, which encodes mutant PB1. In one embodiment, mutant PB1 comprises one or more of: K391E point mutation, E581G point mutation, and A661T point mutation. In one embodiment, mutant PB1 comprises a K391E point mutation, a E581G point mutation, and a A661T point mutation. In one embodiment, mutant PB1 comprises the amino acid sequence set forth in SEQ ID NO: 4.

In one embodiment, the LACIV comprises one or more mutations in segment 1, which encodes mutant PB2; and one or more mutations in segment 2, which encodes mutant PB1.

In one embodiment, mutant PB2 comprises a N265S point mutation and mutant PB1 comprises a K391E point mutation, a E581G point mutation, and a A661T point mutation.

In one embodiment, the LACIV is derived from H3N8 subtype of influenza A virus. In one embodiment, the LACIV expresses HA and NA of H3N8. In one embodiment, the LACIV expresses HA and NA of H3N2.

In one embodiment, the composition is used for the treatment or prevention of canine influenza in a subject.

In one aspect, the method comprises a method for treating or preventing canine influenza in a subject. The method comprises administering to the subject an immunological composition comprising a live-attenuated canine influenza virus (LACIV), wherein the LACIV comprises one or more mutations in one or more of segment 1 and segment 2 of the viral genome.

In one embodiment, the one or more mutations renders the LACIV temperature sensitive such that the LACIV exhibits reduced viral replication as compared to wildtype canine influenza virus at a temperature selected from the group consisting of normal body temperature and elevated body temperature.

In one embodiment, segment 1 comprises the nucleic acid sequence set forth in SEQ ID NO: 1. In one embodiment, segment 2 comprises the nucleic acid sequence set forth in SEQ ID NO: 2.

In one embodiment, the LACIV comprises one or more mutations in segment 1, which encodes mutant PB2. In one embodiment, mutant PB2 comprises a N265S point mutation. In one embodiment, mutant PB2 comprises the amino acid sequence set forth in SEQ ID NO: 3.

In one embodiment, the LACIV comprises one or more mutations in segment 2, which encodes mutant PB1. In one embodiment, mutant PB1 comprises one or more of: K391E point mutation, E581G point mutation, and A661T point mutation. In one embodiment, mutant PB1 comprises a K391E point mutation, a E581G point mutation, and a A661T point mutation. In one embodiment, mutant PB1 comprises the amino acid sequence set forth in SEQ ID NO: 4.

In one embodiment, the LACIV comprises one or more mutations in segment 1, which encodes mutant PB2; and one or more mutations in segment 2, which encodes mutant PB1.

In one embodiment, mutant PB2 comprises a N265S point mutation and mutant PB1 comprises a K391E point mutation, a E581G point mutation, and a A661T point mutation.

In one embodiment, the LACIV is derived from H3N8 subtype of influenza A virus. In one embodiment, the LACIV expresses HA and NA of H3N8. In one embodiment, the LACIV expresses HA and NA of H3N2.

In one embodiment, the subject does not have canine influenza, and wherein the method induces immunity against one or more of: influenza A virus subtype H3N8 and influenza A virus subtype H3N2. In one embodiment, the subject is infected with at least one or more of: influenza A virus subtype H3N8 and influenza A virus subtype H3N2; and wherein the method induces a therapeutic immune response.

In one embodiment, the immunological composition is administered intranasally, intratracheally, orally, intradermally, intramuscularly, intraperitoneally, intravenously, or subcutaneously.

In one embodiment, the subject is a dog.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A: Schematic representation of segments 1 (PB2) and 2 (PB1) of CIV WT (black) and LACIV (white). Amino acid substitutions N265S (PB2) and K391E, E581G, and A661T (PB1) to generate the H3N8 LACIV are indicated. FIG. 1B: Minigenome activity. MDCK cells (12 well plate format, $3\times10^5$ cells/well, triplicates) were transiently co-transfected with 250 ng of ambisense pDZ expression plasmids encoding the minimal requirements for viral genome replication and gene transcription (PB2, PB1, PA and NP), together with 500 ng of a vRNA-like expression plasmid encoding *Gaussia* luciferase (Gluc) under the control of the canine polymerase I promoter (cpPol-I Gluc), and 100 ng of a pCAGGS Cypridina luciferase (Cluc) plasmid to normalize transfection efficiencies. After transfection, cells were placed at 33° C., 37° C. or 39° C. and viral replication and transcription was evaluated 24 h later by luminescence (Gluc). Gluc activity was normalized to that of Cluc. Data represent means and SD. Normalized reporter expression is relative to that in the absence of pDZ NP plasmid. Data were represented as relative activity considering WT H3N8 polymerase activity at each temperature as 100%. *, $P<0.05$ using a Student's t test.

FIG. 2, comprising (FIG. 2A), 37° C. (FIG. 2B) and 39° C. (FIG. 2C). TCS were collected at 12, 24, 48, 72, and 96 h p.i. and viral titers were determined by immunofocus assay (FFU/ml). Data represent the means and SD of the results determined in triplicate. Dotted lines indicate the limit of detection (200 FFU/ml). *, $P<0.05$ using a Student's t test.

FIG. 4, comprising FIG. 4A) Induction of humoral responses: At 14 days post-vaccination, mice were bled and sera was evaluated for the presence of total IgG antibodies against H3N8 CIV proteins using cell extracts of MDCK-infected cells by ELISA. MDCK mock-infected cell extracts were used to evaluate the specificity of the antibody response. OD, optical density. Data represent the means+/−SD of the results for 6 individual mice. * (Nobivac vs LACIV),  (WT vs LACIV) or * (WT vs Nobivac), $P<0.05$ using a Student's t test. FIG. 4B) Protection efficacy: At 15 days post-vaccination, same mice were challenged (i.n.) with $1\times10^5$ PFU of H3N8Wt CIV. To evaluate viral replication, mice were euthanized at days 2 (N=3) and 4 (N=3) post-challenge and lungs were harvested, homogenized, and used to quantify viral titers by immunofocus assay (FFU/ml). The dotted line indicates the limit of detection (200 FFU/ml). ND, virus not detected. Data represent the means+/−SDs. *, $P<0.05$ using a Student's t test.

FIG. 5, comprising (FIG. 5A) Histological features of dog tracheas infected with 200 plaque forming units (PFU) of WT and LACIV or mock-infected with infection media. Lesions are shown in sections stained with haematoxylin and eosin (H&E) at the indicated days post-infection. (FIG. 5B) Infected cells were detected by immunohistochemical staining of the viral NP. Positive cells are stained in brown. Black horizontal bars represent 20 μm. (FIG. 5C) Graphical representation of bead clearance assays in infected and control dog tracheal explants. Lines represent the average time to clear the beads in three independent experiments. Error bars represent SEM. (FIG. 5D) Growth kinetics of WT and LACIV in canine tracheal explants. Vertical bars represent average from three independent experiments.

FIG. 6, comprising FIG. 6A) Antibody cross-reactivity against the heterologous CIV H3N2: At 14 days post-vaccination, mice were bled and sera was evaluated by ELISA for total IgG antibodies against H3N2 CIV proteins using cell extracts of MDCK-infected cells. Mock-infected MDCK cell extracts were used to evaluate the specificity of the antibody response. OD, optical density. Data represent the means+/−SD of the results for 6 individual mice. * (Nobivac vs LACIV),  (WT vs LACIV) or * (WT vs Nobivac), $P<0.05$ using a Student's t test. FIG. 6B) Protection efficacy of H3N8 LACIV against heterologous H3N2 CIV challenge: At 15 days post-vaccination, mice were challenged (i.n.) with $1\times10^5$ PFU of WT H3N2 CIV. To evaluate WT H3N2 CIV replication, mice were sacrificed at days 2 (N=3) and 4 (N=3) post-challenge and lungs were harvested, homogenized, and used to evaluate the presence of virus by immunofocus assay (FFU/ml). The dotted line indicates the limit of detection (200 FFU/ml). ND, virus not detected. Data represent the means+/−SDs. *, $P<0.05$ using a Student's t test.

FIG. 8, comprising (FIG. 8A), 37° C. (FIG. 8B) and 39° C. (FIG. 8C). Tissue culture supernatants were collected at 12, 24, 48, 72 and 96 hours post-infection. Viral titers in tissue culture supernatants were determined by immunofocus assay (Focus Forming Units, FFU/ml) using an anti-NP monoclonal antibody (HT-103). Data represent the means+/−SDs of the results determined in triplicate. Dotted black lines indicates the limit of detection (200 FFU/ml).

FIG. 9, comprising

FIG. 10, comprising

FIG. 11, comprising

FIG. 13, comprising FIG. 13A and FIG. 13B, depict the nucleotide sequence of mutant segment 1 (FIG. 13A) and the amino acid sequence of mutant PB2 (FIG. 13B) of H3N8 LACIV, derived from A/Canine/NY/Dog23/2009 H3N8. The nucleotide changes resulting in the N265S amino acid change are in bold and underlined in FIG. 13A. The N265S amino acid change is in bold and underlined in FIG. 13B.

FIG. 14, comprising FIG. 14A and FIG. 14B, depict the nucleotide sequence of mutant segment 2 (FIG. 14A) and the amino acid sequence of mutant PB1 (FIG. 14B) of H3N8 LACIV, derived from A/Canine/NY/Dog23/2009 H3N8. The nucleotide changes resulting in the K391E, E581G, and A661T amino acid changes are in bold and underlined in FIG. 14A. The K391E, E581G, and A661T amino acid changes are in bold and underlined in FIG. 14B.

DETAILED DESCRIPTION

Figure 1A:
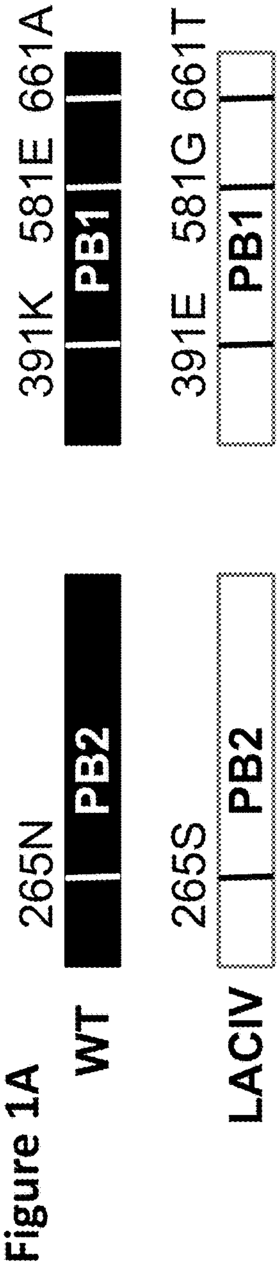
FIG. 1A and FIG. 1B, depicts the results of experiments demonstrating the effects of temperature on the activity of LACIV viral polymerase.

The present invention relates to compositions and methods for the treatment and prevention of canine influenza virus (CIV) and CIV-related pathology. The present invention is based in part upon the discovery that various mutations in segment 1 and segment 2 of the CIV genome, thereby encoding mutant PB2 and PB1 protein, render the virus to be temperature-sensitive. For example, it is described herein that such mutations result in CIV exhibiting reduced viral replication at normal and elevated body temperature as compared to wildtype CIV. However, the temperature-sensitive CIV is able to induce a CIV-specific immune response. Thus, the temperature-sensitive CIV described herein is a live-attenuated canine influenza vaccine (LACIV). Importantly, the LACIV induces a greater CIV-specific immune response as compared to an inactivated CIV vaccine.

In certain embodiments, the present invention provides a composition for the treatment and prevention of canine influenza virus (CIV) and CIV-related pathology. In one embodiment, the composition comprises a LACIV having one or more mutations in segment 1 and/or segment 2 of the viral genome. For example, in one embodiment, the LACIV encodes mutant PB2 and/or mutant PB1. In certain embodiments, mutant PB2 comprises a N265S point mutation. In certain embodiments, mutant PB1 comprises at least one of a K391E point mutation, a E581G point mutation, or A661T point mutation.

In certain embodiments, the present invention provides a composition comprising a master donor virus (MDV) having one or more mutations in segment 1 and/or segment 2 of the viral genome. In one embodiment, the MDV comprises mutant H3N8 segment 1 and/or segment 2, as described herein. In certain embodiments, the MDV can be used to generate an LACIV which is protective against other pathogens. For example, in certain embodiments, an LACIV against another influenza strain can be generated by using the MDV to express one or more viral proteins of the other strain.

In certain embodiments, the present invention provides a method for treating or preventing CIV and CIV-related pathology, comprising administering a composition comprising a LACIV. In certain embodiments, the method comprises intranasal delivery of the LACIV.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "normal temperature" or "normal body temperature" as used herein refers to the temperature of a healthy subject. For example, in certain instances the "normal body temperature" in a human subject is in the range of about 36° C. to about 38° C. In certain instances, in a canine subject, "normal body temperature" is in the range of about 38° C. to about 39.5° C.

The term "elevated temperature" or "elevated body temperature" as used herein refers to a temperature in a subject that is greater than the "normal body temperature" of a subject of a given organism. In certain instances "elevated body temperature" may be indicative of a fever, infection, or other illness. In certain instances, elevated body temperature in a human subject is greater than about 37° C. In certain instances, elevated body temperature in a canine subject is greater than about 38.5° C.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides immunological compositions and methods useful for the inhibition, prevention and treatment of canine influenza and canine influenza related diseases and disorders. In one embodiment, the immunological composition comprises a live-attenuated virus (LAV).

In one embodiment, the present invention provides a temperature-sensitive LAV of a canine influenza virus. For example, it is demonstrated herein that one or more mutations in segment 1 and/or segment 2 of the CIV genome renders the virus to be temperature-sensitive. The temperature-sensitive LACIV of the present invention exhibits reduced viral replication, as compared to wildtype CIV, at both normal body temperature and at elevated or fever temperatures. However, the temperature sensitive LACIV provides antigen-specific immune responses and protection against CIV. In one embodiment, the LACIV provides at least the same antigen-specific immune responses and protection against CIV compared to wildtype CIV. In certain embodiments, the LACIV provides greater antigen-specific immune responses and protection against CIV as compared to inactivated CIV.

In general, wild-type influenza viruses contain a segmented genome with 8 segments as described in Table 1 below:

TABLE 1

| Segment | Gene Product |
|---|---|
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1) and M2 (Matrix protein 2) |
| 8 | NS1 (non-structural protein 1) and NEP/NS2 (non-structural protein 2) |

In certain embodiments, the present invention provides an immunological composition comprising segment 1 and/or segment 2, wherein segment 1 and/or segment 2 comprise one or more mutations. For example, in certain embodiments, the immunological composition comprises an LAV, comprising one or more mutations in segment 1 and/or segment 2. In one embodiment, the immunological composition comprises a LACIV, comprising one or more mutations in segment 1 and/or segment 2.

The present invention also provides methods of preventing, inhibiting, and treating CIV and CIV-related diseases and disorders. In one embodiment, the methods of the invention induce immunity against CIV by generating an immune response directed to CIV. In one embodiment, the methods of the invention induce production of CIV-specific antibodies. In one embodiment, the methods of the invention prevent CIV-related pathology. In one embodiment, the methods of the invention comprise administering an immunological composition comprising a LAV, wherein the LAV comprises one or more mutations in segment 1 and/or segment 2, to a subject in need thereof. In one embodiment, the methods comprise administering an immunological composition to a subject in need thereof, thereby inducing immunity to CIV.

Compositions

The present invention provides immunological compositions that when administered to a subject in need thereof, elicit an immune response directed against canine influenza virus (CIV). In some embodiments, the composition includes polypeptides, nucleotides, vectors, or vaccines. Further, when the compositions are administered to a subject, they elicit an immune response that serves to protect the inoculated subject against canine influenza. As exemplified herein, the composition can be obtained in large quantities for use as a vaccine.

In one embodiment, the present invention provides compositions that are useful as immunomodulatory agents, for example, in stimulating immune responses and in preventing canine influenza and canine influenza-related pathology.

Live-attenuated viruses can be used as immunostimulatory agents to induce the production of CIV-specific antibodies and protect against canine influenza and canine influenza-related pathology. Therefore, in one embodiment, the composition of the invention comprises a live-attenuated CIV (LACIV), wherein the LACIV comprises one or more mutations in the viral genome to render the LACIV temperature sensitive. For example, in one embodiment, the LACIV comprises one or more mutations in segment 1 of the viral genome. The one or more mutations in segment 1 of the viral genome encode a mutant PB2 protein. In one embodiment, the LACIV comprises one or more mutations in segment 2 of the viral genome. The one or more mutations in segment 2 of the viral genome encode a mutant PB1 protein. In one embodiment, the LACIV comprises one or more mutations in segment 1 and one or more mutations in segment 2.

In one embodiment, the LACIV is based upon the genome of Influenza A/canine/NY/dog23/2009 H3N8. Wildtype nucleic acid sequences for each segment of Influenza A/canine/NY/dog23/2009 H3N8 and wildtype amino acid sequences for the encoded proteins are summarized in Table 2 below:

TABLE 2

Wildtype sequences for Influenza A/canine/NY/dog23/2009 H3N8

| Segments | Gene Products | |
|---|---|---|
| Segment 1 (SEQ ID NO: 5) | PB2 (SEQ ID NO: 6) | |
| Segment 2 (SEQ ID NO: 7) | PB1 (SEQ ID NO: 8) | |
| Segment 3 (SEQ ID NO: 9) | PA (SEQ ID NO: 10) | |
| Segment 4 (SEQ ID NO: 11) | HA (SEQ ID NO: 12) | |
| Segment 5 (SEQ ID NO: 13) | NP (SEQ ID NO: 14) | |
| Segment 6 (SEQ ID NO: 15) | NA (SEQ ID NO: 16) | |
| Segment 7 (SEQ ID NO: 17) | M1 (SEQ ID NO: 18) | M2 (SEQ ID NO: 19) |
| Segment 8 (SEQ ID NO: 20) | NS1 (SEQ ID NO: 21) | NEP/NS2 (SEQ ID NO: 22) |

In one embodiment, the composition comprises one or more mutations in the nucleic acid sequences of segment 1, encoding PB2, and/or segment 2, encoding PB1. Thus, in certain embodiments, the composition encodes mutant PB1 and/or mutant PB2. As described herein, the one or more mutations renders the virus to be temperature-sensitive, exhibited reduced viral replication at normal or elevated temperatures.

In some embodiments, the invention provides a composition comprising one or more mutations in segment 1. For example, in one embodiment, the composition comprises segment 1 having one or more mutation which results in the production of mutant PB2 having a point mutation at amino acid residue 265. For example, in one embodiment, the mutant PB2 comprises the amino acid sequence of SEQ ID NO: 6, except having a point mutation at amino acid residue 265. For example, in one embodiment, the mutant PB2 comprises a N265S point mutation, where the mutant PB2 comprises a serine at amino acid residue 265.

In one embodiment, the composition comprises a nucleic acid sequence encoding a mutant PB2 having an amino acid sequence of SEQ ID NO: 3. In one embodiment, the composition comprises a nucleic acid sequence encoding a mutant PB2 that is substantially homologous to SEQ ID NO: 3. For example, in certain embodiments, the composition comprises a nucleic acid sequence that encodes a mutant PB2 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 3. In one embodiment, the composition comprises a nucleic acid sequence encoding a mutant PB2 that is substantially homologous to SEQ ID NO: 3, where mutant PB2 that is substantially homologous to SEQ ID NO: 3 comprises the N265S point mutation.

In one embodiment, the composition comprises a mutant segment 1 comprising the nucleotide sequence of SEQ ID NO: 1. In one embodiment, the composition comprises nucleotide sequence that is substantially homologous to SEQ ID NO: 1. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 1. In one embodiment, the composition comprises a nucleotide sequence that is substantially homologous to SEQ ID NO: 1, where the mutant PB2 encoded by the nucleotide sequence that is substantially homologous to SEQ ID NO: 1 comprises the N265S point mutation.

In some embodiments, the invention provides a composition comprising one or more mutations in segment 2. For example, in one embodiment, the composition comprises segment 2 having one or more mutation which results in the production of mutant PB1 having a point mutation at one or more of: amino acid residue 391, amino acid residue 581, and amino acid residue 661. For example, in one embodiment, the mutant PB2 comprises the amino acid sequence of SEQ ID NO: 8, except having a point mutation at one or more of: amino acid residue 391, amino acid residue 581, and amino acid residue 661. For example, in one embodiment, the mutant PB1 comprises a K391E point mutation, where the mutant PB1 comprises a glutamic acid at amino acid residue 391. In one embodiment, the mutant PB1 comprises a E581G point mutation, where the mutant PB1 comprises a glycine at amino acid residue 581. In one embodiment, the mutant PB1 comprises a A661T point mutation, where the mutant PB1 comprises a threonine at amino acid residue 661.

In one embodiment, the composition comprises a nucleic acid sequence encoding a mutant PB1 having an amino acid sequence of SEQ ID NO: 4. In one embodiment, the composition comprises a nucleic acid sequence encoding a mutant PB1 that is substantially homologous to SEQ ID NO: 4. For example, in certain embodiments, the composition comprises a nucleic acid sequence that encodes a mutant PB1 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 4. In one embodiment, the composition comprises a nucleic acid sequence encoding a mutant PB1 that is substantially homologous to SEQ ID NO: 4, where mutant PB1 that is substantially homologous to SEQ ID NO: 4 comprises one or more of the K391E point mutation, E581G point mutation, and A661T point mutation.

In one embodiment, the composition comprises a mutant segment 2 comprising the nucleotide sequence of SEQ ID NO: 2. In one embodiment, the composition comprises nucleotide sequence that is substantially homologous to SEQ ID NO: 2. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 2. In one embodiment, the composition comprises a nucleotide sequence that is substantially homologous to SEQ ID NO: 2, where the mutant PB1 encoded by the nucleotide sequence that is substantially homologous to SEQ ID NO: 2 comprises one or more of the K391E point mutation, E581G point mutation, and A661T point mutation.

In certain embodiments, the composition comprises one or more mutations in segment 1 and one or more mutations in segment 2. For example, in certain embodiments, the composition comprises segment 1 having a N265S point mutation, and segment 2 having one or more of K391E point mutation, E581G point mutation, and A661T point mutation.

In certain embodiments, the composition comprises one or more mutations in the nucleic acid sequences of segment 1 and/or segment 2, while comprising wildtype nucleic acid sequences for the rest of the segmented genome. For example, in one embodiment, the LACIV comprises one or more mutations in segment 1 and comprises wildtype segment 2, segment 3, segment 4, segment 5, segment 6, segment 7, and segment 8. In one embodiment, the LACIV comprises one or more mutation is segment 2 and comprises wildtype segment 1, segment 3, segment 4, segment 5, segment 6, segment 7, and segment 8. In one embodiment, the LACIV comprises one or more mutations in segment 1 and segment 2 and comprises wildtype segment 3, segment 4, segment 5, segment 6, segment 7, and segment 8.

In certain embodiments, the composition comprises one or more mutations in segment 1 and/or segment 2, in combination with one or more mutations in one or more other segments of the viral genome.

For example, in one embodiment, the composition further comprises one or more mutations in segment 8. In one embodiment, the composition comprises a deletion mutant of segment 8, such that the coding region of NS1 protein is truncated or deleted, as described in PCT Patent Application PCT/US2016/047,711, filed on Aug. 19, 2016, claiming priority to U.S. Provisional Patent Application No. 62/207,576, each of which applications are incorporated by reference in their entirety.

For example, in one embodiment, the composition further comprises one or more mutations in segment 4. In one embodiment, the composition comprises a deletion mutant of segment 4, such that HA is not expressed, as described in PCT Patent Application PCT/US2016/047,726, filed on Aug. 19, 2016, claiming priority to U.S. Provisional Patent Application No. 62/207,579, each of which applications are incorporated by reference in their entirety.

In certain embodiments, the composition comprises a mutant segment 1, mutant segment 2, or combination thereof, as described herein, in combination with one or more nucleotide sequences encoding another antigen. For example, in certain embodiments, the composition comprises a mutant segment 1, mutant segment 2, or combination thereof, as described herein, in combination with one or more nucleotide sequences encoding one or more antigens of another virus or strain. For example, in certain aspects, the H3N8 LACIV described herein, comprising a mutant segment 1, mutant segment 2, or combination thereof can be used as a master donor virus (MDV). For example, an MDV comprising an H3N8 comprising a mutant segment 1, mutant segment 2, or combination thereof described herein, can be modified to comprise one or more nucleotide sequences encoding one or more of PB2, PB1, PA, NP, HA, NA, M1, M2, NS1, or NEP/NS2 from another influenza strain. As such a composition comprising an H3N8 comprising a mutant segment 1, mutant segment 2, or combination thereof described herein can provide protection against a different strain, when the composition expresses an antigen of the different strain. For example, in one embodiment, a composition comprises the backbone of a H3N8 LACIV comprising a mutant segment 1, mutant segment 2, or combination thereof described herein, further comprising one or more nucleotide sequences encoding one or more of PB2, PB1, PA, NP, HA, NA, M1, M2, NS1, or NEP/NS2 from another influenza strain. In one embodiment, the composition comprises the backbone of a H3N8 LACIV comprising a mutant segment 1, mutant segment 2, or combination thereof described herein, further comprising one or more nucleotide sequences encoding one or more of HA or NA of a different influenza strain, including but not limited to H3N2 CIV. For example, the composition comprising the backbone of a H3N8 LACIV described herein, may be modified to express one or more viral proteins of a newly emergent strain, thereby providing protection against the newly emergent strain.

In one embodiment, the composition comprises segment 1, segment 2, segment 3, segment 5, segment 7, and segment 8 of H3N8 LACIV, described herein, comprising one or more point mutations in one or more of segment 1 and segment 2, where the composition further comprises segment 4 and segment 6, of a different CIV strain, including but not limited to H3N2 CIV.

In one embodiment, the composition comprises a mutant segment 1 of H3N8, mutant segment 2 of H3N8, or a combination thereof, further comprising segment 4, segment 6, or a combination thereof of H3N2. In one embodiment, the composition comprising a mutant segment 1 of H3N8, mutant segment 2 of H3N8, or a combination thereof, further comprising segment 4, segment 6, or a combination thereof of H3N2 is an H3N2 LACIV. In certain aspects, the mutant segment 1, mutant segment 2, or combination thereof of H3N8 provides for the temperature sensitive attenuated phenotype of the LACIV, while the segment 4, segment 6, or combination thereof, of H3N2, encodes H3N2 HA, H3N2 NA, or combination thereof to elicit an H3N2 specific immune response in the subject.

The nucleotide sequence of segment 4 of A/Canine/Illinois/11613/2015 H3N2 is provided in SEQ ID NO: 23. The amino acid sequence of HA, encoded by segment 4, of A/Canine/Illinois/11613/2015 H3N2 is provided in SEQ ID NO: 24. The nucleotide sequence of segment 6 of A/Canine/Illinois/11613/2015 H3N2 is provided in SEQ ID NO: 25. The amino acid sequence of NA, encoded by segment 6, of A/Canine/Illinois/11613/2015 H3N2 is provided in SEQ ID NO: 26.

In one embodiment, the composition comprises a nucleic acid sequence encoding HA having the amino acid sequence of SEQ ID NO: 24. In one embodiment, the composition comprises a nucleic acid sequence encoding HA that is substantially homologous to SEQ ID NO: 24. For example, in certain embodiments, the composition comprises a nucleic acid sequence that encodes HA that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 24.

In one embodiment, the complication comprises a segment 4 comprising the nucleotide sequence of SEQ ID NO: 23. In one embodiment, the composition comprises nucleotide sequence that is substantially homologous to SEQ ID NO: 23. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 23.

In one embodiment, the composition comprises a nucleic acid sequence encoding NA having the amino acid sequence of SEQ ID NO: 26. In one embodiment, the composition comprises a nucleic acid sequence encoding HA that is substantially homologous to SEQ ID NO: 26. For example, in certain embodiments, the composition comprises a nucleic acid sequence that encodes HA that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 26.

In one embodiment, the complication comprises a segment 6 comprising the nucleotide sequence of SEQ ID NO: 25. In one embodiment, the composition comprises nucleotide sequence that is substantially homologous to SEQ ID NO: 25. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 25.

In one embodiment, the composition comprises a plurality of LACIV described herein. For example, in one embodiment, the composition comprises a first LACIV, comprising mutant segment 1, mutant segment 2, or combination thereof of H3N8, where the first LACIV comprises segment 4, segment 6, or a combination thereof of H3N8; and the composition further comprises a second LACIV, comprising mutant segment 1, mutant segment 2, or combination thereof of H3N8, where the second LACIV comprises segment 4, segment 6, or a combination thereof of H3N2. In certain embodiments, the composition induces an immune response against both H3N8 and H3N2 CIV.

In certain embodiments, the composition comprises a polynucleotide encoding mutant PB2 and/or mutant PB1. The polynucleotide can be RNA or DNA. In one embodiment, the composition comprises a DNA vaccine.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell.

Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

According to yet another embodiment, composition of the invention, comprising the nucleic acid sequences or combination of nucleic acid sequences of the present invention, is capable of generating a CIV-specific immune response. In another embodiment, the composition of the invention, comprising the nucleic acid sequences or combination of nucleic acid sequences of the present invention, is capable of generating CIV-specific antibodies. In certain embodiments, the composition is able to protect against CIV, including H3N8 CIV and H3N2 CIV.

In one embodiment, the composition of the invention comprises a polypeptide, or a fragment of a polypeptide, a homolog, a variant, a derivative or a salt of a polypeptide having the sequence of any one or more of SEQ ID NO: 3 and SEQ ID NO: 4.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating a CIV-specific immune response. In another embodiment, the composition of the invention, comprising the polypeptide or combination of polypeptides of the present invention, is capable of generating CIV-specific antibodies. In certain embodiments, the composition is able to protect against CIV, including H3N8 CIV and H3N2 CIV.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Live Attenuated Virus (LAV)

The invention relates in part to the generation, selection and identification of live attenuated viruses (LAV) that generate a CIV-specific immune response, and the use of such viruses in vaccine and pharmaceutical formulations. As described herein, in certain embodiments the LACIV comprises one or more mutations in segment 1 and/or one or more mutations in segment 2 that render the virus to be temperature-sensitive. For example, in one embodiment, the temperature-sensitive LACIV exhibits reduced viral replication at normal and elevated temperatures. However, the temperature-sensitive LACIV induces CIV-specific immune responses and antibody production, and is thus able to protect against CIV and CIV-related pathology.

Any mutant virus or strain which has at least one mutation can be selected and used in accordance with the invention. In one embodiment, naturally occurring mutants or variants, or spontaneous mutants can be selected that include at least one mutation in segment 1 and/or segment 2, as described elsewhere herein. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one mutation in segment 1 and/or segment 2, as described elsewhere herein. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an influenza virus, including, but not limited to H3N8 CIV or H3N2 CIV using "reverse genetics" approaches. In this way, natural or other mutations which confer the attenuated phenotype can be engineered into vaccine strains. For example, deletions, insertions, or substitutions of the coding region of segment 1, encoding PB2, and/or segment 2, encoding PB1 can be engineered. Deletions, substitutions or insertions in the non-coding region of segment 1 and/or segment 2 are also contemplated. To this end, mutations in the signals responsible for the transcription, replication, polyadenylation and/or packaging of segment 1 and/or segment 2 can be engineered.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a live attenuated virus, engineered to express one or more epitopes or antigens of CIV along with epitopes or antigens of another pathogen. For example, the attenuated virus can be engineered to express neutralizing epitopes of other preselected strains. Alternatively, epitopes of other viruses can be built into the attenuated mutant virus. Alternatively, epitopes of non-viral infectious pathogens (e.g., parasites, bacteria, fungi) can be engineered into the virus.

In one embodiment, the attenuated viruses selected for use in the invention is capable of inducing a robust anti-CIV response in the host—a feature which contributes to the generation of a strong immune response when used as a vaccine, and which has other biological consequences that make the viruses useful as pharmaceutical agents for the prevention and/or treatment of other viral infections, or other diseases.

The attenuated viruses, which induce a CIV-specific immune response in hosts, may also be used in pharmaceutical formulations for the prophylaxis or treatment of other influenza infections, or influenza-related pathology. In this regard, the tropism of the attenuated virus can be altered to target the virus to a desired target organ, tissue or cells in vivo or ex vivo. Using this approach, the CIV-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

In certain aspects, the immunological composition is useful as a vaccine, where the immunological composition induces an immune response to the antigen in a cell, tissue or mammal. Preferably, the vaccine induces a protective immune response in the mammal. As used herein, an "immunological composition" may comprise, by way of examples, a live-attenuated virus (LAV), an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-CIV immunity or suppresses CIV upon inoculation into an animal.

The invention encompasses vaccine formulations comprising live attenuated virus (LAV), wherein the LAV is a live attenuated canine influenza virus (LACIV). For example, in certain embodiments, the LACIV is temperature-sensitive, exhibiting reduced viral replication at normal and elevated temperatures, as compared to wildtype CIV. In one embodiment, the vaccine comprises a LACIV comprising one or more mutations in segment 1 and/or segment 2, and a suitable excipient. The virus used in the vaccine formulation may be selected from naturally occurring mutants or variants, mutagenized viruses or genetically engineered viruses. Attenuated strains of CIV can also be generated via reassortment techniques, or by using a combination of the reverse genetics approach and reassortment techniques. Naturally occurring variants include viruses isolated from nature as well as spontaneous occurring variants generated during virus propagation. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the vaccine formulation comprises a plurality of mutant CIV. In one embodiment, the vaccine formulation comprises a bivalent vaccine comprising H3N8 LACIV, described herein, in combination with H3N2 LACIV, where the H3N2 LACIV is based upon the H3N8 LACIV backbone but engineered to express H3N2 HA and NA viral proteins (see Example 2).

In one embodiment, the vaccine formulation may comprise one or more of the LACIV, described herein, in combination with other mutant CIV that induce an anti-CIV immune response. For example, in one embodiment, the vaccine formulation comprises a single cycle infectious CIV having one or more mutations in segment 4, such that HA is not expressed. In one embodiment, the vaccine formulation comprises a mutant CIV comprising a deletion mutant in segment 8.

In one embodiment, the present invention comprises a method of generating a LACIV, comprising contacting a host cell with a polynucleotide comprising the nucleic acid sequences of segment 1 and/or segment 2, having one or more mutations, described elsewhere herein.

Propagation of the virus in culture is known to persons in the art. Briefly, the virus is grown in the media compositions in which the host cell is commonly cultured. Suitable host cells for the replication of CIV include, e.g., Vero cells, BHK cells, MDCK cells, 293 cells COS cells, and CEK cells, including 293T cells, COST cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, 5th ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of a virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental attenuated virus.

A vaccine of the present invention, comprising a LACIV, could be administered once. Alternatively, a vaccine of the present invention, comprising a LACIV, could be administered twice or three or more times with a suitable interval between doses. Alternatively, a vaccine of the present invention, comprising a LACIV, could be administered as often as needed to an animal, preferably a mammal.

Methods

The invention provides a method for treating or preventing canine influenza infection or a CIV-related disease or disorder. In one embodiment, the method comprises administering an immunological composition comprising a live-attenuated virus (LAV), wherein the LAV is a LACIV. In one embodiment, the method comprises administering an immunological composition comprising an LACIV comprising one or more mutations in segment 1 and/or segment 2, to a subject in need thereof.

As described herein, in certain embodiments, the LACIV is temperature sensitive, exhibiting decreased viral replication at normal and elevated temperatures, as compared to wildtype CIV. For example, in certain embodiments, the viral replication of LACIV is 2-fold less, 3-fold less, 5-fold less, 10-fold less, 15-fold less, 20-fold less, 50-fold less, 100-fold less, 500-fold less, or 1000-fold less, than wild type CIV at normal or elevated body temperature.

In certain embodiments, the LACIV induces an enhanced immune response as compared to an inactivated CIV. For example, in certain embodiments, the induced immune response of LACIV is 2-fold more, 3-fold more, 5-fold more, 10-fold more, 15-fold more, 20-fold more, 50-fold more, 100-fold more, 500-fold more, or 1000-fold more, than inactivated CIV. The immune response induced the LACIV can be measured using standard assays. For example, in certain embodiments, the immune response induced by LACIV is measured by detecting the amount of CIV-specific antibodies produced in the subject following administration of LACIV.

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In certain embodiments, the subject is a mammal. For example, the subject may include, but is not limited to, a human, primate, cow, horse, sheep, pig, dog, cat, or rodent. In one embodiment, the subject is a dog. The method may be used to treat or prevent CIV or CIV-related pathology in any breed or species of dog. In certain embodiments, the relative amount of active ingredient in a single dose, or the frequency of doses, will vary depending on the age, sex, weight, or breed of subject (e.g. dog).

The composition may be combined with an adjuvant. An adjuvant refers to a compound that enhances the immune response when administered together (or successively) with the immunological composition. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intranasal, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

Pharmaceutical Compositions

The present invention envisions treating or preventing CIV or CIV-related pathology in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising a LACIV to be used as anti-viral agents or as agents against CIV-related diseases and disorders. The pharmaceutical compositions have utility as an anti-viral prophylactic and may be administered to a subject at risk of getting infected or is expected to be exposed to a virus. For example, subjects traveling to parts of the world where CIV is prevalent can be administered a pharmaceutical composition of the invention. In certain embodiments, subjects who are expected to be in contact with other subjects at risk, can be administered a pharmaceutical composition of the invention.

The LACIV of the invention may be engineered using the methods described herein to express proteins or peptides which would target the viruses to a particular site. In one embodiment, where the site to be targeted expresses a receptor to a growth factor, e.g., VEGF, EGF, or PDGF, the LACIV may be engineered to express the appropriate growth factor or portion(s) thereof. Thus, in accordance with the invention, the LACIV may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, the pharmaceutical composition is a veterinary pharmaceutical composition suitable for administration to a veterinary subject, including but not limited to a canine subject. Exemplary canine subjects include dogs, wolves, foxes, coyotes, and jackals.

In certain embodiments, the veterinary pharmaceutical composition is "palatable," meaning an oral veterinary composition that is readily accepted by canines, including dogs, without any coaxing or with some coaxing. Palatable compositions are compositions that score at least 2 using a palatability assessment method wherein dog owners score the composition from 0 to 3, wherein dogs scoring 0 do not consume the composition; dogs scoring 1 consume the composition after some time; dogs scoring 2 consume the composition with some coaxing and dogs scoring 3 consume the composition readily. A skilled person is well-versed in these palatability standards and scoring regimes. In another embodiment, the daily dose for dogs may be around 100 mg/kg. Veterinary pharmaceutical agents that may be included in the compositions of the invention are well-known in the art (see e.g. Plumb' Veterinary Drug Handbook, 5th Edition, ed. Donald C. Plumb, Blackwell Publishing, (2005) or The Merck Veterinary Manual, 9th Edition, (January 2005)).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment or prevention of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: A Temperature Sensitive Live-Attenuated Canine Influenza Virus H3N8 Vaccine It has been reported in recent years the emergence of two influenza A virus (IAV) subtypes in dogs, the canine influenza virus (CIV) H3N8 and H3N2 of equine and avian origin, respectively. Vaccination serves as the best therapeutic option to protect against influenza viral infections. To date, only inactivate influenza vaccines (IIVs) are available for the treatment of CIV infections in dogs. However, the efficacy of current canine IIVs is suboptimal, and novel approaches are necessary for the prevention of disease caused by this contagious canine respiratory pathogen.

IAV is a respiratory pathogen that, at least in humans, is limited to the cooler (33° C.) upper respiratory tract and leads to pathology via replication in the warmer (37° C.) lower respiratory tract (Maassab., 1968, Nature, 219:645-646). The temperature gradient between these two areas in the respiratory tract enabled the development of cold-adapted (ca), temperature-sensitive (ts), attenuated (att) viruses that replicates in the cooler upper respiratory tract (33° C.) to trigger an immune response but cannot damage the warmer lower respiratory tract (37° C.) due to the elevated temperatures restricting replication. This ca, ts, att signature has been mapped to five amino acid residues located in three viral proteins of A/Ann Arbor/6/60 H2N2 (A/AA/6/60): the polymerase basic 2 (PB2; N265S), the polymerase basic 1 (PB1; K391E, D581G, and A661T) and the nucleoprotein (NP; D34G) (Cox et al., 1988, Virology, 167:554-567, Snyder et al., 1988, J Virol, 62:488-495). The mechanism of attenuation is not fully understood but most likely involves multiple steps in the replication cycle of the virus (Chan et al., 2008, Virology, 380:304-311). Importantly, when the ca signature of A/AA/6/60 was introduced into influenza A/Puerto Rico/8/34 H1N1 (PR8) or A/California/04/09 H1N1 (pH1N1) viruses, a similar ts phenotype of these viruses was showed in tissue culture cells and in validated mice models of influenza infections (Cox et al., 2015, J Virol, 89(6): 3421-3426, Jin et al., 2004, J Virol, 78:995-998, Zhou et al., 2012, Vaccine, 30: 3691-3702).

Reported herein is the generation of a recombinant, temperature sensitive H3N8 CIV for its implementation as a live attenuated influenza vaccine (LAIV) candidate. In order to develop a LAIV for the treatment of CIV H3N8 infections, we introduced the four ts, ca, att mutations present in A/AA/6/60 LAIV into the CIV H3N8 (referred to henceforth as LACIV) and rescued this virus using plasmid-based reverse genetics techniques (Martinez-Sobrido et al., 2010, Journal of visualized experiments, 42; doi: 10.3791/2057). Introduction of the ts, ca, att mutations of A/AA/6/60 into the backbone of H3N8 CIV resulted in a virus that efficiently replicate in vitro at lower (33° C.), important for vaccine production, but not at higher (37° C. and 39° C.) temperatures, demonstrating that the LAIV mutations of the current human LAIV are able to confer a ts phenotype to the H3N8 CIV. Importantly, the H3N8 LACIV was safe and able to confer, upon a single intranasal immunization dose, protective immune responses against homologous challenge with H3N8 CIV. Notably, protection conferred by our H3N8 LACIV is more efficient than that provided with currently available H3N8 CIV IIV, representing a better option for the control of CIV in the dog population.

The materials and methods employed in these experiments are now described.

Cells and Viruses

Human embryonic kidney 293T cells (293T; ATCC CRL-11268) and Madin-Darby canine kidney cells (MDCK; ATCC CCL-34) were grown at 37° C. with 5% $CO_2$, in Dulbecco's modified Eagle's medium (DMEM; Mediatech, Inc.) supplemented with 10% fetal bovine serum (FBS), and 1% PSG (penicillin, 100 units/ml; streptomycin 100 μg/ml; L-glutamine, 2 mM) (Nogales et al., 2014, J Virol, 88: 10525-10540).

Recombinant wild-type (WT) and live-attenuated (LACIV) H3N8 CIVs were generated using A/canine/NY/dog23/2009 H3N8 plasmid-based reverse genetics techniques (Feng et al., 2015, J Virol, 89: 6860-6873) and grown in MDCK cells at 33° C. Influenza A/Ca/IL/41915/2015 H3N2, recently isolated from the US 2015 outbreak, was also grown in MDCK cells at 33° C. For infections, virus stocks were diluted in phosphate buffered saline (PBS), 0.3% bovine albumin (BA) and 1% PS (PBS/BA/PS). After viral infections, cells were maintained in DMEM with 0.3% BA, 1% PSG, and 1 μg/ml TPCK-treated trypsin (Sigma) (Zhou et al., 2012, Vaccine, 30: 3691-3702).

Plasmids

To generate the recombinant H3N8 LACIV, the PB2 and PB1 genes were subcloned in a pUC19 plasmid (New England Biolabs) and then, is mutations (PB2 N265S; and PB1 K391E, D581G, and A661T) present in the human A/AA/6/60 H2N2 LAIV were introduced by site-directed mutagenesis using specific primers. The presence of introduced mutations was confirmed by sequencing. Mutated PB2 and PB1 viral segments were subcloned from the pUC19 into the ambisense pDZ plasmid for virus rescue. To test the ability of WT and LACIV H3N8 polymerases to replicate and transcribe at different (33° C., 37° C. and 39° C.) temperatures using a minigenome assay, we engineered a pPolI plasmid containing the canine RNA polymerase I (Pol-I) promoter and the mouse Pol-I terminator separated by SapI endonuclease restriction sites (cpPol-I). The canine Pol-I promoter was obtained by PCR from MDCK cells (Murakami et al., 2008, J Virol, 82: 1605-1609). Then, the *Gaussia* luciferase (Gluc) reporter gene containing the 3' and the 5' non-coding regions of the viral NP (v)RNA was cloned into the cpPol-I plasmid to generate the cpPol-I Gluc reporter plasmid. All plasmids were confirmed by sequencing (ACGT, Inc).

The nucleotide sequences for each segment, and amino acid sequences for each encoded protein, of the H3N8 CIV, are provided in SEQ ID NOs: 5-22. The mutated sequences for segment 1, PB2 protein, segment 2, and PB1 protein, are provided in SEQ ID NOs: 1-4, FIG. 13, and FIG. 14.

Minigenome Assays

For the minigenome assays, parental MDCK cells (12-well plate format, $5\times10^5$ cells/well, triplicates) were co-transfected in suspension using Lipofectamine 2000 with 250 ng of each of the H3N8 WT or LACIV ambisense pDZ PB2, PB1, PA and NP plasmids, together with 500 ng of the cpPol-I Gluc plasmid. A mammalian expression pCAGGS plasmid encoding Cypridina luciferase (Cluc, 100 ng) was also included to normalize transfection efficiencies (Cheng et al., 2015, J Virol, 89: 3523-3533). Cells transfected in the absence of the pDZ NP plasmid were used as negative control. At 24 hours post-transfection, Gluc and Cluc expression levels were determined using Luciferase Assay kits (New England BioLabs) and quantified with a Lumicount luminometer (Packard). Fold induction over the level of induction for the negative control (absence of NP) was determined. The mean values and standard deviations (SDs) were calculated and statistical analysis was performed using a two-tailed Student t test using Microsoft Excel software.

Virus Rescue

Virus rescues were performed as previously described (Nogales et al., 2014, Virology, 476C: 206-216, Nogales et al., 2014, J Viro, 88: 10525-10540). Briefly, co-cultures (1:1) of 293T/MDCK cells (6-well plate format, $10^6$ cells/well, triplicates) were co-transfected in suspension, using Lipofectamine 2000 (Invitrogen), with 1 μg of the eight-ambisense H3N8 WT CIV (pDZ-PB2, -PB1, -PA, -HA, -NP, -NA, -M and -NS) plasmids. To rescue the H3N8 LACIV, WT PB2 and PB1 pDZ plasmids were substituted by those containing PB2 and PB1 H3N8 LACIV. At 12 hours post-transfection, transfection medium was replaced with post-infection (p.i.) medium containing DMEM supplemented with 0.3% BSA, 1% PSG, and 0.5 μg/ml TPCK-treated trypsin (Sigma). Tissue culture supernatants (TCS) were collected at 3 days post-transfection, clarified, and used to infect fresh monolayers of MDCK cells (6-well plate format, $10^6$ cells/well, triplicates). At 3 days p.i., recombinant viruses were plaque purified and scaled up using MDCK cells at 33° C. (Nogales et al., 2014, J Viro, 88: 10525-10540). Virus stocks were titrated by standard plaque assay (plaque forming units, PFU/ml) in MDCK cells at 33° C. (Nogales et al., 2014, J Viro, 88: 10525-10540).

Virus Growth Kinetics

Multicycle growth analyses were performed by infecting confluent monolayers of MDCK cells (12-well plate format, $5\times10^5$ cells/well, triplicates) at a multiplicity of infection (MOI) of 0.001. Viral titers in TCS collected at various times p.i. were determined by immunofocus assay (fluorescent forming units, FFU/ml) in MDCK cells as previously described (Nogales et al., 2014, J Viro, 88: 10525-10540). Briefly, confluent MDCK cells (96-well plate format, $5\times10^4$ cells/well, triplicates) were infected with 10-fold serial dilutions of H3N8 WT or LACIV. At 12 hours p.i., cells were fixed and permeabilized (4% formaldehyde, 0.5% Triton X-100 in PBS) for 15 minutes at room temperature. After washing with PBS, cells were incubated in blocking solution (2.5% BSA in PBS) for 1 hour at room temperature and then incubated with 1 μg/ml of an anti-NP monoclonal antibody (HB-65, ATTC) for 1 hour at 37° C. After washing with PBS, cells were incubated with FITC-conjugated secondary anti-mouse antibody (Dako) for 1 hour at 37° C. The mean values and standard deviation (SDs) were calculated using Microsoft Excel software.

Mice Experiments

Adult (5- to 7-week-old) female WT C57BL/6 mice were purchased from the National Cancer Institute (NCI) and maintained under specific pathogen-free conditions. Mice were anesthetized intraperitoneally (i.p.) with 2,2,2-tribromoethanol (Avertin; 240 mg/kg of body weight) and then inoculated intranasally (i.n.) with 30 μl of the indicated amounts of H3N8 WT or LACIV. Alternatively, 100 μl of a commercially available inactivated H3N8 CIV vaccine (Nobivac, Merck Animal Health) or inactivated H3N2 CIV vaccine (Novartis) were inoculated intramuscularly (i.m). Virus replication was determined by measuring viral titers in the lungs of infected mice at the indicated days p.i. To that end, three mice in each group were euthanized by administration of a lethal dose of avertin and exsanguination, and lungs were collected and homogenized. Virus titers were determined by immunofocus assay (FFU/ml) as indicated above. Mice sera were collected by submandibular bleeding 24 hours prior to viral challenges and evaluated for the presence of influenza virus antibodies by enzyme-linked immunosorbent assays (ELISA) and neutralizing antibodies by hemagglutination inhibition (HAI) assays.

ELISAs

ELISAs were performed as previously described (Nogales et al., 2014, J Viro, 88: 10525-10540) by coating 96-well plates at 4° C. for 16 hours with lysates from mock, H3N8 or H3N2 WT CIV-infected MDCK cells. After blocking with 1% BSA for 1 hour at room temperature, plates were incubated with 2-fold serial dilutions (starting dilution of 1:50) of mice sera for 1 hour at 37° C. After incubation, plates were washed with $H_2O$, and incubated with a HRP-conjugated goat anti-mouse IgG (1:2,000; Southern Biotech) for 1 hour at 37° C. Reactions were then developed with tetramethylbenzidine (TMB) substrate (BioLegend) for 10 minutes at room temperature, quenched with 2N H2504, and read at 450 nm (Vmax kinetic microplate reader; Molecular Devices).

HAI Assays

To evaluate the presence of H3N8 CIV neutralizing antibodies, mice sera were treated with receptor-destroying enzyme (RDE; Denka Seiken) and heat inactivated for 30 min at 56° C. Sera were then serially 2-fold diluted (starting dilution of 1:50) in 96-well V-bottom plates and mixed 1:1 with 4 hemagglutinating units (HAU) of WT H3N8 CIV for 30 min at room temperature. The HAI titers were determined by adding 0.5% turkey red blood cells (RBCs) to the virus-antibody mixtures for 30 min on ice, as previously described (Nogales et al., 2014, J Viro, 88: 10525-10540). The GMT and SDs from individual mice were calculated from the last well where hemagglutination was inhibited.

Canine Tracheal Explants Preparation

Three dog tracheas were collected from healthy Beagles (Charles River Laboratories) used as negative controls in other unrelated research studies. Briefly, tracheas were collected aseptically immediately upon euthanasia and transported in pre-warmed medium as described previously (Gonzalez et al., 2014, J Virol, 88(16): 9208-19). Tracheas were washed a minimum of 5 times for a total period of 4 hours and maintained at 33° C., 5% $CO_2$, and 95% humidity between washes. The connective tissue was removed and the trachea was then open lengthwise. Each tracheal ring was divided in four 0.25 $cm^2$ explants and transferred epithelium facing upwards onto an agarose plug covered by a sterile filter. The explants were then kept for a total of 6 days at 33° C., 5% $CO_2$, and 95% humidity.

Infection of Explants and Quantification of Virus Titers

Explants were infected after a period of 24 hours post-dissection (designed as day zero) with 200 PFU of WT H3N8 CIV, H3N8 LACIV or mock infected with culture medium. Inoculated explants were sampled for virus quantification, bead clearance assays, and histology at day 0, 1, 3 and 5 post-infection. Viral replication was evaluated by plaque assays on MDCK cells by means of immunostaining of plaques.

Estimation of Bead Clearance Time

The ciliary function of tracheal explants was evaluated as described previously (Gonzalez et al., 2014, J Virol, 88(16): 9208-19) by placing five microliters of polystyrene microsphere beads (Polysciences, Northampton, UK) on the explant apical surface and measuring the time to displace the beads.

Histological Analysis and Immunohistochemistry

After collection, the explants were fixed in 10% buffered formalin for a minimum of 48 hours, before paraffin embedding. Subsequently, 4 μm sections of paraffin embedded tissue were either stained with Haematoxylin and Eosin for histopathological evaluation or immunostained for the viral nucleoprotein (NP) using standard procedures. For NP immunostaining, the Dako supervision system was used following the manufacturer's protocol, along with a monoclonal mouse anti-NP (clone HB65; dilution 1:500). Slides were counterstained with Mayer's haematoxylin. Histological images were captured with the cellD software (Olympus).

The results of the experiments are now described

Generation and Characterization of the Ts H3N8 LACIV

To generate a ts H3N8 LACIV the five mutations in the PB2, PB1, and NP genes that were previously identified as the major determinants responsible for the ts phenotype of the human A/AA/6/60 H2N2 LAIV were introduced (Cox et al., 1988, Virology, 167: 554-567, Jin et al., 2003, Virology, 306: 18-24). These amino acid mutations include one mutation in PB2 (N265S) and three mutations in PB1 (K391E, D581G, A661T) (FIG. 1A). No mutation was introduced into the viral NP since H3N8 CIV already contains a G at position 34.

To determine if the mutations introduced into the PB2 and PB1 genes confer a ts phenotype to the H3N8 CIV polymerase, a minigenome assay was performed. To that end, a pPol plasmid containing a vRNA-like segment encoding Gluc under the control of a canine (c) PolI promoter was co-transfected in MDCK cells with the ambisense pDZ plasmids expressing the viral PB2 (WT or LACIV), PB1 (WT or LACIV), PA and NP. After transfection, cells were incubated at different temperatures (33° C., 37° C. and 39°

Figure 1B:
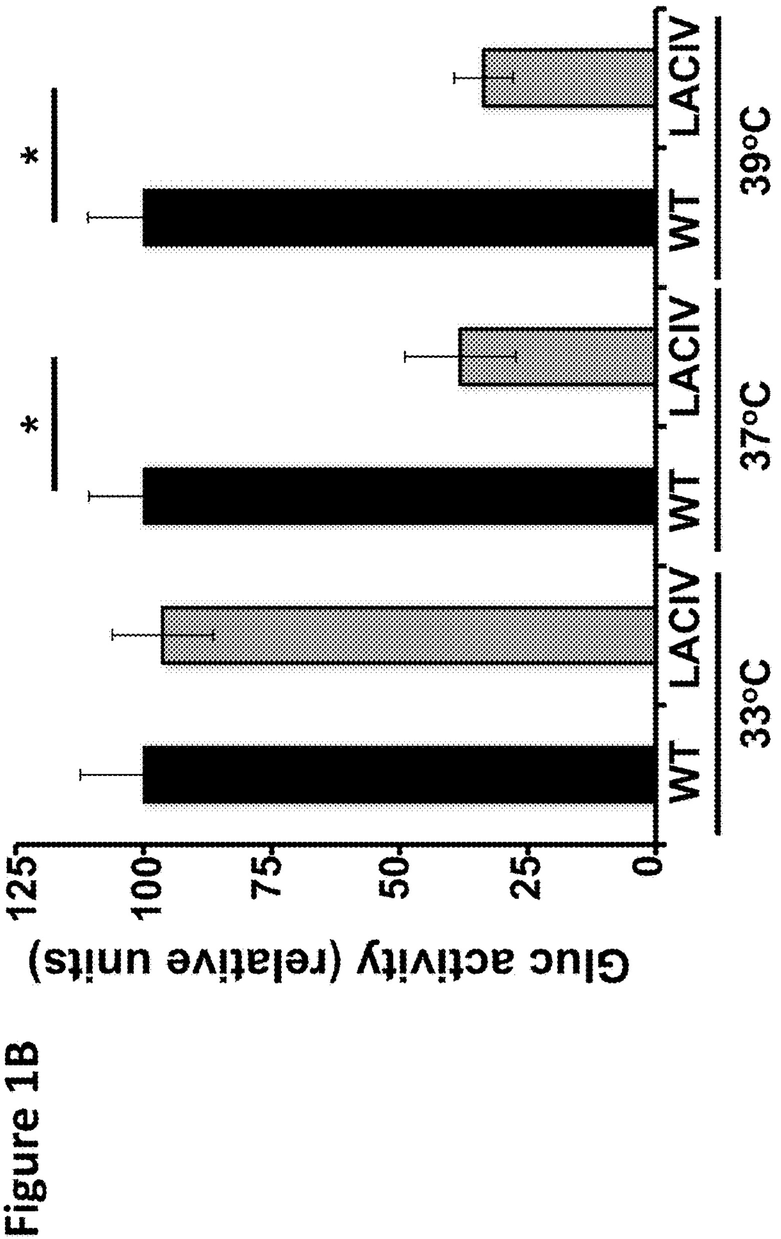

C.) and at 24 hours post-transfection, Gluc expression in the TCS was quantified. Both, WT and LACIV H3N8 resulted in similar Gluc expression levels at 33° C. (FIG. 1B). However, a reduction of Gluc expression was observed at higher temperatures (37° C. and 39° C.) in cells transfected with the H3N8 LACIV plasmids, indicating that the mutations responsible for the ts phenotype of A/AA/6/60 H2N2 also resulted in a ts phenotype when introduced in the H3N8 CIV, as previously described for other viruses.

Figure 2C:
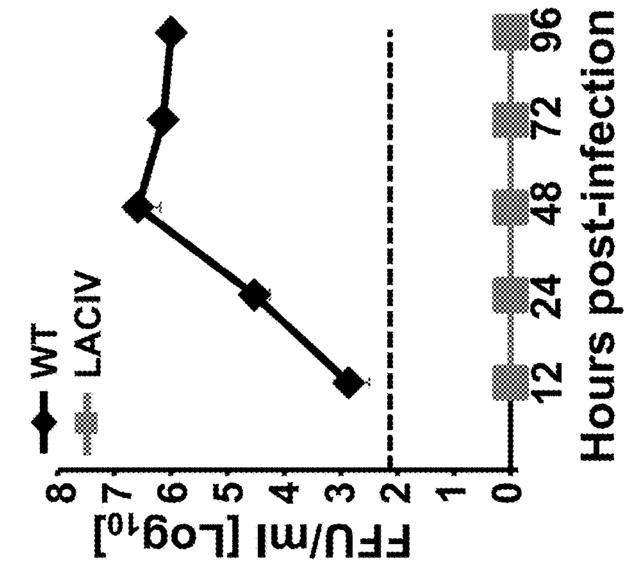
FIG. 2A through FIG. 2C, depicts the results of experiments characterizing H3N8 LACIV in vitro: MDCK cells (12 well plate format, $3\times10^5$ cells/well, triplicates) were infected (MOI of 0.001) with WT (black diamonds) and LACIV (gray squares) H3N8 CIVs and incubated at 33° C.
Figure 2B:
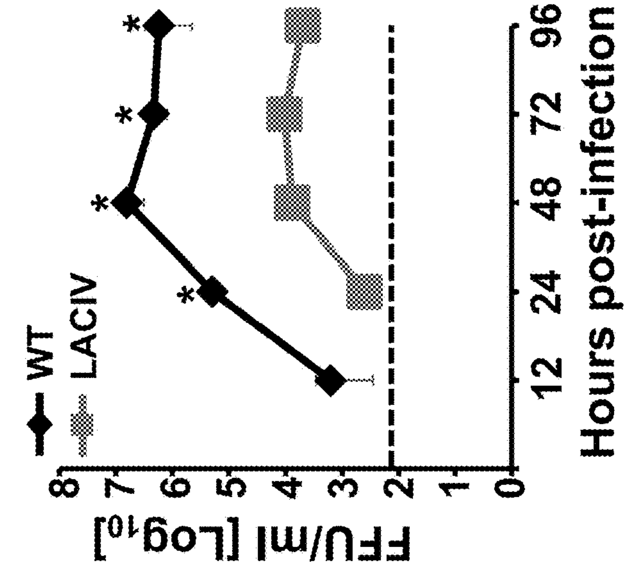
Figure 2A:
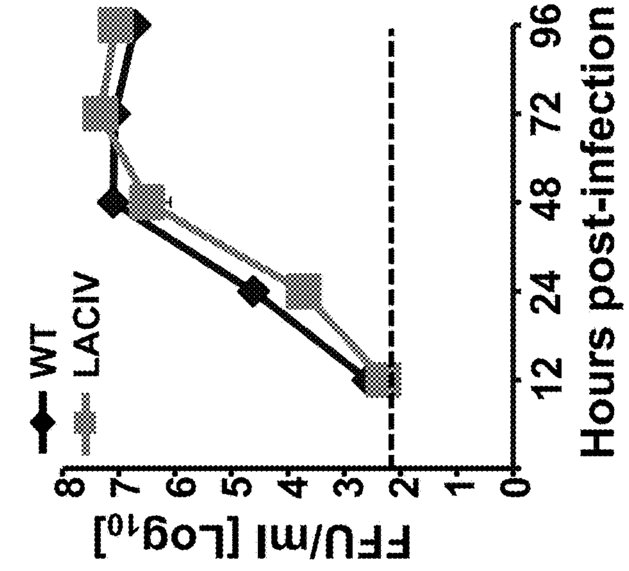

Next an H3N8 LACIV was generated using plasmid-based reverse genetic approaches, as previously described. To test if the ts mutations introduced in the H3N8 CIV polymerases can also result in impaired growth of the H3N8 LACIV at restrictive (37° C. and 39° C.) temperatures but not permissive (33° C.) temperatures, the replication kinetics of the H3N8 LACIV was evaluated and compared to that of the WT H3N8 CIV in MDCK cells infected at low (0.001) MOI (FIG. 2). At 33° C., both WT and LACIV H3N8 grew with undistinguishable kinetics and reached similar high titers ($10^7$ FFU/ml) at 48-72 h p.i. (FIG. 2A). However, at higher (37° C. and 39° C.) temperatures, the WT H3N8 CIV replicated at similar levels as those observed at 33° C. while replication of the H3N8 LACIV was impaired ~2-3-logs at 37° C. (FIG. 2B) or was not detected at 39° C. (FIG. 2C). Altogether, these data demonstrate that the PB2 and PB1 mutations responsible of the ts phenotype of the A/AA/6/60 H2N2 human LAIV are able to confer also a ts phenotype to the H3N8 CIV and that a recombinant H3N8 CIV containing these mutations has a ts phenotype but able to propagate at levels compared to those of WT H3N8 at 33° C., which is important for vaccine production, as in the case of the human LAIV.

LACIV H3N8 is Attenuated In Vivo

Figure 3:
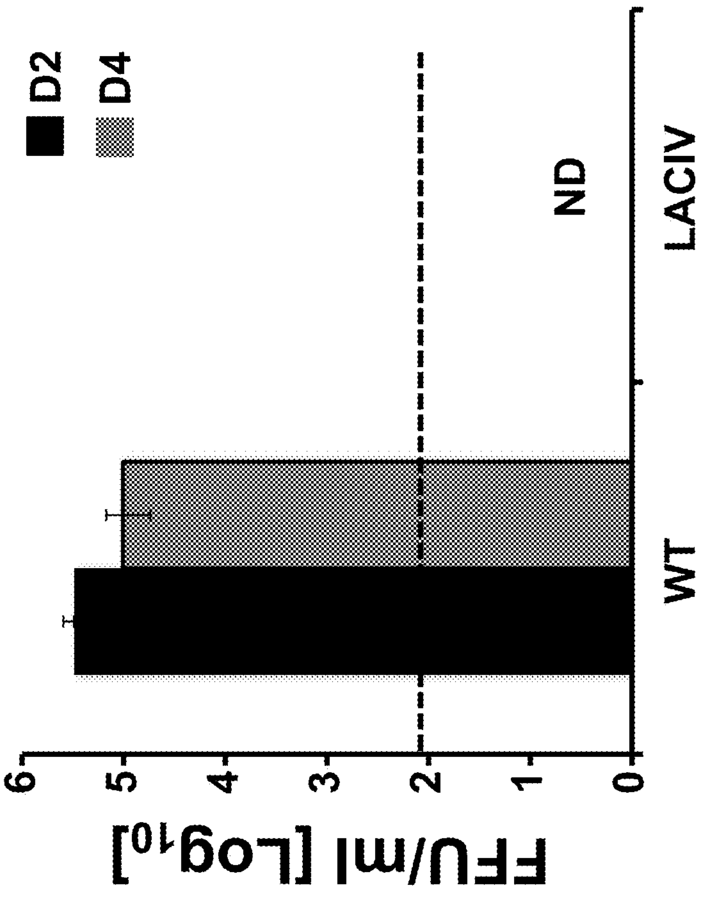
FIG. 3 depicts the results of experiments demonstrating the attenuation of H3N8 LACIV in vivo. Female 5-to-7-week-old C57BL/6 WT mice (N=6) were infected (i.n.) with $1\times10^5$ PFU of WT or LACIV H3N8 CIVs. Three mice were sacrificed at days 2 (black) and 4 (gray) p.i. and lungs were harvested for virus titrations using an immunofocus assay (FFU/ml). Data represent the means and SD. Dotted line indicate limit of detection (200 FFU/ml). ND, virus not detected.

As the H3N8 LACIV presented defects in replication at higher (37° C. and 39° C.) temperatures, it was examined whether the virus was also attenuated in mice. No signs or symptoms of infection were detected after the infection with WT H3N8 CIV. Therefore, CIV replication was measured as an attenuation index. To this end, groups of mice (N=6) were inoculated i.n. with $10^5$ PFU of WT or LACIV H3N8 and viral titers in the lungs of infected mice were evaluated on days 2 (N=3) and 4 (N=3) p.i. (FIG. 3). Notably, virus replication in the lungs was only detected in mice infected with WT H3N8 CIV and no virus was detected in mice infected with the H3N8 LACIV. Altogether, these results indicate that H3N8 LACIV is also attenuated in vivo.

Figure 4A:
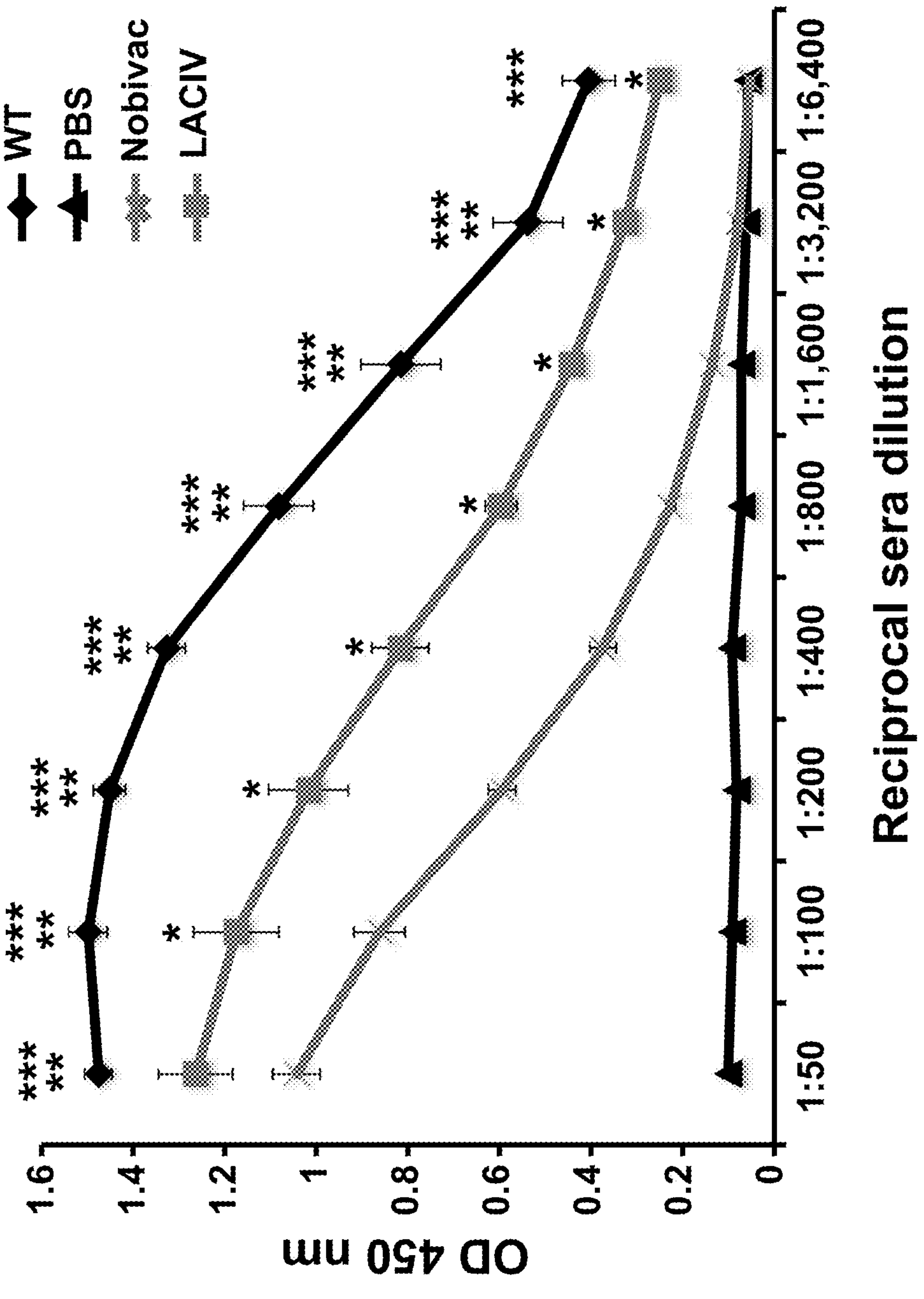
FIG. 4A and FIG. 4B, depicts the results of experiments demonstrating the immunogenicity and protection efficacy of H3N8 LACIV against homologous viral challenge: Female 5-to-7-week-old C57BL/6 WT mice (N=6) were vaccinated (i.n.) with $1\times10^3$ PFU of WT or LACIV H3N8 CIVs. Mice mock (PBS) vaccinated or vaccinated (i.m.) with 100 μl of an H3N8 CIV IIV (Nobivac) were used as internal controls.

Vaccination with H3N8 LACIV Induces Protective Immunity Against WT H3N8 CIV Challenge Since H3N8 LACIV was attenuated in mice, as compared to the WT H3N8 CIV, it was examined whether H3N8 LACIV can be implemented as a LAIV for the treatment of H3N8 CIV. To evaluate this possibility, mice (N=6) were vaccinated (i.n.) with $10^3$ PFU of H3N8 WT or LACIV. In addition, a group of mice was mock (PBS) vaccinated or vaccinated intramuscularly (i.m.) with 100 μl of Nobivac, a commercially available vaccine against H3N8 CIV. Then, humoral immune responses were evaluated in sera collected 2 weeks after vaccination (FIG. 4A). Total H3N8 CIV antibody responses were characterized by ELISA using cell lysates from mock- or H3N8 CIV-infected MDCK cells (Nogales et al., 2016, J Virol, 90: 6291-6302). Mice vaccinated with the H3N8 LACIV elicited high serum IgG titers against parental H3N8 CIV. However, antibody titers of mice vaccinated with the IIV Nobivac were significantly reduced as compared with those from H3N8 LACIV or WT vaccinated mice (FIG. 4A), indicating that H3N8 LACIV induces strongest humoral responses than the IIV, similar to the situation previously described with other influenza viruses. Additionally, HAI assays were performed to examine the presence of neutralizing antibodies on sera from vaccinated mice (Table 3). As expected protective antibody titers against CIV H3N8 were higher in mice vaccinated with the H3N8 LACIV than those observed with the H3N8 IIV Nobivac.

Figure 4B:
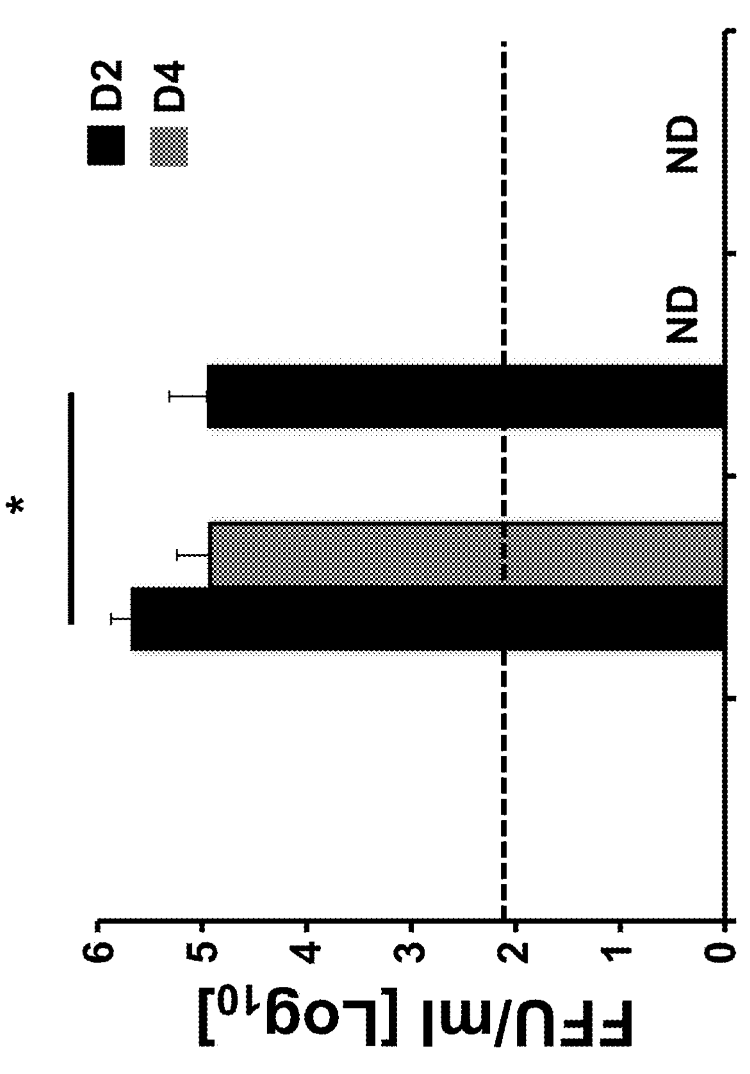

Next, experiments were conducted to evaluate the ability of H3N8 LACIV to induce protective immunity. To that end, mice (N=6) were vaccinated i.n. with $10^3$ PFU of H3N8 WT or LACIV, i.m. with 100 μl of the IIV Nobivac, or mock (PBS) vaccinated. Two weeks post-vaccination, mice were challenged with $10^5$ PFU of homologous WT H3N8 CIV and viral titers in the lungs of infected mice (N=3/group) were evaluate at days 2 and 4 post-challenge (FIG. 4B). As expected, mock-vaccinated mice showed high viral titers at days 2 and 4 p.i. Importantly, lungs from mice immunized with H3N8 WT CIV and with LACIV showed no detectable virus titers at either day post-challenge (FIG. 4B). However, mice vaccinated with the H3N8 IIV Nobivac showed high viral titers at day 2, although no detectable virus at day 4 post-infection (FIG. 4B). Altogether, these data indicated that H3N8 LACIV vaccination induce better immune responses, including neutralizing antibodies, than mice vaccinated with the H3N8 IIV Nobivac, resulting in better protection efficacy against WT H3N8 CIV challenge, favoring the implementation of the H3N8 LACIV over the IIV for a better protection against H3N8 CIV.

H3N8 LACIV is Attenuated in Canine Tracheal Explants Compared to H3N8 WT CIV

Figure 5B:
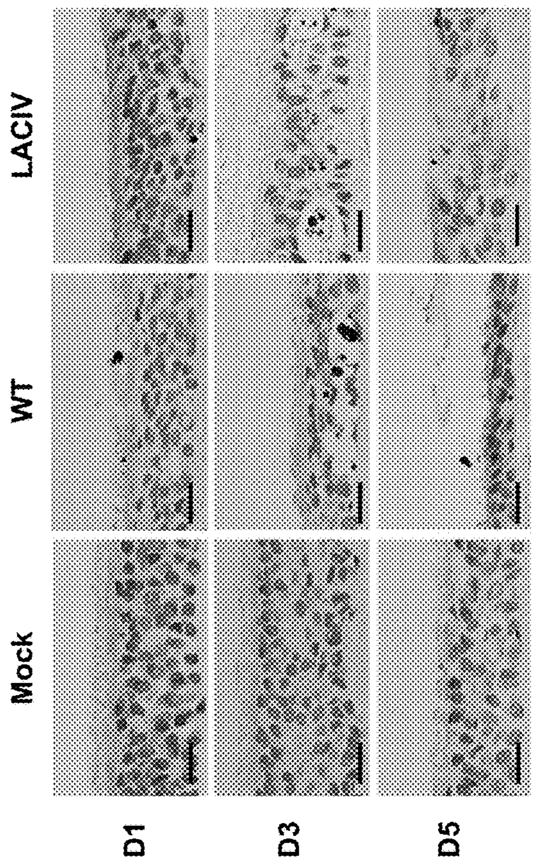
FIG. 5A through FIG. 5D, depicts the results of experiments investigating the ex vivo infection of canine tracheal explants with A/Canine/NY/2009 wild-type (WT) and LAIV (LACIV).
Figure 5A:
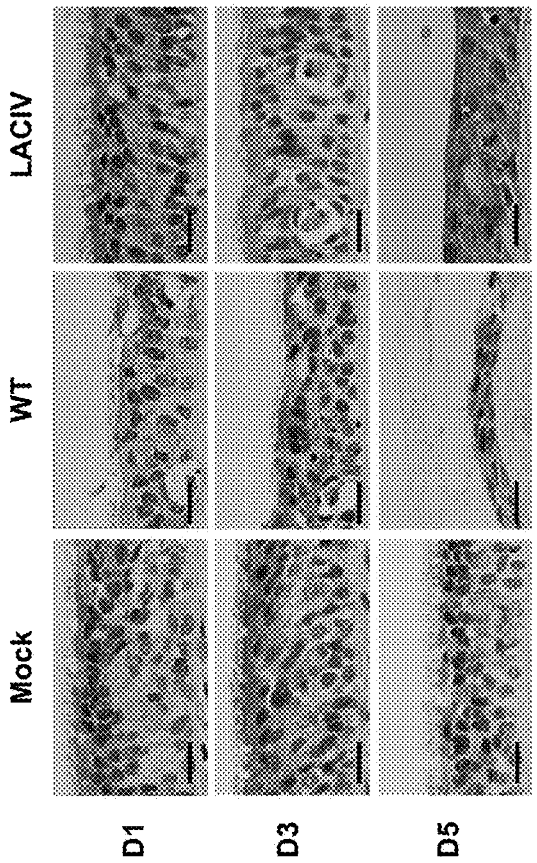
Figure 5C:
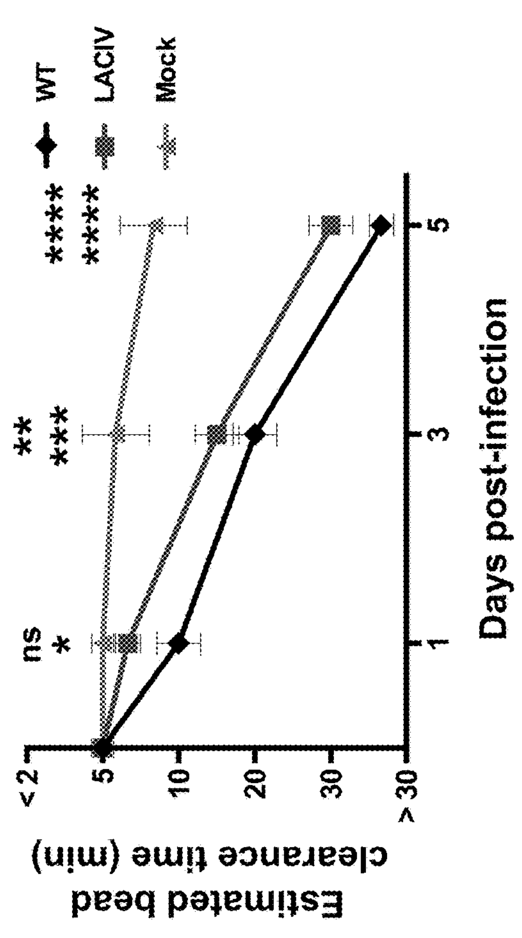

To compare H3N8 LACIV and H3N8 WT CIV pathogenicity and replication efficiency at the site of infection within the natural host, dog tracheal explants were infected with each virus and histological lesions (FIG. 5A), changes in ciliary function (FIG. 5C), viral replication (FIG. 5B) and viral Nucleoprotein (NP) expression (FIG. 5D) were compared at different times post-infection. H3N8 WT CIV induced major histological changes in dog tracheal explants, with thinning and desquamation of the epithelium, loss of cilia (FIG. 5A), and significant reduction of ciliary function (FIG. 5C) from day 1 to day 5 post infection. Interestingly, histological damages induced by H3N8 LACIV were delayed and reduced compared to WT CIV, as the epithelium maintained its normal thickness until day 3 post infection (FIG. 5A) and the ciliary function (FIG. 5C) was only significantly reduced from day 3 post infection.

Figure 5D:
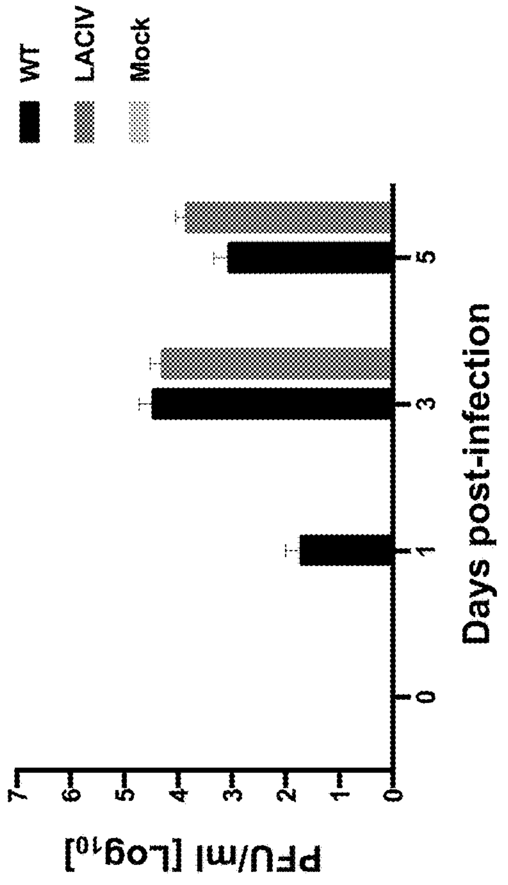

Additionally, viral kinetics and NP expression were comparable between the two viruses, although only CIV WT was detectable at day 1 post infection (FIG. 5D). Overall, these results indicate that LACIV pathogenicity is attenuated in canine tracheal explants compared to H3N8 CIV WT.

H3N8 LACIV Provides Limited Protection Against Heterologous H3N2 CIV

Figure 6A:
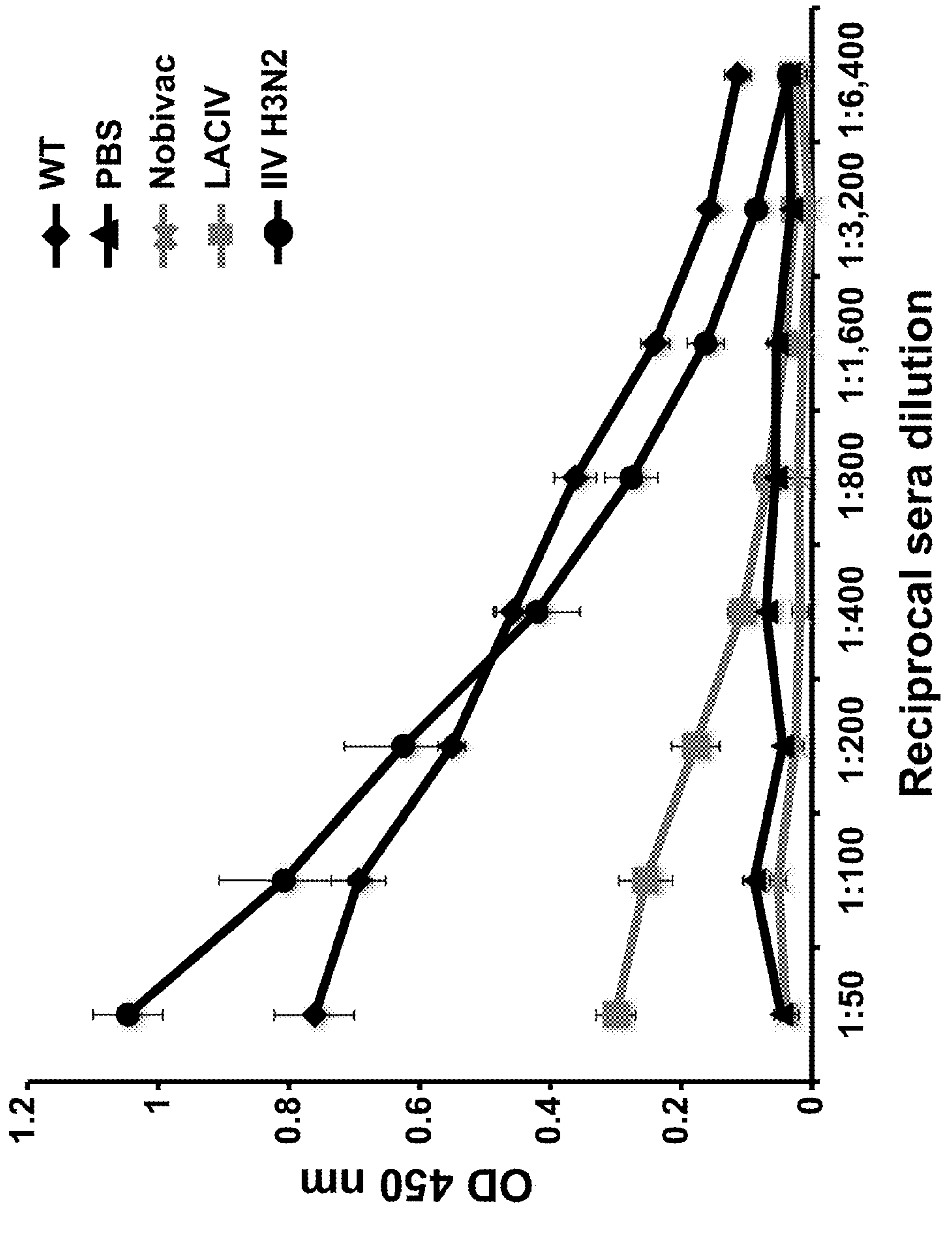
FIG. 6A and FIG. 6B, depicts the results of experiments demonstrating the immunogenicity and protection efficacy of H3N8 LACIV against heterologous H3N2 CIV challenge: Female 5-to-7-week-old C57BL/6 WT mice were vaccinated (i.n.) with $1\times10^3$ PFU of WT and LACIV H3N8 CIVs. Mice mock (PBS) vaccinated or vaccinated (i.m.) with 100 μl of the H3N8 (Noviback) and an H3N2 CIV IIV were used as internal controls.
Figure 6B:
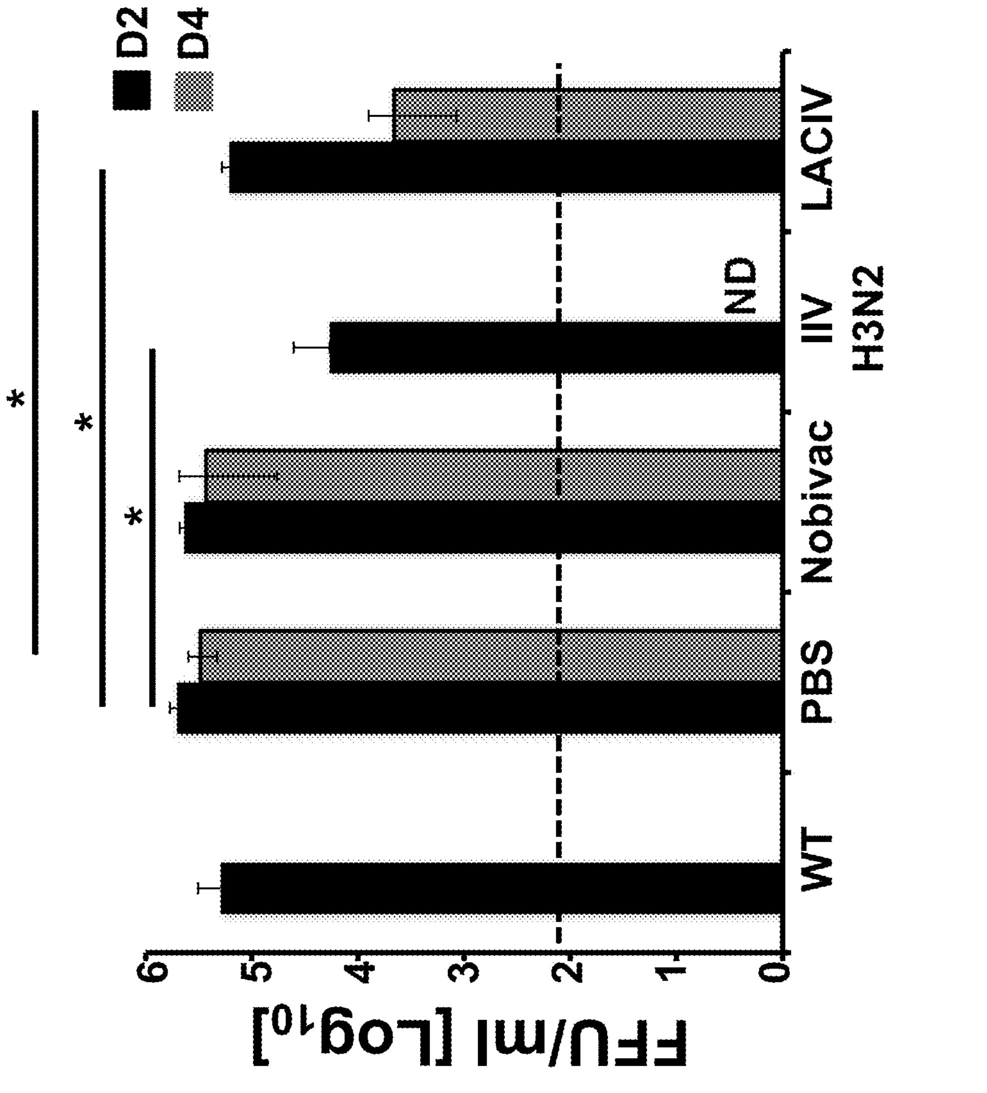

Next, it was evaluated if H3N8 LACIV can induce protective immunity against a heterologous H3N2 CIV challenge (FIG. 6). To that end, mice (N=6) were vaccinated (i.n.) with $10^3$ PFU of H3N8 CIV WT or LACIV. As internal controls, a group of mice was mock (PBS) vaccinated or vaccinated (i.m.) with 100 μl of the H3N8 IIV Nobivac or a commercial H3N2 IIV (Zoetis). Then, presence of antibodies against H3N2 CIV was evaluated by ELISA using cell lysates from mock- or H3N2 CIV-infected MDCK cells (FIG. 6A). Antibodies against H3N2 CIV were detected in sera from mice vaccinated with WT H3N8 CIV and, to a lower extent, in mice vaccinated with H3N8 LACIV, although the levels were lower than those obtained against H3N8 CIV (FIG. 4). No detectable IgG antibodies against H3N2 CIV were detected in mice vaccinated with the H3N8 IIV Nobivac. As expected, the H3N2 CIV IIV induced higher IgG antibodies against H3N2 CIV. These lower level of cross-reactive antibodies against H3N2 CIV upon vaccination with the H3N8 LACIV were further confirmed after challenge (i.n.) with $10^5$ PFU H3N2 CIV 2 weeks post-vaccination (FIG. 6B). Mock-vaccinated mice showed high H3N2 CIV titers that were undistinguishable, either at 2 or 4 days post-challenge, from the animals vaccinated with the H3N8 CIV IIV Nobivac. On the other hand, mice vaccinated with the H3N2 CIV IIV showed reduced or undetectable titers, respectively, at day 2 and 4 post-challenge. Notably, although we observed similar H3N2 CIV titers at day 2 post-challenge, viral titers at day 4 post-infection in mice vaccinated with the H3N8 LACIV were ~100 times lower than those obtained in the mock vaccinated group. These results indicate that although H3N8 LACIV can induce some cross-reactive immune responses and protection efficacy against H3N2 CIV, the efficacy of the H3N8 LACIV is lower than that obtained with the H3N2 IIV.

A Novel LAIV for the Treatment of H3N8 CIV

In this work, we have developed, for the first time, a novel LAIV for the treatment of H3N8 CIV. Using plasmid-based reverse genetics techniques, we have generated a recombinant H3N8 CIV containing the mutations responsible for the ts, ca, att phenotype of the human A/AA/6/60 H2N2 LAIV. Introduction of these mutations in the H3N8 CIV resulted in a ts H3N8 CIV that was highly attenuated, as compared to H3N8 CIV WT, in replication in vivo but able to confer, upon a single i.n. immunization, complete protection against challenge with WT H3N8 CIV, demonstrating the feasibility of implementing the ts H3N8 LACIV as a safe, immunogenic and protective LAIV for the treatment of H3N8 CIV infections.

The ts, ca, att A/AA/6/60 H2N2 LAIV has been licensed for human use. This A/AA/6/60 H2N2 LAIV is used as a master donor virus (MDV) for the generation of both seasonal or potentially pandemic human LAIV by creating reassortant viruses containing the six internal vRNA segments (PB2, PB1, PA, NP, M, and NS) from A/AA/6/60 H2N2 LAIV, responsible for the attenuated phenotype, and the two glycoprotein encoding vRNAs (HA and NA) from a virus that antigenically matches the strains predicted to circulate in the upcoming influenza season (in the case of a seasonal vaccine) or potentially pandemic strains (in the case of the pandemic vaccine) (Maassab, 1999, Reviews in medical virology, 9: 237-244, Murphy et a., 2002, Viral immunology, 15: 295-323.). It has been previously shown that five ts mutations (PB2 N265S; PB1 K391E, D581G, A661T; and NP D34G) are responsible for the ts, ca, att phenotype of the A/AA/6/60 H2N2 LAIV. Moreover, introduction of these mutations in other influenza viruses has been shown to be sufficient to impart a strong ts phenotype and attenuation in other viral strains, such as PR8 (Cox et al., 2015, J Virol, 89(6): 3421-3426, Jin et al., 2004, J Virol, 78: 995-998) and pH1N1 (Zhou et al., 2012, Vaccine, 30: 3691-3702).

Intranasal immunization is a desirable delivery method to prevent infection with IAV because it leads to the generation of a mucosal immune responses, creating an immune barrier at the site of potential infection (Kohlmeier et al., 2009, Annual review of immunology, 27: 61-82). Indeed, LAIVs elicit not only a robust systemic humoral response but also a mucosal immune response (Cheng et al., 2013, The Journal of infectious diseases, 208: 594-602, De Villiers et al., 2009, Vaccine, 28: 228-234, Katsura et al., 2012, Vaccine, 30: 6027-6033, Murphy et al., 2002, Viral immunology, 15: 295-323, Victor et al., 2012, J Virol, 86(8): 4123-4128). Similar to infection with WT IAV, it has been showed that LAIV immunization also leads to recruitment of influenza-specific CD8 T cells to the lungs (Baker et al., 2013, J Virol, 87: 8591-8605, Guo et al., 2014, J Virol, 88: 12006-12016, Katsura et al., 2012, Vaccine, 30: 6027-6033, Powell et al., 2012, J Virol, 86: 13397-13406, Uraki et al., 2013, J Virol, 87: 7874-7881), which is likely to be the main contributor of immunity against heterologous influenza challenge (Baker et al., 2013, J Virol, 87: 8591-8605, Guo et al., 2014, J Virol, 88: 12006-12016). Thus, a LAIV rather than IIV is desired for the control of IAV infections.

Since the emergence of H3N8 CIV in 1999 in the USA and the H3N2 CIV in Asia in 2005, CIVs have been circulating in the dog populations, particularly in shelters (Crawford et al., 2005, Science, 310: 482-485, Holt et al., 2010, Journal of the American Veterinary Medical Association, 237: 71-73). Indeed, H3N8 and H3N2 CIVs are routinely isolated from such facilities (Hayward et al., 2010, J Virol, 84:12636-12645, Pecoraro et al., 2013, Journal of veterinary diagnostic investigation, 25: 402-406, Rivailler et al., 2010, Virology, 408: 71-79). Notably, H3N2 CIV has appeared to not be limited to Asia, and recently (2015) has been imported to the USA. Importantly, H3N8 and H3N2 CIVs not only represent a new threat to canine health, since they could overcome the species barrier and infect humans or other species. In fact, the H3 subtype of IAV are able to infect multiples species, including humans, pigs, horses, dogs, cats, seals, poultry and wild aquatic birds (Bean et al., 1992, J Virol, 66:1129-1138, Both et al., 1983, J Virol, 48:52, Bush et al., 1999, Molecular biology and evolution, 16: 1457-1465, de Jong et al., 2007, J Virol, 81: 4315-4322, Epperson et al., 2013, Clinical infectious diseases, 57 Suppl 1:S4-S11, Rivailler et al., 2010, Virology, 408: 71-79, Song et al., 2008, Emerging infectious diseases, 14: 741-746). Moreover, it has been shown the possibility of H3N8 CIV to reassort with H1N1 IAV (Gonzalez et al., 2014, J Virol, 88: 9208-9219). Furthermore, reassortment between CIVs and human IAVs is not without precedent, as a naturally occurring H3N1 virus carrying the HA gene of an avian-like H3N2 CIV and the other seven segments of the human pH1N1 has been reported (Song et al., 2012, The Journal of general virology, 93: 551-554). Therefore, dogs could act as an intermediate host for genetic reassortment between mammalian (including human) and avian IAVs, facilitating the generation of new IAVs with pandemic potential for humans. To date, no transmission of H3N8 or H3N2 CIV transmission from dogs to humans have been reported.

There is an opportunity to control or even eradicate H3N8 and H3N2 CIVs from the dog population throughout vaccination, therefore reducing the possibility of their transmission into humans or the risk of generating, by reassortment with other IAVs, new viral strains with a pandemic potential for humans. Currently, only IIV are available for the treatment of H3N8 or H3N2 CIV infections but their efficacy is limited. Thus, the generation and implementation of CIV LAIVs represent a better option for the treatment of CIV infections since they afford better and faster induction of adaptive immune responses, as it has been shown with human influenza vaccines (Belshe et al., 2007, The New England journal of medicine, 356: 685-696). Moreover, they also represent an excellent option for the potential eradication of CIVs from the dog population, before they jump to other animal species. Successful CIV LAIV candidates must show in vivo attenuation, while retaining immunogenicity and protection efficacy, and must also grow well in manufacturing-suitable tissue culture platforms (Hussain et al., 2010, Vaccine, 28: 3848-3855, Pica et al., 2013, Annual review of medicine, 64: 189-202).

In this study the feasibility of generating an H3N8 LACIV is demonstrated by introducing the four amino acid changes present in the viral polymerase PB2 and PB1 into the backbone of the H3N8 CIV. It is shown that the H3N8 LACIV replicates efficiently in vitro at permissive low (33° C.) temperatures but is restricted at high (37° C. and 39° C.) temperatures (FIG. 1 and FIG. 2). Importantly, the H3N8 LACIV was attenuated, as compared with H3N8 CIV WT, in the lungs of infected mice (FIG. 3) but able to induce protective immune responses against challenge with homologous H3N8 CIV challenge (FIG. 4). Remarkably, H3N8 LACIV elicited better humoral responses and protection than that obtained with a commercial H3N8 IIV (Nobivac). However, the H3N8 LACIV induced low levels of cross-reactive antibodies and limited protection efficacy against an heterologous challenge with H3N2 CIV (FIG. 6), demonstrating the need of generating an H3N2 LACIV for the treatment of H3N2 CIV infections in dogs.

TABLE 3

Immunogenicity of LACIV and sciCIV

| Immunization and dose[a] | | Mean (SD) serum HAI titer[b] |
|---|---|---|
| PBS | — | ≤8 (ND) |
| WT | $10^3$ PFU | 215.3 (64) |
| LACIV | $10^3$ | 76.1 (32) |
| Nobivac | 100 μl | 26.9 (8) |

[a]Virus was administered intranasally to anesthetized mice (n = 4), Nobivac was administered intramuscularly, and sera were collected at 14 days postinfection.
[b]Four HAU of the WT virus was incubated with 2-fold serial dilutions of the indicated sera.
ND, not determined.

Example 2: Development and Characterization of a Live Attenuated Influenza Vaccine (LAIV) Against H3N2 CIV Based on a Temperature Sensitive (Ts) Mutant Described herein are experiments used to develop, generate, and characterize, a LAIV for CIV H3N2. The H3N2 LAIV presented herein is based on the CIV H3N8 LAIV, described in Example 1, which was used as a master donor virus (MDV) to express the HA and NA of CIV H3N2. As, the temperature sensitive H3N8 LAIV has demonstrated to be safe, it can be used as an MDV to express viral proteins from other circulating strains to update the LAIV to protect against new strains.

The nucleotide sequences for each segment, and amino acid sequences for each encoded protein, of the H3N8 CIV, are provided in SEQ ID NOs: 5-22. The mutated sequences for segment 1, PB2 protein, segment 2, and PB1 protein, are provided in SEQ ID NOs: 1-4, FIG. 13, and FIG. 14. The nucleotide sequences for segment 4 and segment 6, and the amino acid sequences of the encoded HA and NA, of the H3N2 CIV, used in the development of the H3N2 LAIV described herein are provided in SEQ ID NOs: 23-26.

Figure 7:
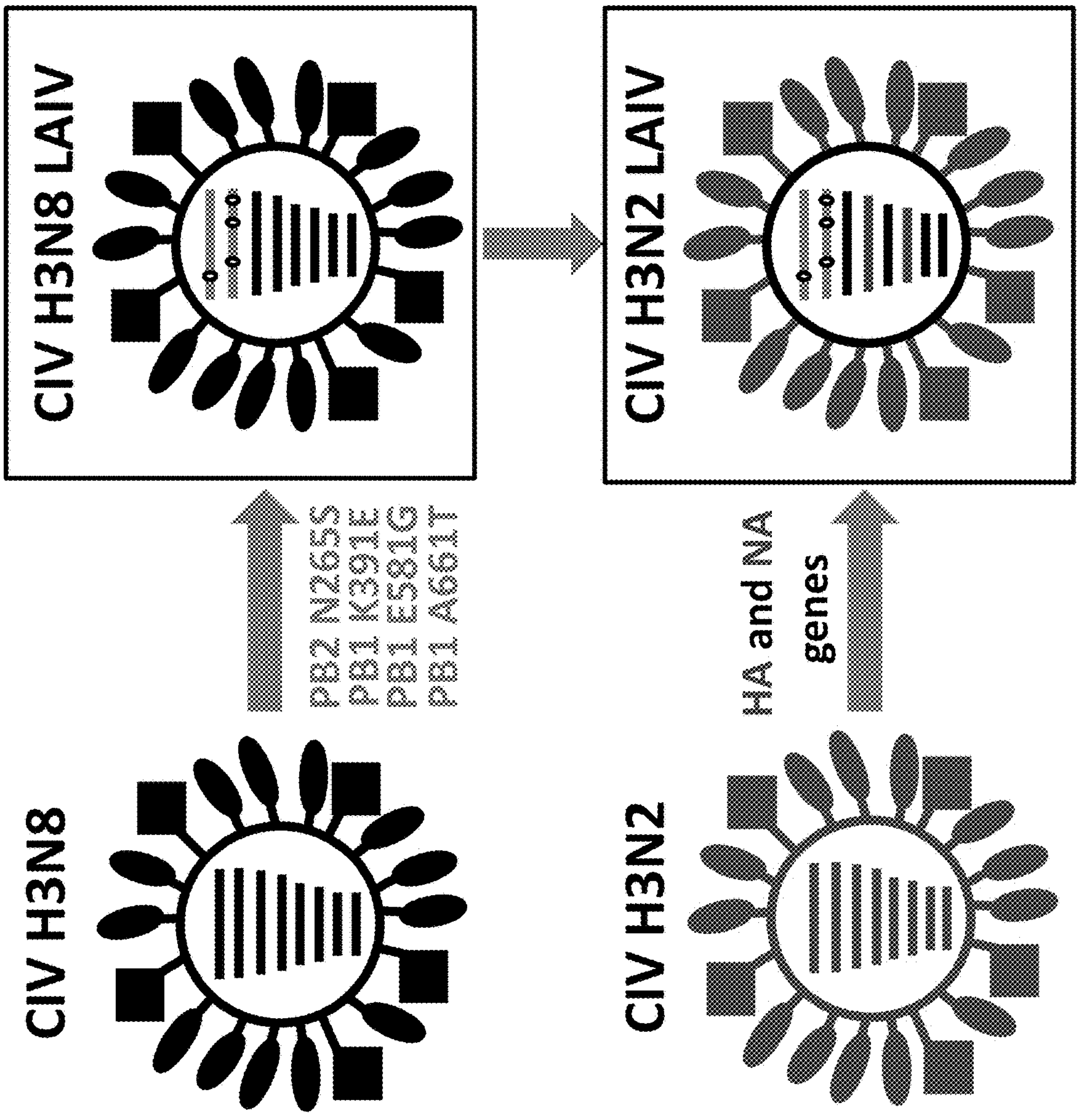
FIG. 7 is a schematic representation of the generation of CIV H3N2 LAIV: Amino acid substitutions N265S (PB2) and K391E, E581G, and A661T (PB1) were introduced into the A/canine/NY/dog23/2009 H3N8 (CIV H3N8) to generate the CIV H3N8 LAIV. CIV H3N8 LAIV was used as a master donor virus (MDV) to generate the CIV H3N2 LAIV that contains the internal viral segments (PB2, PB1, PA, NP, M and NS) of CIV H3N8 LAIV and the HA and NA of A/Ca/IL/41915/2015 H3N2 (CIV H3N2).

FIG. 7 is a schematic depicting the generation of the CIV H3N2 LAIV, based upon the CIV H3N8 LAIV described in Example 1. As described above, the CIV H3N8 LAIV comprises specific amino acid substitutions in PB1 and PB2. Amino acid substitutions N265S (PB2) and K391E, E581G, and A661T (PB1) were introduced into the A/canine/NY/dog23/2009 H3N8 (CIV H3N8) to generate the CIV H3N8 LAIV. CIV H3N8 LAIV was used as a master donor virus (MDV) to generate the CIV H3N2 LAIV that contains the internal viral segments (PB2, PB1, PA, NP, M and NS) of CIV H3N8 LAIV and the HA and NA of A/Ca/IL/41915/2015 H3N2 (CIV H3N2).

Figure 8A:
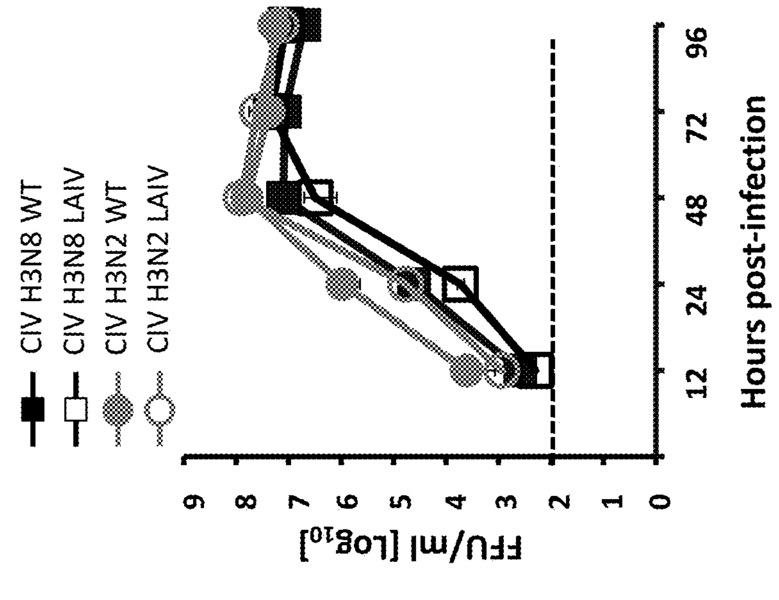
FIG. 8A through FIG. 8C, depicts the results of experiments examining the multicycle growth kinetics of CIV H3N2 LAIV: Canine MDCK cells (12-well plate format, $5\times10^5$ cells/well, triplicates) were infected at low multiplicity of infection (MOI, 0.001) with A/Canine/Illinois/11613/2015 H3N2 (CIV H3N2 WT), A/Canine/NY/Dog23/2009 H3N8 (CIV H3N8 WT) and the two LAIVs (CIV H3N2 LAIV and CIV H3N8 LAIV) and incubated at 33° C.
Figure 8B:
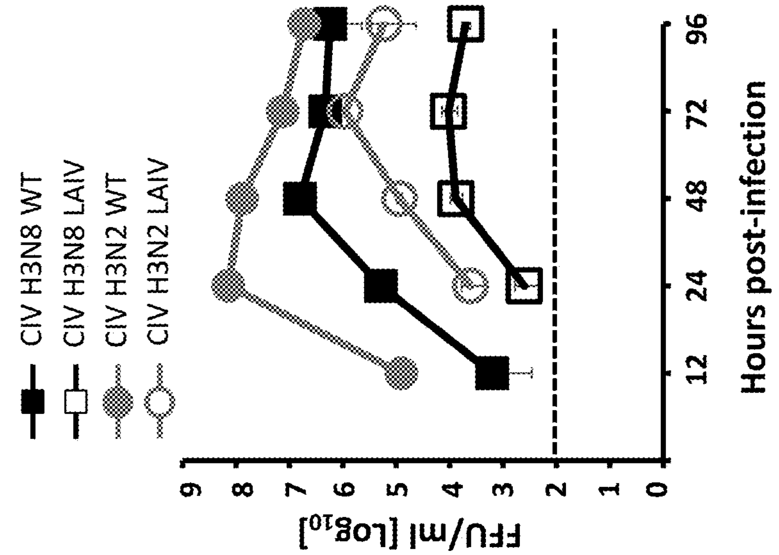
Figure 8C:
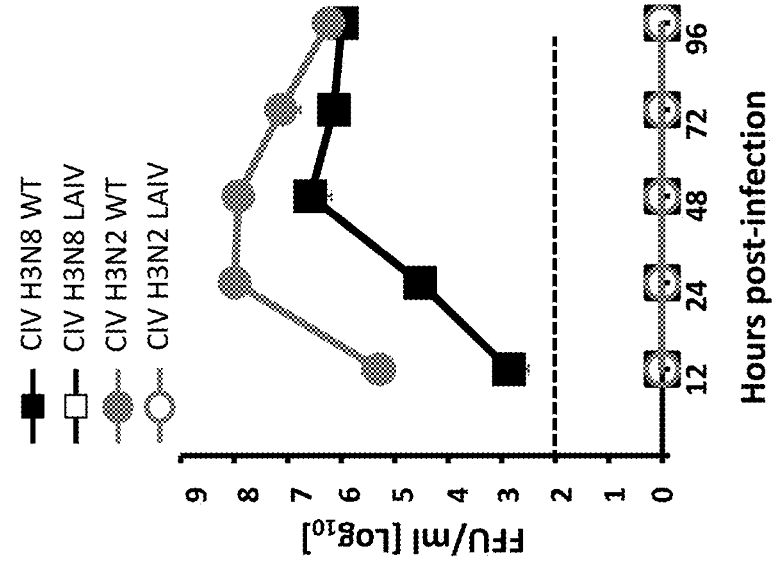

Experiments were then conducted to examine the growth kinetics of the CIV H3N2 LAIV. Canine MDCK cells (12-well plate format, $5\times10^5$ cells/well, triplicates) were infected at low multiplicity of infection (MOI, 0.001) with A/Canine/Illinois/11613/2015 H3N2 (CIV H3N2 WT), A/Canine/NY/Dog23/2009 H3N8 (CIV H3N8 WT) and the two LAIVs (CIV H3N2 LAIV and CIV H3N8 LAIV) and incubated at 33° C. (FIG. 8A), 37° C. (FIG. 8B) and 39° C. (FIG. 8C). Tissue culture supernatants were collected at 12, 24, 48, 72 and 96 hours post-infection. Viral titers in tissue culture supernatants were determined by immunofocus assay (Focus Forming Units, FFU/ml) using an anti-NP monoclonal antibody (HT-103). It was observed that the H3N2 LAIV displayed similar growth, as compared to WT, at 33° C., but is attenuated at 37° C. and 39° C. (FIG. 8A-FIG. 8C).

Figure 9B:
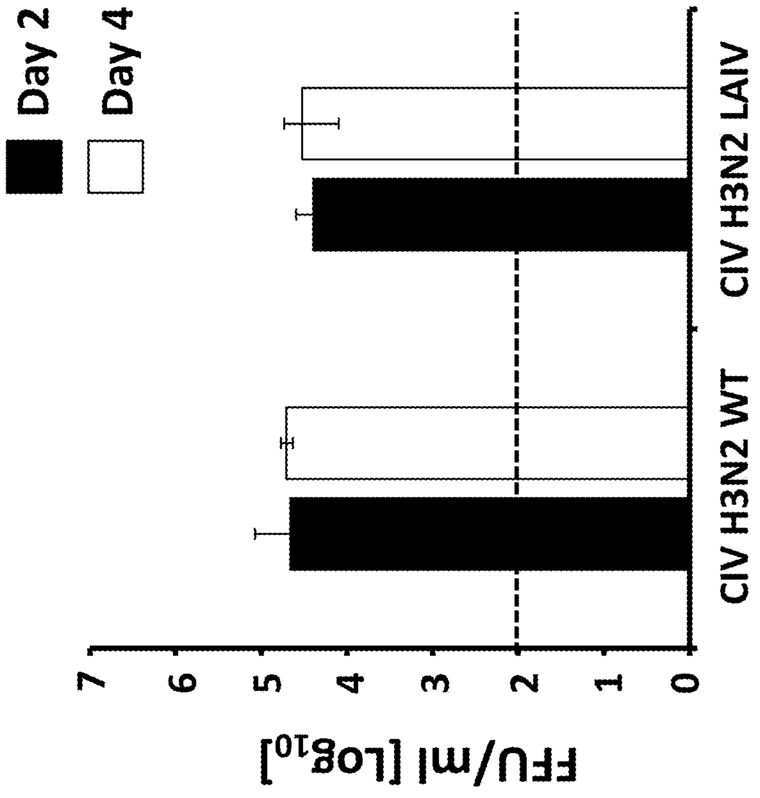
FIG. 9A and FIG. 9B, depicts the results of experiments demonstrating the attenuation of CIV H3N2 LAIV: Female 6-to-8-week-old C57BL/6 WT mice (N=6) were infected intranasally (i.n.) with $1\times10^5$ FFU of CIV H3N2 WT or CIV H3N2 LAIV. Presence of viruses in the lungs (FIG. 9A) and the nasal mucosal (FIG. 9B) of infected mice were evaluated at days 2 (N=3) and 4 (N=3) post-infection by immunofocus assay (FFU/ml) using an anti-NP monoclonal antibody (HT-103). Data represent the means+/−SDs. Dotted black lines indicate limit of detection (200 FFU/ml). *, $P<0.05$ and **, $P<0.001$ (WT vs LAIV) using Student's t test (n=3).
Figure 9A:
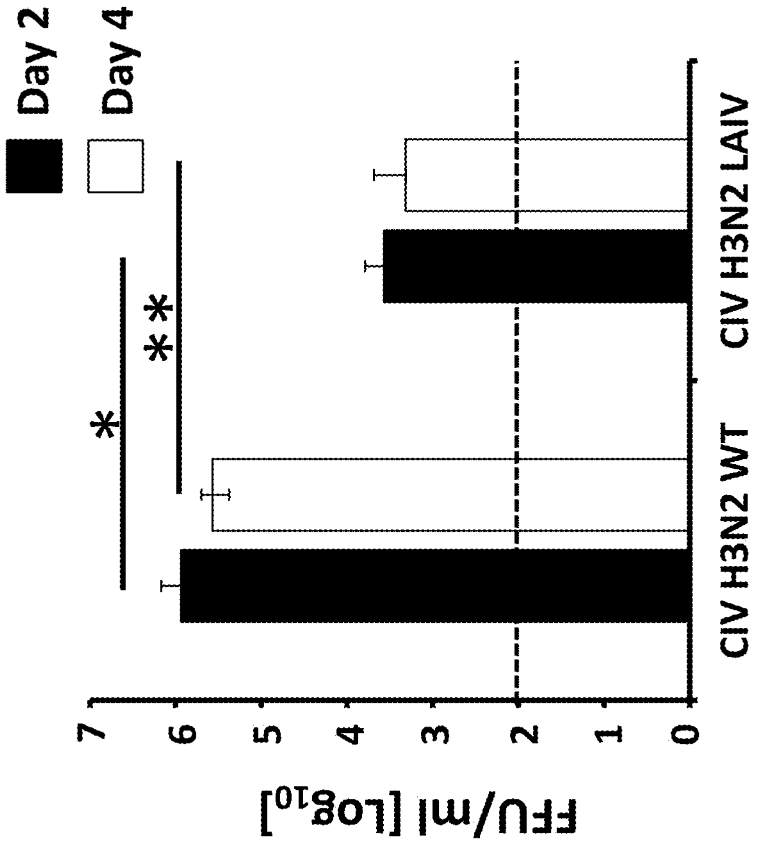

Next, experiments were conducted to examine the attenuation of CIV H3N2 LAIV. Female 6-to-8-week-old C57BL/6 WT mice (N=6) were infected intranasally (i.n.) with $1\times10^5$ FFU of CIV H3N2 WT or CIV H3N2 LAIV. Presence of viruses in the lungs (FIG. 9A) and the nasal mucosal (FIG. 9B) of infected mice were evaluated at days 2 (N=3) and 4 (N=3) post-infection by immunofocus assay (FFU/ml) using an anti-NP monoclonal antibody (HT-103). Significantly less virus was detected in the lungs of mice infected with the H3N2 LAIV, as compared to H3N2 WT (FIG. 9A).

Figure 10A:
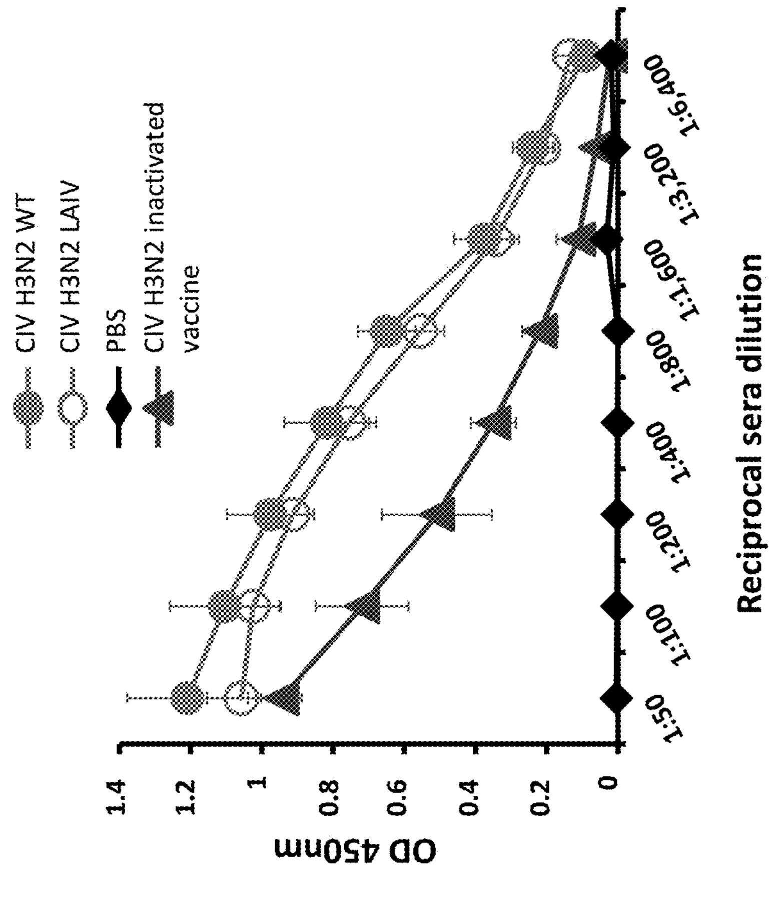
FIG. 10A and FIG. 10B, depicts the results of experiments investigating the induction of humoral responses by CIV H3N2 LAIV: Female 6-to-8-week-old C57BL/6 WT mice (N=6) were immunized with $1\times10^3$ FFU of CIV H3N2 WT or CIV H3N2 LAIV. Mice were also mock vaccinated or vaccinated with 100 ul/mice of an inactivated CIV H3N2 vaccine (Zoetis) as negative and positive controls, respectively. At 14 days post-vaccination, mice were bled and the sera were collected and evaluated individually by ELISA for IgG antibodies against total influenza virus protein using cell extracts of MDCK cells infected with A/Canine/Illinois/11613/2015 H3N2 WT virus (FIG. 10A) or A/Canine/NY/Dog23/2009 H3N8 WT virus (FIG. 10B). Mock-infected cell extracts were used to evaluate the specificity of the antibody response. OD, optical density. Data represent the means+/−SDs of the results for 6 individual mice.
Figure 10B:
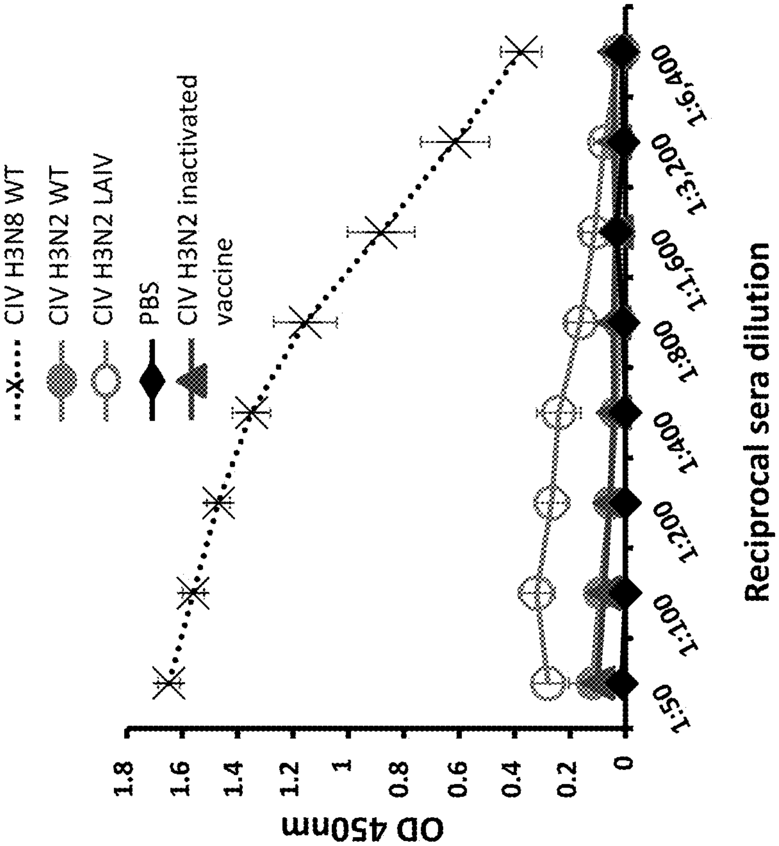

Next, experiments were conducted examining the induction of humoral responses by CIV H3N2 LAIV. Female 6-to-8-week-old C57BL/6 WT mice (N=6) were immunized with $1\times10^3$ FFU of CIV H3N2 WT or CIV H3N2 LAIV. Mice were also mock vaccinated or vaccinated with 100 μl/mice of an inactivated CIV H3N2 vaccine (Zoetis) as negative and positive controls, respectively. At 14 days post-vaccination, mice were bled and the sera were collected and evaluated individually by ELISA for IgG antibodies against total influenza virus protein using cell extracts of MDCK cells infected with A/Canine/Illinois/11613/2015 H3N2 WT virus (FIG. 10A) or A/Canine/NY/Dog23/2009 H3N8 WT virus (FIG. 10B). Mock-infected cell extracts were used to evaluate the specificity of the antibody response. It is demonstrated that the H3N2 LAIV induced a greater H3N2 specific immune response, as compared to the inactivated H3N2 CIV, and comparable to H3N2 WT (FIG. 10A).

Figure 11A:
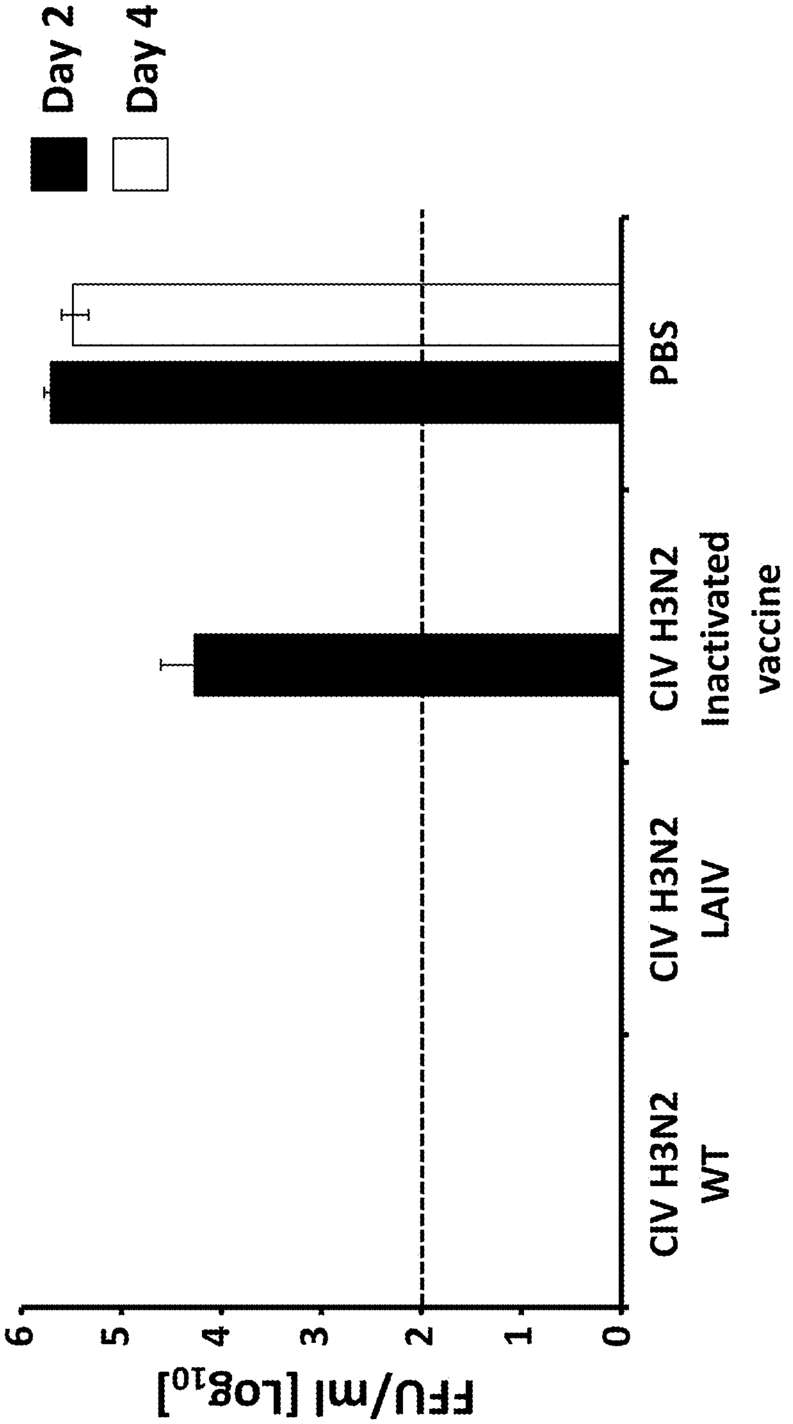
FIG. 11A and FIG. 11B, depicts the results of experiments investigating the protection efficacy of CIV H3N2 LAIV: Female 6-to-8-week-old C57BL/6 WT mice (N=12) were vaccinated with $1\times10^3$ FFU of CIV H3N2 WT or CIV H3N2 LAIV. Mice were also mock vaccinated or vaccinated with 100 ul/mice of a CIV H3N2 inactivated vaccine (Zoetis) as negative and positive controls, respectively. Two weeks post-vaccination, mice (N=6) were challenged with $1\times10^5$ FFU of CIV H3N2 WT (FIG. 11A) or CIV H3N8 WT (FIG. 11B). Viral titers of challenged viruses at days 2 (N=3) and 4 (N=3) post-infection were evaluated from lung homogenates by immunofocus assay (FFU/ml) using an anti-NP monoclonal (HT-103 or HB-65 respectively). Dotted black lines indicate limit of detection (200 FFU/ml). Data represent the means+/−SDs.
Figure 11B:
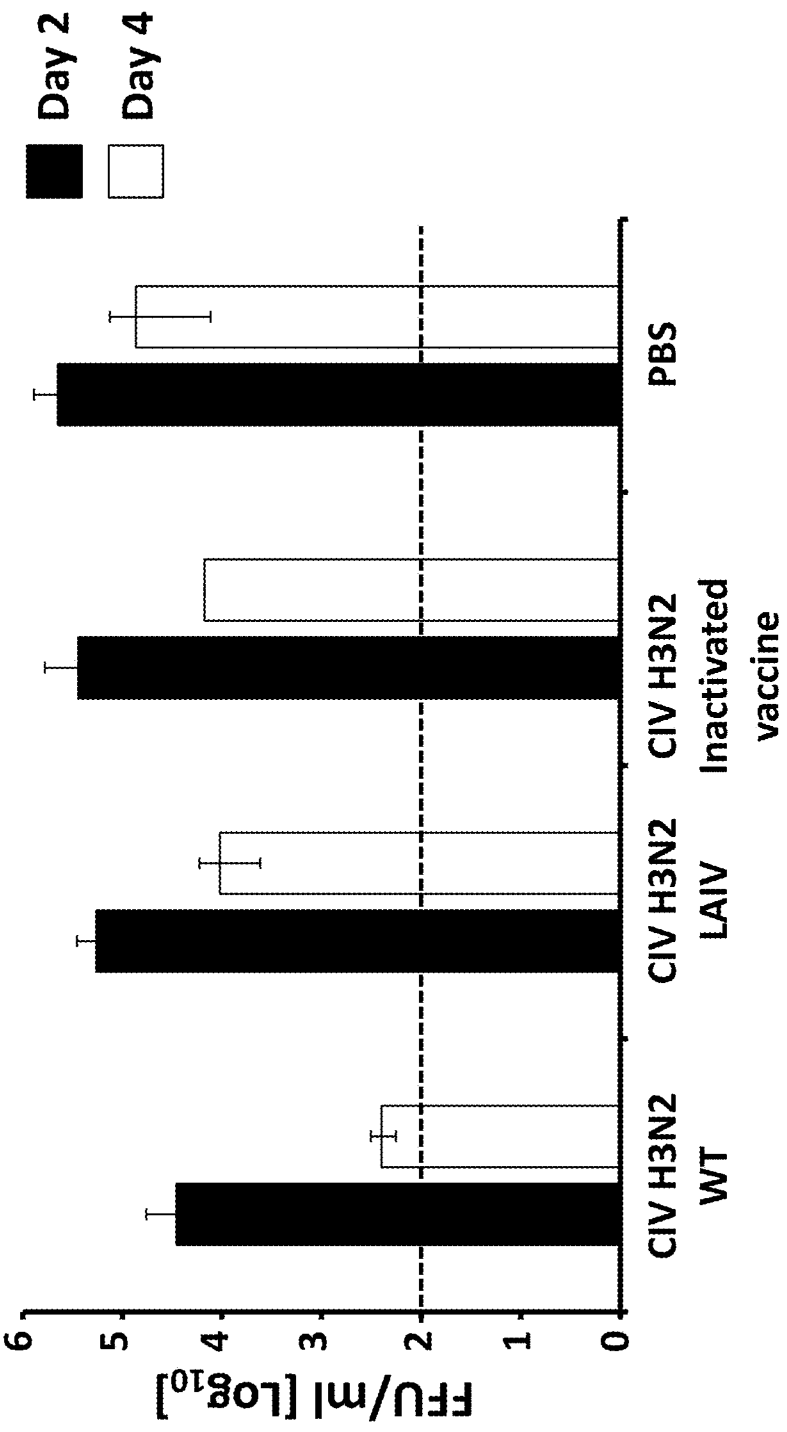

Next, experiments were conducted examining the protection efficacy of CIV H3N2 LAIV. Female 6-to-8-week-old C57BL/6 WT mice (N=12) were vaccinated with $1\times10^3$ FFU of CIV H3N2 WT or CIV H3N2 LAIV. Mice were also mock vaccinated or vaccinated with 100 ul/mice of a CIV H3N2 inactivated vaccine (Zoetis) as negative and positive controls, respectively. Two weeks post-vaccination, mice (N=6) were challenged with $1\times10^5$ FFU of CIV H3N2 WT (FIG. 11A) or CIV H3N8 WT (FIG. 11). Viral titers of challenged viruses at days 2 (N=3) and 4 (N=3) post-infection were evaluated from lung homogenates by immunofocus assay (FFU/ml) using an anti-NP monoclonal (HT-103 or HB-65 respectively). It is observed that the vaccination with H3N2 LAIV completely protected against H3N2 challenge, and was improved over results from mice vaccinated with inactivated H3N2 CIV (FIG. 11A).

Figure 12:
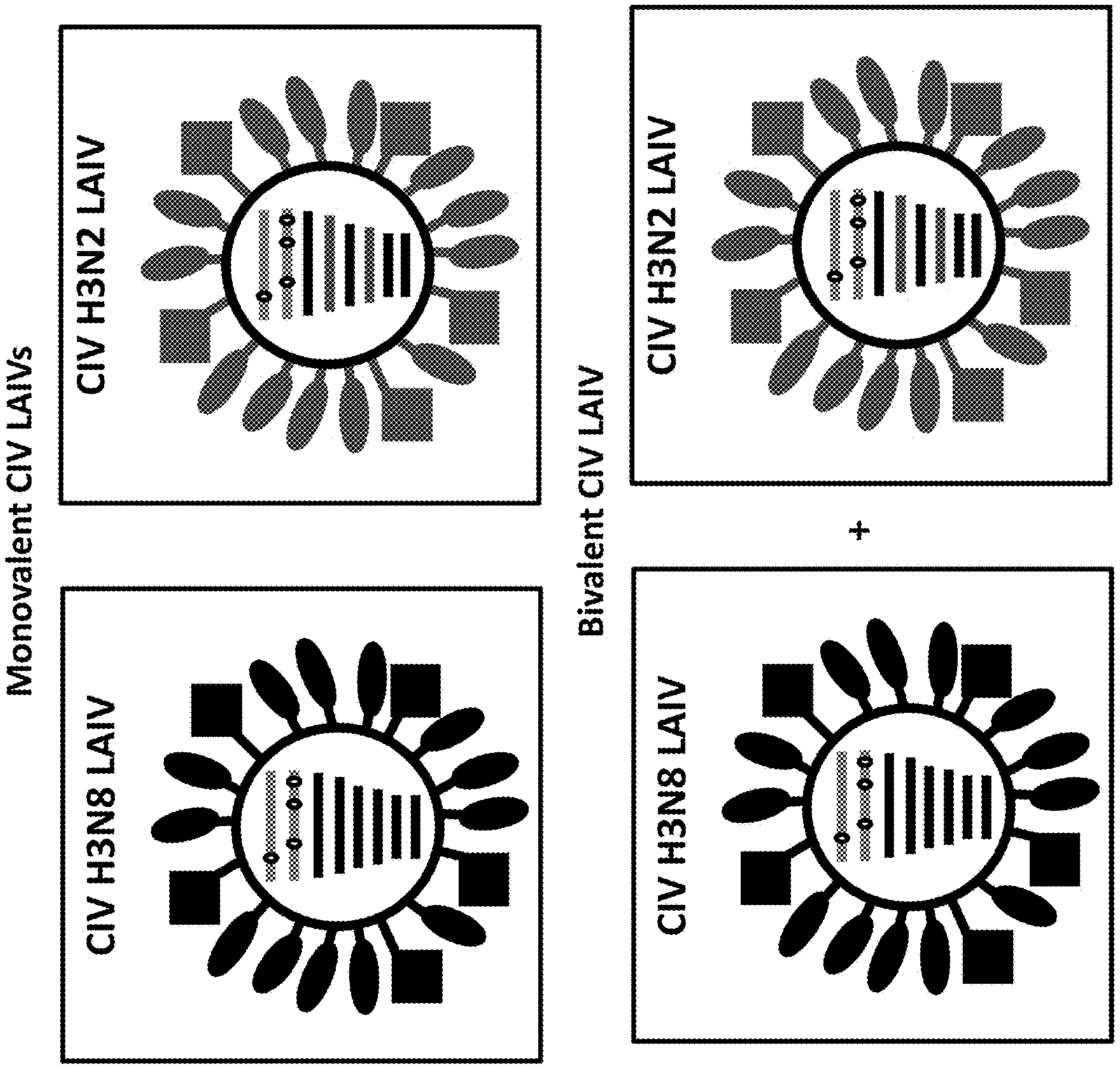
FIG. 12 is a schematic representation of bivalent CIV LAIV comprising the CIV H3N8 LAIV and the CIV H3N2 LAIV.

Based on the promising results with the CIV H3N8 LAIV and CIV H3N2 LAIVs, it is examined whether vaccination with both CIV H3N8 and H3N2 LAIVs confer protection against challenge against both CIVs for its implementation as a bivalent vaccine (FIG. 12)

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunological composition comprising a live-attenuated canine influenza virus (LACIV), wherein the LACIV comprises one or more mutations selected from the group consisting of: (a) a mutation in segment 1 of the viral genome encoding a mutant PB2 comprising a N265S point mutation; (b) a mutation in segment 2 of the viral genome encoding a mutant PB1 comprising a K391E point mutation; (c) a mutation in segment 2 of the viral genome encoding a mutant PB1 comprising a E581G point mutation; (d) and a mutation in segment 2 of the viral genome encoding a mutant PB1 comprising A661T point mutation; further wherein all segments of the viral genome are of canine influenza virus origin; wherein said mutant PB2 comprises an amino acid sequence that is at least 95% identical to the amino acid sequence of SEQ ID NO: 3, and wherein said mutant PB1 comprises an amino acid sequence that is at least 95% identical to the amino acid sequence of SEQ ID NO: 4.

2. The composition of claim 1, wherein the LACIV comprises (a) a mutation in segment 1 of the viral genome encoding a mutant PB2 comprising a N265S point mutation; (b) a mutation in segment 2 of the viral genome encoding a mutant PB1 comprising a K391E point mutation; (c) a mutation in segment 2 of the viral genome encoding a mutant PB1 comprising a E581G point mutation; (d) and a mutation in segment 2 of the viral genome encoding a mutant PB1 comprising A661T point mutation.

3. The composition of claim 1, wherein the LACIV exhibits reduced viral replication as compared to wildtype canine influenza virus at a temperature selected from the group consisting of normal body temperature and elevated body temperature.

4. The composition of claim 1, wherein the LACIV is derived from H3N8 subtype of influenza A virus.

5. The composition of claim 1, wherein the LACIV expresses HA and NA of H3N8.

6. The composition of claim 1, wherein the LACIV expresses HA and NA of H3N2.

7. A method for treating or preventing canine influenza in a subject, the method comprising administering to the subject the composition immunological composition of claim 1.

8. An immunological composition comprising a live-attenuated influenza virus (LAIV), wherein the LAIV comprises: (a) segment 1 of the viral genome comprising a nucleic acid sequence that is at least 95% identical to SEQ ID NO: 1 wherein the segment 1 encodes a mutant PB2 comprising a N265S point mutation; and (b) segment 2 of the viral genome comprising a nucleic acid sequence that is at least 95% identical to SEQ ID NO: 2 wherein segment 2 encodes a mutant PB1 comprising a mutation in segment 2 of the viral genome encoding a mutant PB1 comprising a K391E point mutation, a E581G point mutation, and a mutant PB1 comprising A661T point mutation.

9. The composition of claim 8, wherein the mutant PB2 comprises an amino acid sequence that is at least 95% identical to SEQ ID NO: 3.

10. The composition of claim 8, wherein the mutant PB2 comprises an amino acid sequence that is at least 95% identical to SEQ ID NO: 4.

11. The composition of claim 8, wherein segment 1 comprises a nucleic acid sequence that is at least 98% identical to SEQ ID NO: 1.

12. The composition of claim 8, wherein segment 1 comprises a nucleic acid sequence that is at least 98% identical to SEQ ID NO: 2.

13. The composition of claim 8, wherein the mutant PB2 comprises an amino acid sequence that is at least 98% identical to SEQ ID NO: 3.

14. The composition of claim 8, wherein the mutant PB2 comprises an amino acid sequence that is at least 98% identical to SEQ ID NO: 4.

15. The composition of claim 8, wherein the LAIV exhibits reduced viral replication as compared to wildtype influenza virus at a temperature selected from the group consisting of normal body temperature and elevated body temperature.

16. The composition of claim 8, wherein the LAIV is derived from H3N8 subtype of influenza A virus.

17. The composition of claim 8, wherein the LAIV expresses HA and NA of H3N8.

18. The composition of claim 8, wherein the LAIV expresses HA and NA of H3N2.

19. A method for treating or preventing influenza in a subject, the method comprising administering to the subject the composition immunological composition of claim 8.

* * * * *